United States Patent
Kim

(10) Patent No.: US 9,759,717 B2
(45) Date of Patent: Sep. 12, 2017

(54) METHOD FOR QUANTITATIVELY SENSING AND EFFECTIVELY MARKING INTERACTION WITH TARGET MATERIAL BY USING ENERGY TRANSFER AND SIGNAL CHANGE BASED ON HIGH-DENSITY DISPLAY OF MATERIAL

(75) Inventor: Tae Kook Kim, Gyeonggi-do (KR)

(73) Assignee: T&K BIOINNOVATION INC., Seoul (KR)

(*) Notice: Subject to any disclaimer, the term of this patent is extended or adjusted under 35 U.S.C. 154(b) by 746 days.

(21) Appl. No.: 14/237,840

(22) PCT Filed: Aug. 10, 2012

(86) PCT No.: PCT/KR2012/006399
§ 371 (c)(1),
(2), (4) Date: Apr. 20, 2014

(87) PCT Pub. No.: WO2013/022313
PCT Pub. Date: Feb. 14, 2013

(65) Prior Publication Data
US 2014/0309132 A1  Oct. 16, 2014

(30) Foreign Application Priority Data
Aug. 10, 2011 (KR) .......... 10-2011-0079888

(51) Int. Cl.
*G01N 33/543* (2006.01)
*C40B 30/04* (2006.01)
(Continued)

(52) U.S. Cl.
CPC ..... *G01N 33/54306* (2013.01); *G01N 33/542* (2013.01); *G01N 33/54366* (2013.01); *B82Y 15/00* (2013.01); *C40B 30/04* (2013.01)

(58) Field of Classification Search
None
See application file for complete search history.

(56) References Cited

U.S. PATENT DOCUMENTS 7,371,719 B2   5/2008 Stupp et al.
2004/0028694 A1   2/2004 Young et al.

FOREIGN PATENT DOCUMENTS

| KR | 10-2009-0018585 A | 2/2009 |
| WO | 2007058454 A1 | 5/2007 |
| WO | 2009025475 A2 | 2/2009 |

OTHER PUBLICATIONS

Ashburn, T., et al., "Drug Repositioning: Identifying and Developing New Uses for Existing Drugs", "Nature Reviews: Drug Discovery", Aug. 2004, pp. 673-683, vol. 3.

(Continued)

*Primary Examiner* — Kaijiang Zhang
(74) *Attorney, Agent, or Firm* — Hultquist, PLLC; Steven J. Hultquist

(57) ABSTRACT

The present invention relates to methods of quantitatively analyzing and detecting interactions, which effectively occur between detector materials displayed on a nano-assembly matrix at high density, and sensitively labeling and isolating a target material that effectively interacts with the detector materials, by the use of energy transfer and signal changes that effectively occur in label molecules displayed at high density. Specifically, the present invention relates to a method of quantitatively detecting the interactions between various bioactive materials, which occur in vitro or in vivo, based on high-density displays of molecules, and to a method of sensitively labeling a target material that interacts with these bioactive materials.

18 Claims, 38 Drawing Sheets

(51) Int. Cl.
*B82Y 15/00* (2011.01)
*G01N 33/542* (2006.01)

(56) References Cited

OTHER PUBLICATIONS

Burdine, L., et al., "Target Identification in Chemical Genetics: The (Often) Missing Link", "Chemistry & Biology", May 2004, pp. 593-597, vol. 11.
Chasteen, N., et al., "Mineralization in Ferritin: An Efficient Means of Iron Storage", "Journal of Structural Biology", 1999, pp. 182-194, vol. 126.
Clardy, J., et al., "Lessons from natural molecules", "Nature", Dec. 16, 2004, pp. 829-837, vol. 432.
Kiessling, L., et al., "Bioorganic Chemistry: Synthetic Multivalent Ligands as Probes of Signal Transduction", "Angew. Chem. Int. Ed.", 2006, pp. 2348-2368, vol. 45.
Li, M., et al, "Organization of Inorganic Nanoparticles Using Biotin-Streptavidin Connectors", "Chem. Mater.", Dec. 19, 1998, pp. 23-26, vol. 11.
Licitra, E., et al., "A three-hybrid system for detecting small ligand-protein receptor interactions", "Proc. Natl. Acad. Sci. USA", Nov. 1996, pp. 12817-12821, vol. 93.
Mammen, M., et al., "Polyvalent Interactions in Biological Systems: Implications for Design and Use of Multivalent Ligands and Inhibitors", "Angew. Chem. Int. Ed.", 1998, pp. 2754-2794, vol. 37.
Mendelsohn, A., et al., "Protein Interaction Methods-Toward an Endgame", "Science", Jun. 18, 1999, pp. 1948-1950, vol. 284, No. 5422.
Phizicky, E., et al., "Protein-Protein Interactions: Methods for Detection and Analysis", "Microbiological Reviews", Mar. 1995, pp. 94-123, vol. 59, No. 1.
Sche, P., et al., "Display cloning: functional identification of natural product receptors using cDNA-phage display", "Chemistry and Biology", Sep. 10, 1999, pp. 707-716, vol. 6.
Sekar, R., et al., "Fluorescence resonance energy transfer (FRET) microscopy imaging of live cell protein localizations", "The Journal of Cell Biology", Mar. 3, 2003, pp. 629-633, vol. 160, No. 5.
Stockwell, B., "Exploring biology with small organic molecules", "Nature", Dec. 16, 2004, pp. 846-854, vol. 432.
Strausberg, R., et al., "From Knowing to Controlling: A Path from Genomics to Drugs Using Small Molecule Probes", "Science", Apr. 11, 2003, pp. 294-295, vol. 300.
Wouters, F., et al., "Imaging biochemistry inside cells", "TRENDS in Cell Biology", May 2001, pp. 203-211, vol. 11, No. 5.
Zheng, X., et al., "Genetic and Genomic Approaches to Identify and Study the Targets of Bioactive Small Molecules", "Chemistry and Biology", May 2004, pp. 609-618, vol. 11.

Mediator (regulator) materials: A, B, (+/- C)
Detector materials: X(Bait), Y(Prey)
Nano-assembly matrix-forming materials: N Mediator (regulator) materials: A, B, (+/- C), D, E, (+/- F)
Detector materials: X(Bait), Y(Prey)
Nano-assembly matrix-forming materials: N FIG. 3
(A)
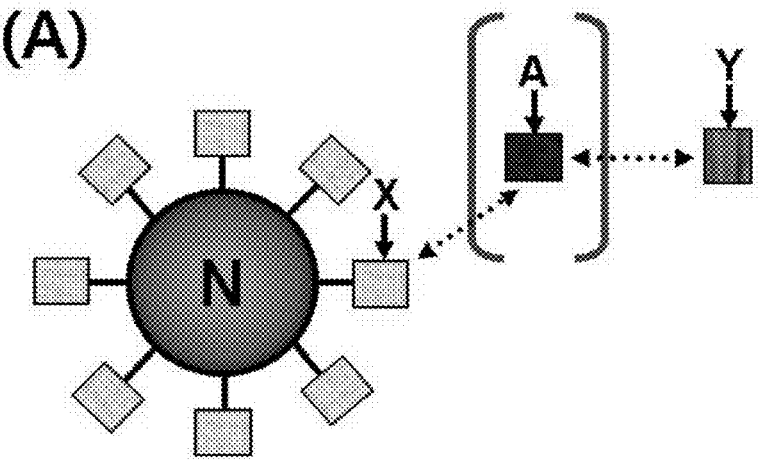
Mediator (regulator) materials: (+/- A)
Detector materials: X(Bait), Y(Prey)
Nano-assembly matrix-forming materials: N
(B)
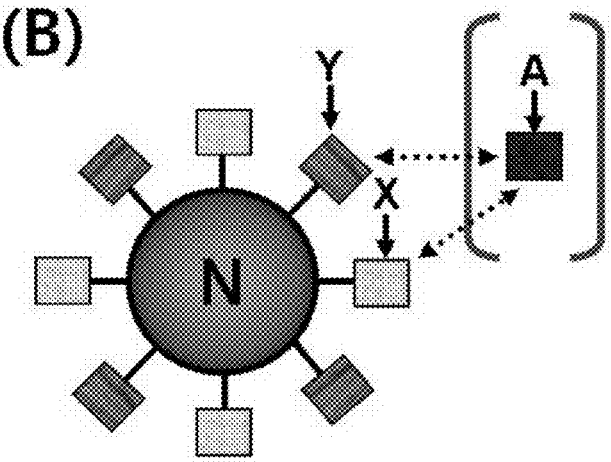
Mediator (regulator) materials: (+/- A)
Detector materials: X(Bait), Y(Prey)
Nano-assembly matrix-forming materials: N FIG. 4
(A)
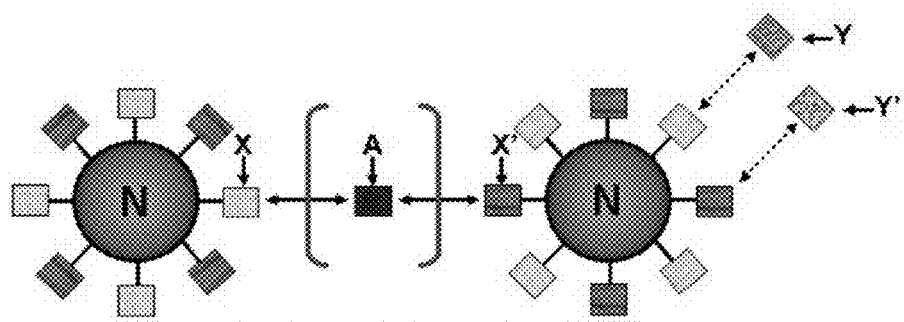
Detector materials: X, X'(Bait), Y, Y'(Prey)
Mediator (regulator) materials: (+/- A)
Nano-assembly matrix-forming materials: N
(B)
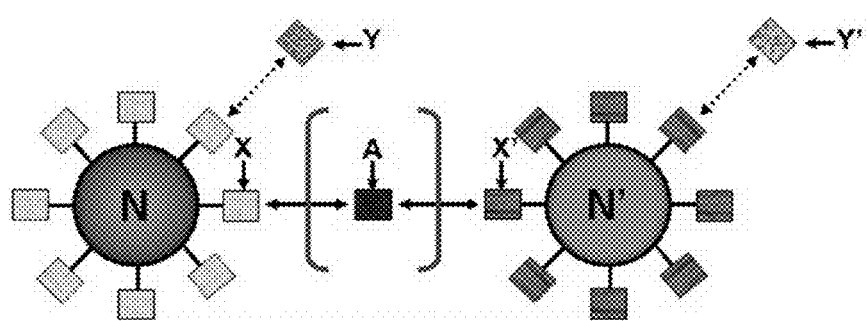
Detector materials: X, X'(Bait), Y, Y'(Prey)
Mediator (regulator) materials: (+/- A)
Nano-assembly matrix-forming materials: N, N'
(C)
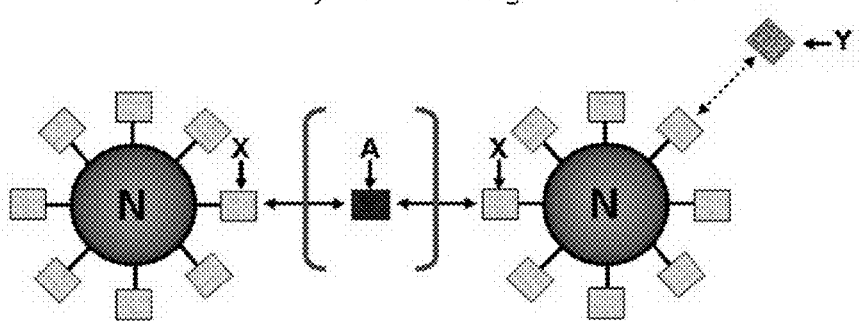
Detector materials: X(Bait), Y(Prey)
Mediator (regulator) materials: (+/- A)
Nano-assembly matrix-forming materials: N FIG. 5
(A)
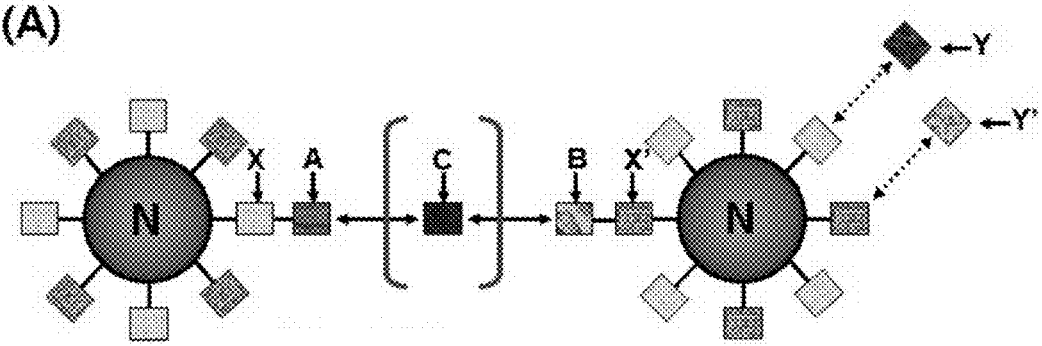
Mediator (regulator) materials: A, B, (+/- C)
Detector materials: X, X'(Bait), Y, Y'(Prey)
Nano-assembly matrix-forming materials: N
(B)
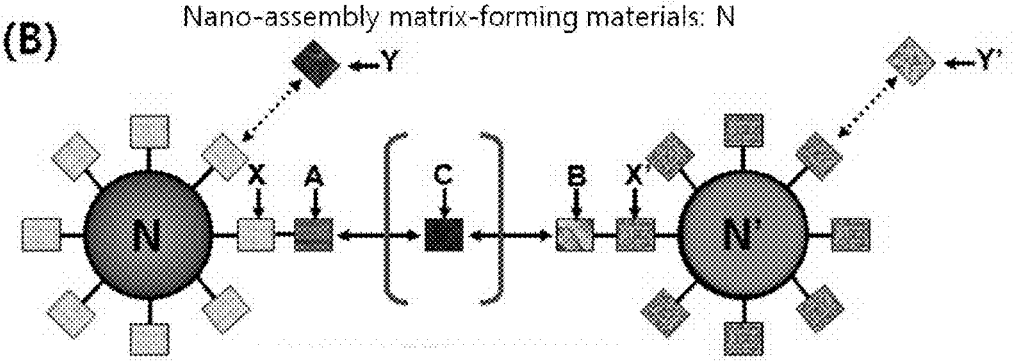
Mediator (regulator) materials: A, B, (+/- C)
Detector materials: X, X'(Bait), Y, Y'(Prey)
Nano-assembly matrix-forming materials: N, N'
(C)
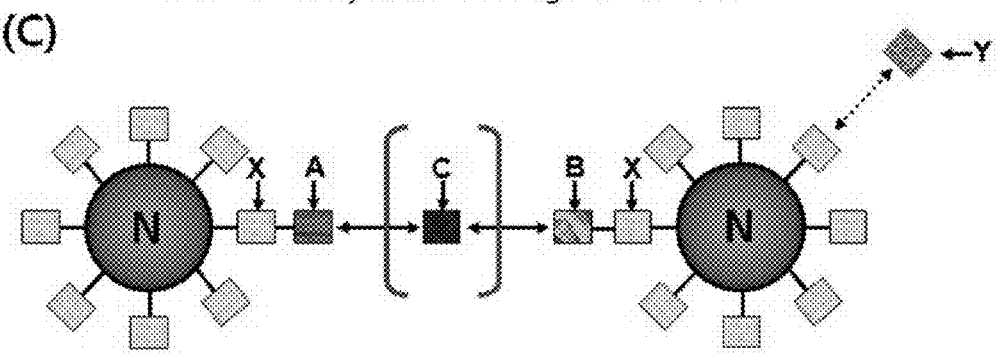
Mediator (regulator) materials: A, B, (+/- C)
Detector materials: X(Bait), Y(Prey)
Nano-assembly matrix-forming materials: N FIG. 6
(A)
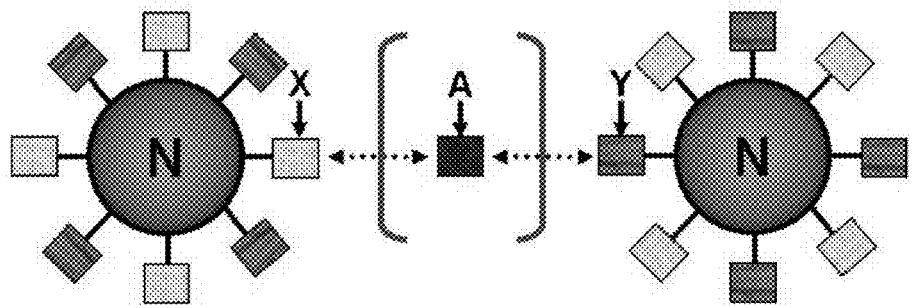
Detector materials: X (Bait), Y(Prey)
Mediator (regulator) materials: (+/- A)
Nano-assembly matrix-forming materials: N
(B)
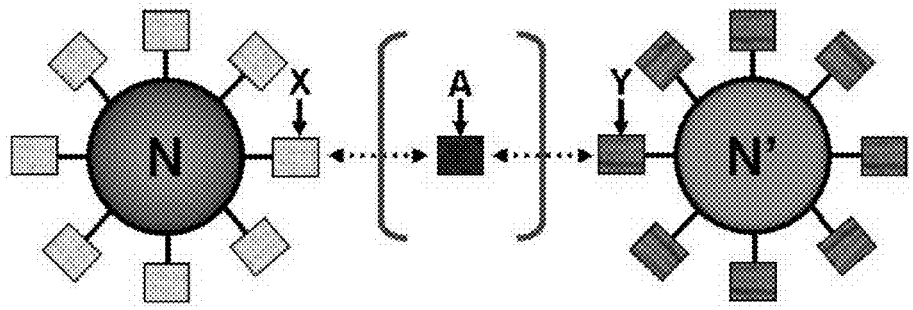
Detector materials: X (Bait), Y(Prey)
Mediator (regulator) materials: (+/- A)
Nano-assembly matrix-forming materials: N, N'

FIG. 7
(A)
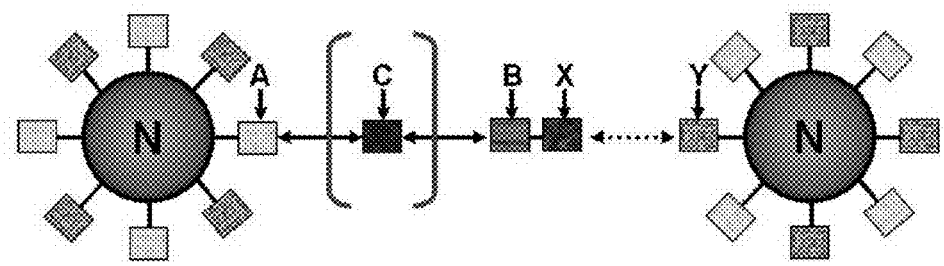
Mediator (regulator) materials: A, B, (+/- C)
Detector materials: X(Bait), Y(Prey)
Nano-assembly matrix-forming materials: N
(B)
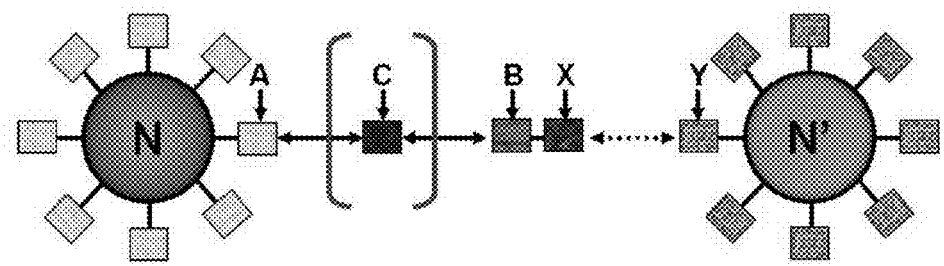
Mediator (regulator) materials: A, B, (+/- C)
Detector materials: X(Bait), Y(Prey)
Nano-assembly matrix-forming materials: N, N'

FIG. 8
(A)
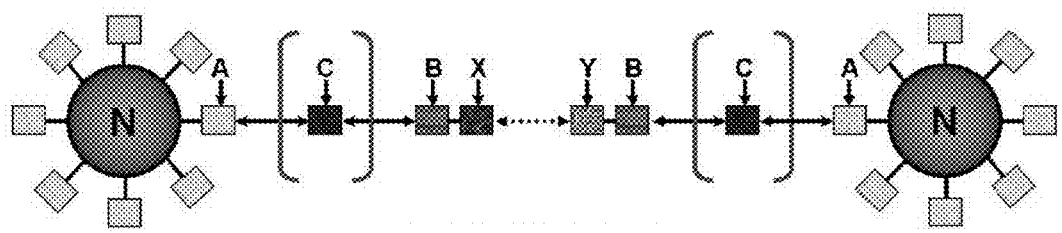
Mediator (regulator) materials: A, B, (+/- C)
Detector materials: X(Bait), Y(Prey)
Nano-assembly matrix-forming materials: N
(B)
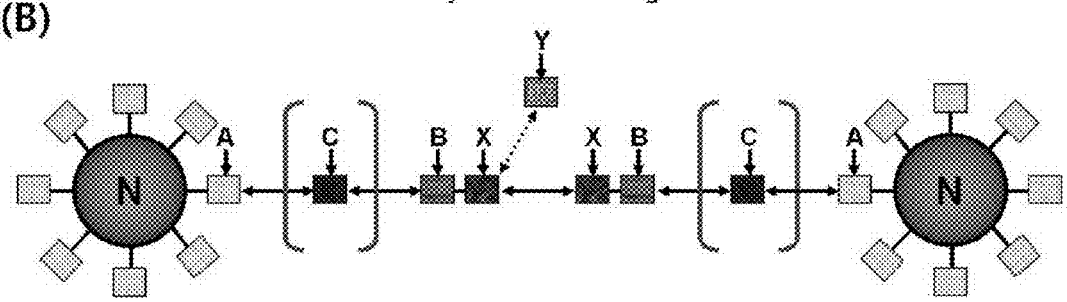
Mediator (regulator) materials: A, B, (+/- C)
Detector materials: X(Bait), Y(Prey)
Nano-assembly matrix-forming materials: N FIG. 9
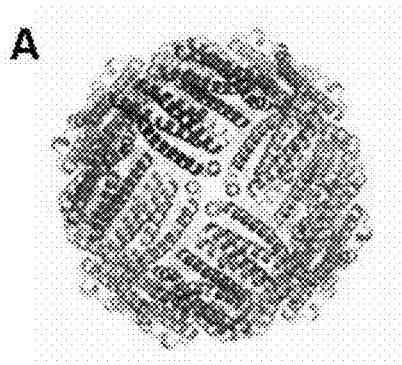
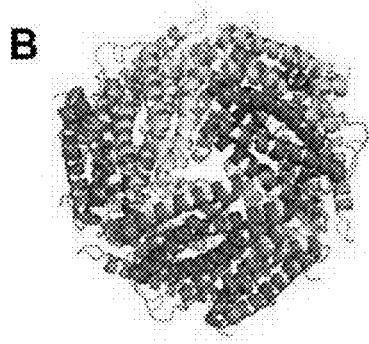

METHOD FOR QUANTITATIVELY SENSING AND EFFECTIVELY MARKING INTERACTION WITH TARGET MATERIAL BY USING ENERGY TRANSFER AND SIGNAL CHANGE BASED ON HIGH-DENSITY DISPLAY OF MATERIAL

CROSS-REFERENCE TO RELATED APPLICATIONS

This application is a U.S. national phase under the provisions of 35 U.S.C. §371 of International Patent Application No. PCT/KR12/06399 filed Aug. 10, 2012, which in turn claims priority of Korean Patent Application No. 10-2011-0079888 filed Aug. 10, 2011. The disclosures of such international patent application and Korean priority patent application are hereby incorporated herein by reference in their respective entireties, for all purposes.

TECHNICAL FIELD

The present invention relates to methods of quantitatively analyzing and detecting interactions, which effectively occur between detector materials displayed on a nano-assembly matrix at high density, and sensitively labeling and isolating a target material that effectively interacts with the detector materials, by the use of energy transfer and signal change that effectively occur in label molecules displayed at high density. Specifically, the present invention relates to a method of quantitatively detecting the interactions between various bioactive materials, which occur in vitro or in vivo, based on high-density displays of molecules, and to a method of sensitively labeling a target material that interacts with these bioactive materials.

BACKGROUND ART

In general, various physiological functions are regulated by the dynamic interactions between various bioactive molecules. If such interactions do not occur properly, problems arise to cause diseases. For example, proteins in vivo perform their functions by interaction with other proteins. Generally, two proteins having complementary structures interact with each other, and a bioactive compound interacts specifically with the specific portion of the three-dimensional protein structure. Generally, the interaction between two proteins strongly implies that they are functionally related. Furthermore, a bioactive compound interacting specifically with the specific portion of a disease-associated protein has potential as a therapeutic agent which can diagnose, prevent, treat or alleviate the disease by controlling the activity of the protein.

Accordingly, in the field of new drug development, there have been studies on various methods of detecting novel target proteins or screening bioactive molecules as drug candidates by detecting the interaction between a "bait" whose function and feature are known and a "prey" which is an interaction partner to be analyzed and detected. Thus, the identification and isolation of a novel target protein through the analysis of the interaction between bioactive molecules are considered as very important research projects for obtaining useful information about the activity, effectiveness and adverse effects of bioactive drugs. Additionally, target proteins promote the understanding of biological pathways and signal transduction systems and provide information on fundamental cellular regulation and disease mechanisms. Such information is a very powerful tool for developing new drugs, improving existing drugs and discovering the novel pharmaceutical use of existing drugs by analyzing and detecting bioactive compounds which interact with the target proteins.

Modern medicine faces the challenge of developing safer and more effective therapies against various human diseases. However, many drugs currently in use are prescribed by the biological effects in disease models without their target proteins and molecular targets (Burdine, L. et al., Chem. Biol. 11: 593, 2004). Bioactive natural products are an important source for drug development, but their modes of action are usually unknown (Clardy, J. et al., Nature 432: 829, 2004). Elucidation of their physiological targets and molecular targets is essential for understanding their therapeutic and adverse effects, thereby enabling the development of improved second-generation therapeutics. Moreover, the discovery of novel targets of clinically proven compounds may suggest new therapeutic applications (Ashburn, T. T. et al., Drug Discov. 3:673, 2004).

In chemical and biological field employing cell-based screening, "target screening" is used to identify small molecules with a desired phenotype from large compound libraries (Strausberg, R. L. at al., Science 300:294, 2003; Stockwell, B. R. Nature 432:846, 2004). Despite the great benefits of such screening, this approach has been hampered by the daunting task of target identification. However, the development of such identification technology is very important in various bioscience fields, including genomics, proteomics and system biology, because effective detection of diverse intracellular molecular interactions, including protein (or small molecule)-protein, is essential for understanding dynamic biological processes and regulatory networks.

In the field of target screening, several technologies, including affinity chromatography (Phizicky, E. M. et al., Microbiol. Rev. 59:94, 1995; Mendelsohn, A. R. et al., Science 284:1948, 1999), protein-small molecule microarray, phage display (Sche, P. P. et al., Chem. Biol. 6:707, 1999), yeast two-/three-hybrid assay (Licitra, E. J. et al., Proc. Natl. Acad. Sci. USA 93:12817, 1996), expression profiling, and parallel analysis (Zheng, O. et al., Chem. Biol. 11: 609, 2004) of yeast strains with heterologous deletions, have been utilized to analyze interactions between bioactive molecules.

However, such technologies all suffer from diverse problems, including high background, false positives, low sensitivity, inappropriate folding after protein expression, indirectness, lack of modification after protein expression, or limited target accessibility including cellular compatibility. In addition, the use of artificial experimental milieu, such as in vitro binding conditions or non-mammalian cells, sometimes causes errors in experimental results.

Accordingly, it is most preferable to directly examine the interaction between bioactive molecules in a state in which high sensitivity and selectivity were considered in physiological or pharmaceutical terms. Thus, it is considered that it is very important to develop the above-described base technology in order to offer various advantages over the prior art.

First, by probing the interactions between physiologically or pharmaceutically relevant bioactive materials and molecules, misleading outcomes produced by an artificial experimental setting can be greatly diminished. Second, it is possible to directly translate the interaction between bioactive molecules into a clear readout signal, unlike indirect readout methods that are dependent on overall expression profiles or complex biological phenotypes. Thus, intrinsic false positives/negatives or error-prone deductions about bioactive molecules and molecular targets can be obviated. Third, it is possible to perform dynamic, single-cell analysis for the interactions between bioactive materials and molecules. Dynamic analysis of individual living cells provides an effective method which can analyze intracellular processes occurring non-simultaneously among heterogeneous cells, over a broad range in physiological and pharmaceutical terms.

Therefore, the above-described base technology can be used to detect a variety of biological interactions between bioactive materials and molecules (e.g., interaction between a bioactive small molecule and a protein) and protein modifications (e.g., phosphorylation) within living cells in a broad range of tissues and disease states, but have many limitations. Thus, the development of new base technology is required.

Accordingly, the present inventors disclosed a method of investigating and verifying the dynamic interaction between various bioactive materials by analyzing whether this dynamic interaction results in nano-assembly matrix formation or co-localization on a nano-assembly matrix, by imaging (Korean Patent Laid-Open Publication No. 2009-0018585). This method is a qualitative method capable of investigating and verifying interactions by imaging using a microscope or the like.

Meanwhile, various physiological (assembly) matrices are present as signalsome in cells and as "-some" or "complex" such as exosome in an extracellular environment in vivo. It is known that bioactive materials, including one or more relevant proteins, are present in such physiological assembly matrices, and thus specific physiological functions in cells or in vivo are effectively regulated. It was found that multi/poly-valent interactions play a very important role in most physiological regulations, like in efficient physiological regulation mediated by such matrices (Mammen, M. et al., *Angew. Chem. Int. Ed.* 37:2755, 1998; Kiessling, L. L. et al., *Angew. Chem. Int. Ed.* 45:2348, 2006). In other words, multi/poly-valent interactions mainly play an important role in the interactions between most bioactive materials, including proteins, compared to mono-valent interactions.

Accordingly, the present inventors have conducted additional studies based on the high-density characteristic of such physiological matrices, and as a result, have developed novel methods capable of performing analysis and detection in a quantitative manner and detection and labeling in a more effective manner, deviating from a quantitative analysis method based on visual imaging. When energy transfer and signal change, which effectively occur between label molecules displayed on a nano-assembly matrix at high density, are measured, interactions between materials can be qualitatively and quantitatively measured and detected by, for example, a method including fluorescence analysis or FRET (fluorescence resonance energy transfer). In addition, when the efficiency of interactions between detector materials is increased by displaying the materials on a nano-assembly matrix at high density, the interactions between the materials can be qualitatively and quantitatively measured and detected in a more sensitive manner. Thus, there are advantages in that labeling is easy, interactions between materials can be individually identified in an easier manner by the quantitative analysis of energy signals using a method including flow cytometry or FACS (fluorescence associated cell sorting), and the high throughput of detection and analysis can be increased. The present inventors have found that a specific target material that efficiently interacts with detector materials displayed on a nano-assembly matrix at high density can be sensitively detected and labeled on the basis of such energy transfer or signal change, thereby completing the present invention.

The information disclosed in the Background Art section is only for the enhancement of understanding of the background of the present invention, and therefore may not contain information that forms a prior art that would already be known to a person of ordinary skill in the art.

DISCLOSURE OF INVENTION

Technical Problem

It is an object of the present invention to provide a novel method of sensitively labeling, isolating or identifying a target material that interacts with bioactive "bait" molecules displayed at high density. Another object of the present invention is to provide a method of quantitatively detecting and analyzing the interaction between a "bait" that is a bioactive material and a "prey" that is a bioactive material to be analyzed and detected, and a method of detecting a "prey" interacting with the "bait".

Still another object of the present invention is to provide a method of investigating and detecting a target material that blocks, inhibits, activates or induces the interaction between the "bait" and the "prey".

Technical Solution

To achieve the above objects, in one aspect, the present invention provides a method for labeling or isolating a target material interacting with a bait according to the present invention comprises the steps of:

(i) providing mediator (regulator) materials, bait materials and nano-assembly matrix-forming materials to the same field or system, wherein at least one of the mediator (regulator) material, the bait material and the nano-assembly material-forming material is labeled with a label;

(ii) forming a nano-assembly matrix by the interaction between the mediator (regulator) materials to display the bait materials at high density;

(iii) providing a library of prey materials to the nano-assembly matrix, labeling a prey material by interaction with the bait materials displayed on the nano-assembly matrix at high density, and selecting the labeled prey material as the target material; and (iv) confirming the labeled target material using the energy transfer or signal change, or isolating and identifying the confirmed target material.

The present invention also provides a method for labeling or isolating a target material interacting with a bait, the method comprising the steps of:

(i) providing first mediator (regulator) materials, second mediator (regulator) materials, bait materials and nano-assembly matrix-forming materials to the same field or system, wherein at least one of the mediator (regulator) material, the bait material and the nano-assembly material-forming material is labeled with a label;

(ii) forming a nano-assembly matrix by the interaction between the first mediator (regulator) materials and displaying the bait materials on the nano-assembly matrix at high density by the interaction between the second mediator (regulator) materials;

(iii) providing a library of prey materials to the nano-assembly matrix, labeling a prey material by interaction with the bait materials displayed on the nano-assembly matrix at high density, and selecting the labeled prey material as the target material; and (iv) confirming the labeled target material using the energy transfer or signal change, or isolating and identifying the confirmed target material.

The present invention also provides a method for labeling or isolating a target material interacting with a bait, the method comprising the steps of:

(i) providing bait materials and nano-assembly matrix-forming materials to the same field or system, wherein at least one of the bait material and the nano-assembly matrix-forming material is labeled with a label;

(ii) forming nano-assembly unit matrix to display the bait materials at high density;

(iii) providing a library of prey materials to the nano-assembly unit matrix, labeling a prey material bound by interaction with the bait materials displayed on the nano-assembly unit matrix, and selecting the labeled prey material as the target material, or forming a nano-assembly matrix from the nano-assembly unit matrix by mediator (regulator) materials, providing a library of prey materials to the formed nano-assembly matrix, labeling label a prey material bound by interaction with the bait materials displayed on the nano-assembly matrix at high density, and selecting the labeled prey material as the target material; and (iv) confirming the labeled target material using the energy transfer or signal change, or isolating and identifying the confirmed target material.

The present invention also provides a method for labeling or isolating a target material interacting with a bait, the method comprising the steps of:

(i) providing bait materials and nano-assembly matrix-forming materials to the same field or system, wherein at least one of the bait material and the nano-assembly matrix-forming material is labeled with a label;

(ii) forming a nano-assembly matrix by the interaction between the bait materials to display the bait materials at high density;

(iii) providing a library of prey materials to the nano-assembly matrix, labeling a prey material bound by interaction with the bait materials displayed on the nano-assembly matrix at high density, and selecting the labeled prey material as the target material; and (iv) confirming the labeled target material using the energy transfer or signal change, or isolating and identifying the confirmed target material.

The present invention also provides a method for labeling or isolating a target material interacting with a bait, the method comprising the steps of:

(i) providing bait materials having mediator (regulator) materials fused thereto and nano-assembly matrix-forming materials to the same field or system, wherein at least one of the mediator (regulator) material, the bait material and the nano-assembly material-forming material is labeled with a label;

(ii) forming a nano-assembly matrix by the interaction between the mediator (regulator) materials to display the bait materials at high density;

(iii) providing a library of prey materials to the nano-assembly matrix, labeling a prey material bound by interaction with the bait materials displayed on the nano-assembly matrix at high density, and selecting the labeled prey material as the target material; and (iv) confirming the labeled target material using the energy transfer or signal change, or isolating and identifying the confirmed target material.

The present invention also provides a method for isolating a target material interacting with a bait, the method comprising the steps of:

(i) providing mediator (regulator) materials, bait materials and nano-assembly matrix-forming materials to the same field or system, wherein at least one of the mediator (regulator) material, the bait material and the nano-assembly material-forming material is labeled with a label;

(ii) forming a nano-assembly matrix by the interaction between the mediator (regulator) materials to display the bait materials at high density; and (iii) providing a library of prey materials, and isolating and identifying, as the target material, a prey material that interacted with the bait materials.

The present invention also provides a method for isolating a target material interacting with a bait, the method comprising the steps of:

(i) providing first mediator (regulator) materials, second mediator (regulator) materials, bait materials and nano-assembly matrix-forming materials to the same field or system, wherein at least one of the mediator (regulator) material, the bait material and the nano-assembly material-forming material is labeled with a label;

(ii) forming a nano-assembly matrix by the interaction between the first mediator (regulator) materials, and displaying the bait materials on the nano-assembly matrix at high density by the interaction between the second mediator (regulator) materials; and (iii) providing a library of prey materials, and isolating and identifying, as the target material, a prey material that interacted with the bait materials.

The present invention also provides a method for isolating a target material interacting with a bait, the method comprising the steps of:

(i) providing bait materials and nano-assembly matrix-forming materials to the same field or system, wherein at least one of the bait material and the nano-assembly matrix-forming material is labeled with a label;

(ii) forming nano-assembly unit matrix to display the bait materials at high density; and (iii) providing a library of prey materials to the nano-assembly unit matrix, and isolating and identifying, as the target material, a prey material that interacted with the bait materials, or forming a nano-assembly matrix from the nano-assembly unit matrix by mediator (regulator) materials, providing a library of prey materials to the formed nano-assembly matrix, and isolating and identifying, as the target material, a prey material that interacted with the bait materials.

The present invention also provides a method for isolating a target material interacting with a bait, the method comprising the steps of:

(i) providing bait materials and nano-assembly matrix-forming materials to the same field or system, wherein at least one of the bait material and the nano-assembly matrix-forming material is labeled with a label;

(ii) forming a nano-assembly matrix by the interaction between the bait materials to display the bait materials at high density; and (iii) providing a library of prey materials to the nano-assembly matrix, and isolating and identifying, as the target material, a prey material that interacted with the bait materials.

The present invention also provides a method for isolating a target material interacting with a bait, the method comprising the steps of:

(i) providing bait materials having mediator (regulator) materials fused thereto and nano-assembly matrix-forming materials to the same field or system, wherein at least one of the mediator (regulator) material, the bait material and the nano-assembly material-forming material is labeled with a label;

(ii) forming a nano-assembly matrix by the interaction between the mediator (regulator) materials to display the bait materials at high density; and (iii) providing a library of prey materials to the nano-assembly matrix, and isolating and identifying, as the target material, a prey material that interacted with the bait materials.

The present invention also provides a method for detecting a target material interacting with a bait, the method comprising the steps of:

(i) providing mediator (regulator) materials, bait materials and nano-assembly matrix-forming materials to the same field or system;

(ii) forming a nano-assembly matrix by the interaction between the mediator (regulator) materials to display the bait materials at high density;

(iii) providing a library of prey materials to the nano-assembly matrix; and (iv) measuring the energy transfer or signal change to detect the interaction between the bait material and the prey material, wherein at least one of the mediator (regulator) material, the bait material, the nano-assembly material-forming material and the library of prey materials is labeled with a label.

The present invention also provides a method for detecting a target material interacting with a bait, the method comprising the steps of:

(i) providing first mediator (regulator) materials, second mediator (regulator) materials, bait materials and nano-assembly matrix-forming materials to the same field or system;

(ii) forming a nano-assembly matrix by the interaction between the first mediator (regulator) materials, and displaying the bait materials on the nano-assembly matrix at high density by the interaction between the second mediator (regulator) materials;

(iii) providing a library of prey materials to the nano-assembly matrix; and (iv) measuring the energy transfer or signal change to detect the interaction between the bait material and the prey material, wherein at least one of the mediator (regulator) material, the bait material, the nano-assembly material-forming material and the library of prey materials is labeled with a label.

The present invention also provides a method for detecting a target material interacting with a bait, the method comprising the steps of:

(i) providing bait materials and nano-assembly matrix-forming materials to the same field or system;

(ii) forming nano-assembly unit matrix to display the bait materials at high density;

(iii) providing a library of prey materials to the nano-assembly unit matrix; and (iv) measuring the energy transfer or signal change to detect the interaction between the bait material and the prey material, wherein at least one of the bait material, the nano-assembly material-forming material and the library of prey materials is labeled with a label.

The present invention also provides a method for detecting a target material interacting with a bait, the method comprising the steps of:

(i) providing bait materials and nano-assembly matrix-forming materials to the same field or system;

(ii) forming a nano-assembly matrix by the interaction between the bait materials to display the bait materials at high density;

(iii) providing a library of prey materials to the nano-assembly matrix; and (iv) measuring the energy transfer or signal change to detect the interaction between the bait material and the prey material, wherein at least one of the bait material, the nano-assembly material-forming material and the library of prey materials is labeled with a label.

The present invention also provides a method for detecting a target material interacting with a bait, the method comprising the steps of:

(i) providing bait materials having mediator (regulator) materials fused thereto and nano-assembly matrix-forming materials to the same field or system;

(ii) forming a nano-assembly matrix by the interaction between the mediator (regulator) materials to display the bait materials at high density;

(iii) providing a library of prey materials to the nano-assembly matrix; and (iv) measuring the energy transfer or signal change to detect the interaction between the bait material and the prey material, wherein at least one of the bait material, the nano-assembly material-forming material and the library of prey materials is labeled with a label.

The present invention also provides a method for detecting a target material interacting with a bait, the method comprising the steps of:

(i) providing bait materials, nano-assembly matrix-forming materials and a library of prey materials to the same field or system;

(ii) reacting the bait materials with the prey materials so that a nano-assembly matrix is formed to display the bait materials and the prey materials at high density; and (iii) measuring the energy transfer or signal change to detect the interaction between the bait materials and the prey materials, wherein at least one of the bait material, the nano-assembly material-forming material and the library of prey materials is labeled with a label.

The present invention also provides a method for detecting or quantifying the interaction between materials, the method comprising the steps of:

(i) providing mediator (regulator) materials, bait materials and nano-assembly matrix-forming materials to the same field or system;

(ii) forming a nano-assembly matrix by the interaction between the mediator (regulator) materials to display the bait materials at high density;

(iii) providing prey materials to the nano-assembly matrix; and (iv) measuring the energy transfer or signal change to detect or quantify the interaction between the bait materials and the prey materials, wherein at least one of the mediator (regulator) material, the bait material, the nano-assembly material-forming material and the prey material is labeled with a label.

The present invention also provides a method for detecting or quantifying the interaction between materials, the method comprising the steps of:

(i) providing first mediator (regulator) materials, second mediator (regulator) materials, bait materials and nano-assembly matrix-forming materials to the same field or system;

(ii) forming a nano-assembly matrix by the interaction between the first mediator (regulator) materials and displaying the bait materials on the nano-assembly matrix at high density by the interaction between the second mediator (regulator) materials;

(iii) providing prey materials to the nano-assembly matrix; and (iv) measuring the energy transfer or signal change to detect or quantify the interaction between the bait materials and the prey materials, wherein at least one of the mediator (regulator) material, the bait material, the nano-assembly material-forming material and the prey material is labeled with a label.

The present invention also provides a method for detecting or quantifying the interaction between materials, the method comprising the steps of:

(i) providing bait materials and nano-assembly matrix-forming materials to the same field or system;

(ii) forming nano-assembly unit matrix to display the bait materials at high density;

(iii) providing prey materials to the nano-assembly unit matrix; and (iv) measuring the energy transfer or signal change to detect or quantify the interaction between the bait materials and the prey materials, wherein at least one of the bait material, the nano-assembly material-forming material and the prey material is labeled with a label.

The present invention also provides a method for detecting or quantifying the interaction between materials, the method comprising the steps of:

(i) providing bait materials and nano-assembly matrix-forming materials to the same field or system;

(ii) forming a nano-assembly matrix by the interaction between the bait materials to display the bait materials at high density;

(iii) providing prey materials to the nano-assembly matrix; and (iv) measuring the energy transfer or signal change to detect or quantify the interaction between the bait materials and the prey materials, wherein at least one of the bait material, the nano-assembly material-forming material and the prey material is labeled with a label. (claim 38)

The present invention also provides a method for detecting or quantifying the interaction between materials according to the present invention comprises the steps of:

(i) providing bait materials having mediator (regulator) materials fused thereto and nano-assembly matrix-forming materials to the same field or system;

(ii) forming a nano-assembly matrix by the interaction between the mediator (regulator) materials to display the bait materials at high density;

(iii) providing prey materials to the nano-assembly matrix; and (iv) measuring the energy transfer or signal change to detect or quantify the interaction between the bait materials and the prey materials, wherein at least one of the bait material, the nano-assembly material-forming material and the prey material is labeled with a label.

The present invention also provides a method for detecting or quantifying the interaction between materials, the method comprising the steps of:

(i) providing bait materials, prey materials and nano-assembly matrix-forming materials to the same field or system;

(ii) reacting the bait materials with the prey materials so that a nano-assembly matrix is formed to display the bait materials and the prey materials at high density; and (iv) measuring the energy transfer or signal change to detect or quantify the interaction between the bait materials and the prey materials, wherein at least one of the bait material, the nano-assembly material-forming material and the prey material is labeled with a label.

The present invention also provides a composition for disease-related targeting, imaging or diagnosis, the composition comprising a nano-assembly matrix isolated by a method comprising the steps of:

(i) providing mediator (regulator) molecules, bait molecules and a nano-assembly matrix-forming material to the same field or system; and (ii) forming a nano-assembly matrix by the interaction between the mediator (regulator) molecules to display the bait molecules at high density, and isolating the formed nano-assembly matrix.

The present invention also provides a composition for disease-related targeting, imaging or diagnosis, the composition comprising a nano-assembly matrix isolated by a method comprising the steps of:

(i) providing first mediator (regulator) molecules, second mediator (regulator) molecules, bait molecules, and a nano-assembly matrix-forming material to the same field or system; and (ii) forming a nano-assembly matrix by the interaction between the first mediator (regulator) molecules, displaying the bait molecules at high density by the interaction between the second mediator (regulator) molecules, and isolating the formed nano-assembly matrix.

The present invention also provides a composition for disease-related targeting, imaging or diagnosis, the composition comprising a nano-assembly matrix isolated by a method comprising the steps of:

(i) providing bait molecules and a nano-assembly matrix-forming material to the same field or system; and (ii) forming a nano-assembly matrix, displaying the bait molecules on the formed nano-assembly matrix at high density, and isolating the formed nano-assembly matrix.

The present invention also provides a composition for disease-related targeting, imaging or diagnosis, the composition comprising a nano-assembly matrix isolated by a method comprising the steps of:

(i) providing mediator (regulator) molecules, bait molecules and a nano-assembly matrix-forming material to the same field or system; and (ii) displaying the mediator (regulator) molecules and the bait molecules on the nano-assembly matrix at high density, and isolating the formed nano-assembly matrix.

The present invention also provides a composition for disease-related targeting, imaging or diagnosis, the composition comprising a nano-assembly matrix isolated by a method comprising the steps of:

(i) providing bait molecules and a nano-assembly matrix-forming material to the same field or system; and (ii) displaying the mediator (regulator) molecules on the nano-assembly matrix at high density, and isolating the formed nano-assembly matrix.

The present invention also provides a composition for disease-related targeting, imaging or diagnosis, the composition comprising a nano-assembly matrix isolated by a method comprising the steps of:

(i) providing bait molecules and a nano-assembly matrix-forming material to the same field or system; and (ii) forming a nano-assembly matrix by the interaction between the bait molecules to display the bait molecules at high density, and isolating the formed nano-assembly matrix.

The present invention also provides a composition for disease-related targeting, imaging or diagnosis, the composition comprising a nano-assembly matrix isolated by a method comprising the steps of:

(i) providing bait materials having mediator (regulator) materials fused thereto and nano-assembly matrix-forming materials to the same field or system (ii) forming a nano-assembly matrix by the interaction between the mediator (regulator) materials to display the bait materials at high density, and isolating the formed nano-assembly matrix.

The present invention also provides a method for targeting, imaging or diagnosing a disease related to a target material that interacts with a bait, the method comprising the steps of:

(i) providing mediator (regulator) materials, bait materials and a nano-assembly matrix-forming material to the same field or system, wherein one or more of the bait material and the nano-assembly matrix-forming material is labeled with a label;

(ii) forming a nano-assembly matrix by the interaction between the mediator (regulator) materials to display the bait materials at high density, and isolating the formed nano-assembly matrix;

(iii) introducing the isolated nano-assembly matrix into a cell, a tissue or a living body and reacting the introduced nano-assembly matrix with a prey library; and (iv) labeling a prey material bound by interaction with the bait materials displayed on the nano-assembly matrix at high density, selecting the labeled prey material as the target material, and measuring the energy transfer or signal change in the labeled prey material, thereby targeting, imaging or diagnosing the disease.

The present invention also provides a method for targeting, imaging or diagnosing a disease related to a target material that interacts with a bait, the method comprising the steps of: introducing the isolated nano-assembly matrix or nano matrices into a cell, a tissue or a living body and reacting the introduced nano-assembly matrix with a prey library; and labeling a prey material bound by interaction with the bait materials and/or mediator (regulator) materials displayed on the nano-assembly matrix at high density, selecting the labeled prey material as the target material, and measuring the energy transfer or signal change in the labeled prey material, thereby targeting, imaging or diagnosing the disease.

The present invention also provides a method for screening a target material that inhibits or activates the interaction between bait materials and prey materials comprises the steps of:

(i) providing mediator (regulator) materials, bait materials and nano-assembly matrix-forming materials to the same field or system, and forming a nano-assembly matrix by the interaction between the mediator (regulator) materials to display the bait materials at high density;

(ii) providing prey materials to the formed nano-assembly matrix in the presence of target candidates; and (iii) selecting, as a target blocker material or a target activator material, a target candidate corresponding to a case in which the energy transfer or signal change in the presence of the target candidate is reduced (inhibited) or increased (activated) compared to the energy transfer or signal change in the absence of the target candidate, wherein at least one of the mediator (regulator) material, the bait material, the nano-assembly material-forming material and the prey material is labeled with a label.

The present invention also provides a method for screening a target material that inhibits or activates the interaction between bait materials and prey materials comprises the steps of:

(i) providing first mediator (regulator) materials, second mediator (regulator) materials, bait materials and nano-assembly matrix-forming materials to the same field or system, forming a nano-assembly matrix by the interaction between the first mediator (regulator) materials, and displaying the bait materials on the nano-assembly matrix at high density by the interaction between the second mediator (regulator) materials;

(ii) providing prey materials to the formed nano-assembly matrix in the presence of target candidates; and (iii) selecting, as a target blocker material or a target activator material, a target candidate corresponding to a case in which the energy transfer or signal change in the presence of the target candidate is reduced (inhibited) or increased (activated) compared to the energy transfer or signal change in the absence of the target candidate, wherein at least one of the mediator (regulator) material, the bait material, the nano-assembly material-forming material and the prey material is labeled with a label.

The present invention also provides a method for screening a target material that inhibits or activates the interaction between bait materials and prey materials comprises the steps of:

(i) providing bait materials, prey materials and nano-assembly matrix-forming materials to the same field or system in the presence of target candidates to display the bait materials on a nano-assembly unit matrix at high density; and (ii) selecting, as a target blocker material or a target activator material, a target candidate corresponding to a case in which the energy transfer or signal change in the presence of the target candidate is reduced (inhibited) or increased (activated) compared to the energy transfer or signal change in the absence of the target candidate, wherein at least one of the bait material, the nano-assembly material-forming material and the prey material is labeled with a label.

The present invention also provides a method for screening a target material that inhibits or activates the interaction between bait materials and prey materials comprises the steps of:

(i) providing bait materials and nano-assembly matrix-forming materials to the same field or system, and forming a nano-assembly matrix by the interaction between the bait materials to display bait materials at high density;

(ii) providing prey materials to the formed nano-assembly matrix in the presence of target candidates; and (iii) selecting, as a target blocker material or a target activator material, a target candidate corresponding to a case in which the energy transfer or signal change in the presence of the target candidate is reduced (inhibited) or increased (activated) compared to the energy transfer or signal change in the absence of the target candidate, wherein at least one of the mediator (regulator) material, the bait material, the nano-assembly material-forming material and the prey material is labeled with a label.

The present invention also provides a method for screening a target material that inhibits or activates the interaction between bait materials and prey materials comprises the steps of:

(i) providing bait materials having mediator (regulator) materials bound thereto and nano-assembly matrix-forming materials to the same field or system, and forming a nano-assembly matrix by the interaction between the mediator (regulator) materials to display bait materials at high density;

(ii) providing prey materials to the formed nano-assembly matrix in the presence of target candidates; and (iii) selecting, as a target blocker material or a target activator material, a target candidate corresponding to a case in which the energy transfer or signal change in the presence of the target candidate is reduced (inhibited) or increased (activated) compared to the energy transfer or signal change in the absence of the target candidate, wherein at least one of the mediator (regulator) material, the bait material, the nano-assembly material-forming material and the prey material is labeled with a label.

The present invention also provides a method for screening a target material that inhibits or activates the interaction between bait materials and prey materials comprises the steps of:

(i) providing bait materials, prey materials and nano-assembly matrix-forming materials to the same field or system, wherein at least one of the bait material, the prey material and the nano-assembly matrix-forming material is labeled with a label;

(ii) reacting the bait materials with the prey materials in the presence of target candidates so that a nano-assembly matrix is formed to display the bait materials and the prey materials at high density; and (iii) selecting, as a target blocker material or a target activator material, a target candidate corresponding to a case in which the energy transfer or signal change in the presence of the target candidate is reduced (inhibited) or increased (activated) compared to the energy transfer or signal change in the absence of the target candidate.

Other features and embodiments of the present invention will be more apparent from the following detailed descriptions and the appended claims.

BRIEF DESCRIPTION OF THE DRAWINGS

In FIG. 1, A, B, C, X and Y are the same or different materials, and N is a nano-assembly matrix-forming material. One or more materials of N, X, Y, A, B and C are labeled with a label, and the energy transfer or signal change caused by the interaction between detector materials are measured.

In FIG. 2, A, B, C, D, E, F, X and Y are the same or different materials, and N is a nano-assembly matrix-forming material. One or more materials of N, X, Y, A, B, C, D, E and F are labeled with a label, and the energy transfer or signal change caused by the interaction between detector materials are measured.

FIGS. 3(A) and 3(B) are schematic views showing constructs for detecting the direct interaction between X and Y or the indirect interaction through A in a nano-assembly matrix. In FIG. 3, X, Y and A are the same or different materials, and N is a nano-assembly matrix-forming material. One or more materials of N, X, Y and A are labeled with a label, and the energy transfer or signal change caused by the interaction between detector materials are measured.

FIGS. 4(A), 4(B) and 4(C) are schematic views showing constructs for detecting an interaction with Y, in which formation of a nano-assembly matrix is induced by the direct interaction between X and X or X' or the indirect interaction through A. In FIG. 4, X, X' and A are the same or different materials, and N and N' are nano-assembly matrix-forming materials. In FIG. 4(A), the same nano-assembly matrix-forming materials are used, in FIG. 4(B), different nano-assembly matrix-forming materials are used, and in FIG. 4(C), the same bait materials are used. One or more materials of N, X, X' and A are labeled with a label, and the energy transfer or signal change caused by the interaction between detector materials are measured.

FIGS. 5(A), 5(B) and 5(C) are schematic views showing constructs for detecting an interaction with Y, in which formation of a nano-assembly matrix is induced by the indirect interaction between X or X and X' through the mediator (regulator) materials A and B or A, B and C bound to the detector materials. In FIG. 5, X, X', A, B and C are the same or different materials, and N and N' are nano-assembly matrix-forming materials. In FIG. 5(A), the same nano-assembly matrix-forming materials are used, in FIG. 5(B), different nano-assembly matrix-forming materials are used, and in FIG. 5(C), the same bait materials are used. One or more materials of N, X, X', A, B and C are labeled with a label, and the energy transfer or signal change caused by the interaction between detector materials are measured.

FIGS. 6(A) and 6(B) are schematic views showing constructs for detecting the direct interaction between X and Y or the indirect interaction through A in a nano-assembly matrix. In FIG. 6, X, Y and A are the same or different materials, and N and N' are nano-assembly matrix-forming materials. In FIG. 6(A), the same nano-assembly matrix-forming materials are used, and in FIG. 6(B), different nano-assembly matrix-forming materials are used. One or more materials of N, X, Y and A are labeled with a label, and the energy transfer or signal change caused by the interaction between detector materials are measured.

FIGS. 7(A) and 7(B) are schematic views showing constructs for detecting the interaction between X and Y in a nano-assembly matrix when the direct interaction between A and B or the indirect interaction through C occur. In FIG. 7, A, B, C, X and Y are the same or different materials, and N and N' are nano-assembly matrix-forming materials. In FIG. 7(A), the same nano-assembly matrix-forming materials are used, and in FIG. 7(B), different nano-assembly matrix-forming materials are used. One or more materials of N, X, Y, A, B and C are labeled with a label, and the energy transfer or signal change caused by the interaction between detector materials are measured.

FIGS. 8(A) and 8(B) are schematic views showing constructs for detecting the interaction between X and Y in a nano-assembly matrix when the direct interaction between A and B or the indirect interaction through C occur.

In FIG. 8, A, B, C, X and Y are the same or different materials, and N and N' are nano-assembly matrix-forming materials. In FIG. 8(A), X materials does not interact with each other, and FIG. 8(B), X materials interacts interact with each other. One or more materials of N, X, Y, A, B and C are labeled with a label, and the energy transfer or signal change caused by the interaction between detector materials are measured.

FIGS. 9(A) and 9(B) show the structure of nano-sized unit matrices formed by self-assembly of ferritin or DPS protein.

BEST MODE FOR CARRYING OUT THE INVENTION

Figure 1:
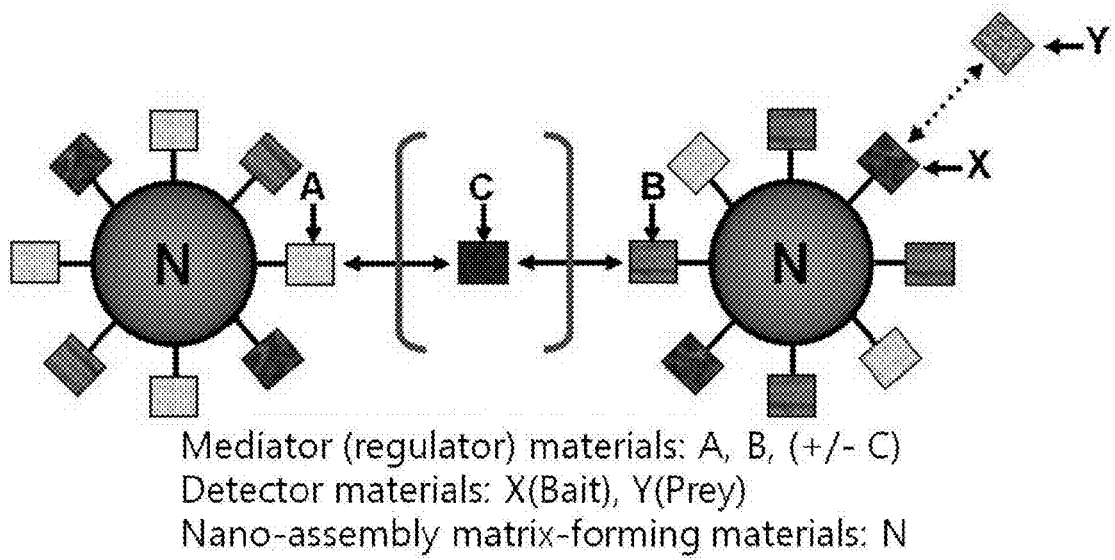
FIG. 1 is a schematic view showing a construct for detecting the interaction between X and Y in a nano-assembly matrix when formation of the nano-assembly matrix is induced by the direct interaction between mediator (regulator) materials A and B or by the indirect interaction through C.

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

The definition of major terms used in the present invention is as follows.

As used herein, the term "bioactive compound" means a compound which binds to biomolecules including proteins, nucleic acids, saccharides or lipids in vivo to regulate the function or activity of the biomolecules. Such a bioactive compound is extracted from an organism or prepared by chemical synthesis. Various antibiotics, for example, "Cyclosporine A" (Novartis AG) and "FK506" (Fujisawa), which are used to reduce immune rejection following an organ transplantation, were isolated from microorganisms, plants or marine organisms. Such a natural or synthetic bioactive compound is developed as a new drug, after it is tested for its pharmacological activity and is subjected to clinical tests using an animal model and a human model.

As used herein, the term "bioactive material or molecule" can be defined as a material which performs regulatory functions, such as promoting or inhibiting the function of the organism's body during the life of organisms. Such a bioactive material can be obtained from natural products such as animals or plants or extracted or purified from the metabolites of microbial, animal and plant cell lines. Moreover, it can also be obtained by chemical synthesis. Examples of the bioactive material include nucleic acids, nucleotides, proteins, peptides, amino acids, saccharides, lipids, vitamins, and chemical compounds.

As used herein, the term "bait material or molecule" refers to a bioactive molecule which is used to detect interactions with other bioactive molecules.

As used herein, the term "prey material or molecule" refers to a bioactive molecule to be probed (analyzed) or detected, which is an interaction partner for the "bait".

As used herein, the term "target material" refers to a material to be detected. According to intended use, the target molecule may be the prey that interacts with the bait. Also, the target material may be a material which activates, induces, blocks or inhibits the interactions between the bait and the prey. Namely, the target materials include all the materials to be identified. Among them, a material which blocks or inhibits the interaction between the bait and the prey is defined as a "blocker material", and a material which activates or induces the interactions thereof is defined as an "activator material".

As used herein, the term "regulator material or molecule" refers to a material which is related directly or indirectly to or interacts with a material that mediates an intracellular function to be regulated. According to the intended use, the regulator material may be either a detector material or a material that binds to and interacts with a detector material. In addition, a material that activates, induces, blocks or inhibits an intracellular function to be mediated by a detector material or a mediator (regulator) may also be used as the regulator material.

As used herein, the term "nano-assembly matrix" refers a high-density larger matrix, which is formed by the interaction of nano-assembly unit matrix having a specific structural framework and can be readily observed. For example, the nano-assembly matrix is a large matrix formed by the interaction of nano-assembly unit matrix having a specific structural framework, formed by self-assembly of 24 sub-units of a protein such as ferritin. In the present invention, the nano-assembly matrix is used in the same sense as an amplified high-signal-intensity dotted image pattern that can be readily observed. In the art to which the present invention pertains, the terms "nanoclusters" and "nanoassemblies" are used in the same sense as the nano-assembly matrix. In an embodiment of the present invention, a high-density matrix of nano-assembly unit matrix, formed by the interaction between detector materials or between mediator (regulator) materials, is referred to as the formation of the nano-assembly matrix. The formation of the nano-assembly matrix can be confirmed by the energy transfer or signal change. In addition, it can also be confirmed by a change in a dotted image pattern having a high signal intensity.

In the present invention, the term "energy transfer or signal change" includes changes in the intensity and pattern (e.g., the number, area, intensity and distribution appearing in image patterns such as dotted patterns) of images appearing in label materials (fluorescent material, luminescent material, magnetic material, enzymatic material for ELISA, or radioactive material) displayed or indirectly on a nano (assembly) matrix at high density directly and also changes in the intensity and pattern (e.g., the number, width, area, height and distribution of pulses in flow cytometry) of signals. In addition, the term includes energy generated from such label materials by resonance, and the various changes in intensity and pattern of images and signals caused by energy transfer, transfer, interference and quenching. Thus, it includes energy signal transfer and various signal changes, which occur in a label or between label molecules displayed at high density.

As used herein, the expression "nano-assembly matrix-forming material" refers to any material having the property and function of forming the nano-assembly matrix. For example, the term means a poly/multi-valent material such as ferritin, which has a plurality of the same or different binding moieties and can form an assembly by interaction or self-assembly. In the present invention, the term means a material that forms either an observable high-signal-intensity dotted image pattern by the interaction between the mediator (regulator) molecules or a nano-assembly matrix (i.e., observable high-signal-intensity dotted image pattern) by the interaction between the detector materials.

As used herein, the term "nano-assembly unit matrix" or "nano-assembly particle" or "nano-assembly multimeric complex" refers to matrices on which the nano-assembly matrix is based and which are formed by self-assembly of protein or the like. For example, 24 subunits of ferritin protein are self-assembled to form a nano-assembly unit matrix.

As used herein, the term "mediator (regulator) material" refers to a material inducing the formation of the nano-assembly matrix. This is meant to include all materials capable of inducing the formation of the nano-assembly matrix through direct or indirect binding, interaction or fusion with the nano-assembly matrix-forming material. A material that mediates or regulates the activity of the mediator (regulator) material may also be defined as a mediator (regulator) material in a broad sense. The mediator (regulator) molecules include not only specific compounds or proteins, which induce the formation of the nano-assembly matrix, but also phenomena such as specific mutations, and specific physiological signals. For example, the formation of the nano-assembly matrix can be induced through the interactions between proteins resulting from physiological signals, the interactions between RNA and protein, the use of a specific mutation of a specific protein, or the use of a protein interacting only with a specific compound, and such phenomena and signals are referred to as "mediator (regulator) materials" in the specification of the present invention.

As used herein, the term "label" refers to a magnetic material, an enzyme for ELISA, a radioactive material, a fluorescent material, a luminescent material or the like, which serves to detect signals and is bound materials, including a nano-assembly matrix-forming, a bait material, a prey material, a mediator (regulator) material, a target material and the like. In addition, the label also includes label inhibitors such as gold particles, which quench radioactive materials, fluorescent materials or luminescent materials, and in this case, the reduction or disappearance of signals by interactions can be detected. These materials are collectively referred to as the "label" in the specification.

As used herein, the term "display" is meant to include exposing a material directly to the inside or the outside of a nano-assembly unit matrix or a nano-assembly matrix, or exposing the material indirectly through another material, or loading a material into a nano-assembly unit matrix or a nano-assembly matrix.

Hereinafter, the present invention will be described in further detail.

In one aspect, the present invention is directed to a method for labeling or isolating a target material ("prey") that interacts with a specific material "bait" (e.g., a specific bioactive material) in vitro or in vivo.

Specifically, a first method for labeling or isolating a target material interacting with a bait according to the present invention comprises the steps of:

(i) providing mediator (regulator) materials, bait materials and nano-assembly matrix-forming materials to the same field or system, wherein at least one of the mediator (regulator) material, the bait material and the nano-assembly material-forming material is labeled with a label;

(ii) forming a nano-assembly matrix by the interaction between the mediator (regulator) materials to display the bait materials at high density;

(iii) providing a library of prey materials to the nano-assembly matrix, labeling a prey material by interaction with the bait materials displayed on the nano-assembly matrix at high density, and selecting the labeled prey material as the target material; and (iv) confirming the labeled target material using the energy transfer or signal change, or isolating and identifying the confirmed target material.

A second method for labeling or isolating a target material interacting with a bait according to the present invention comprises the steps of:

(i) providing first mediator (regulator) materials, second mediator (regulator) materials, bait materials and nano-assembly matrix-forming materials to the same field or system, wherein at least one of the mediator (regulator) material, the bait material and the nano-assembly material-forming material is labeled with a label;

(ii) forming a nano-assembly matrix by the interaction between the first mediator (regulator) materials and displaying the bait materials on the nano-assembly matrix at high density by the interaction between the second mediator (regulator) materials;

(iii) providing a library of prey materials to the nano-assembly matrix, labeling a prey material by interaction with the bait materials displayed on the nano-assembly matrix at high density, and selecting the labeled prey material as the target material; and (iv) confirming the labeled target material using the energy transfer or signal change, or isolating and identifying the confirmed target material.

In the first and second methods of the present invention, after the nano-assembly matrix is formed by the mediator (regulator) materials, the prey material that interacts with the bait materials displayed on the formed nano-assembly matrix at high density can be labeled, isolated or identified.

FIG. 1 is a schematic view showing the first method of the present invention, i.e., a construct for detecting the interaction between X and Y in a nano-assembly matrix when formation of the nano-assembly matrix is induced by the direct interaction between mediator (regulator) materials A and B or by the indirect interaction through C wherein A, B, C, X and Y are the same or different materials, and N is a nano-assembly matrix-forming material. As shown in FIG. 1, a nano-assembly matrix is formed by the interaction between mediator (regulator) materials bound to nano-assembly matrix-forming materials, and bait materials bound to the nano-assembly matrix-forming materials are displayed on the formed nano-assembly matrix at high density. In FIG. 1, one or more materials of N, X, Y, A, B and C are labeled with a label, and the energy transfer or signal change caused by the interaction between detector materials are measured.

Figure 2:
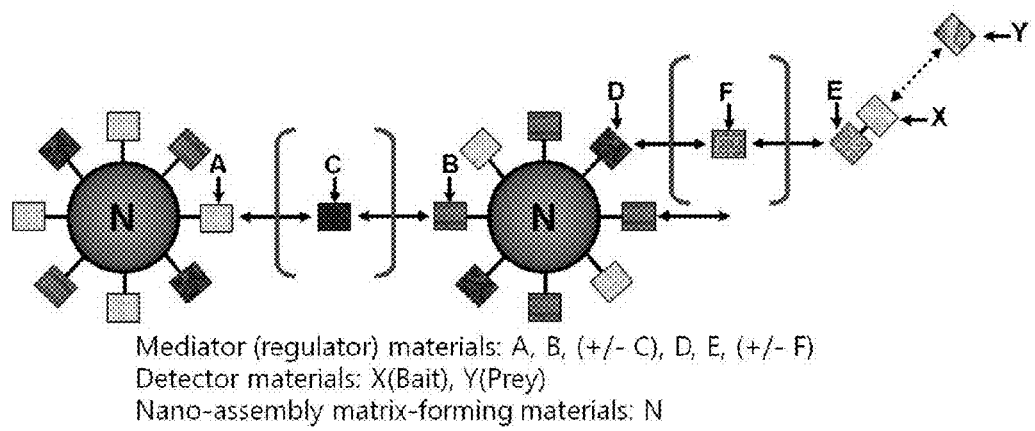
FIG. 2 is a schematic view showing a construct for detecting the interaction between X and Y when formation of a nano-assembly matrix is induced by the interaction between the first mediator (regulator) materials A, B and C while the detector material X is bound to the formed nano-assembly matrix by the interaction between the second mediator (regulator) materials D, E and F.

FIG. 2 is a schematic view showing the second method of the present invention, i.e., a construct for detecting the interaction between X and Y when formation of a nano-assembly matrix is induced by the interaction between the first mediator (regulator) materials A, B and C while the detector material X is bound to the formed nano-assembly matrix by the interaction between the second mediator (regulator) materials D, E and F wherein A, B, C, D, E, F, X and Y are the same or different materials, and N is a nano-assembly matrix-forming material. As shown in FIG. 2, a nano-assembly matrix is formed either by the direct interaction between first mediator (regulator) materials bound to the nano-assembly matrix-forming materials or by the indirect interaction through the material C, and bait materials X bound thereto by second mediator materials E are displayed on the nano-assembly matrix at high density. In FIG. 1, one or more materials of N, X, Y, A, B, C, D, E and F are labeled with a label, and the energy transfer or signal change caused by the interaction between detector materials are measured.

A third method for labeling or isolating a target material interacting with a bait according to the present invention comprises the steps of:

(i) providing bait materials and nano-assembly matrix-forming materials to the same field or system, wherein at least one of the bait material and the nano-assembly matrix-forming material is labeled with a label;

(ii) forming nano-assembly unit matrix to display the bait materials at high density;

(iii) providing a library of prey materials to the nano-assembly unit matrix, labeling a prey material bound by interaction with the bait materials displayed on the nano-assembly unit matrix, and selecting the labeled prey material as the target material, or forming a nano-assembly matrix from the nano-assembly unit matrix by mediator (regulator) materials, providing a library of prey materials to the formed nano-assembly matrix, labeling a prey material bound by interaction with the bait materials displayed on the nano-assembly matrix at high density, and selecting the labeled prey material as the target material; and (iv) confirming the labeled target material using the energy transfer or signal change, or isolating and identifying the confirmed target material.

FIG. 3 is a schematic view showing the third method of the present invention, i.e., constructs for detecting the direct interaction between X and Y or the indirect interaction through A in a nano-assembly matrix wherein X, Y and A are the same or different materials, and N is a nano-assembly matrix-forming material. As shown in FIG. 3, bait materials bound to nano-assembly matrix-forming materials form a nano-assembly matrix by self-assembly of the nano-assembly matrix-forming materials, and thus are displayed on the nano-assembly matrix at high density. In FIG. 3, one or more materials of N, X, Y and A are labeled with a label, and the energy transfer or signal change caused by the interaction between detector materials are measured.

A fourth method for labeling or isolating a target material interacting with a bait according to the present invention comprises the steps of:

(i) providing bait materials and nano-assembly matrix-forming materials to the same field or system, wherein at least one of the bait material and the nano-assembly matrix-forming material is labeled with a label;

(ii) forming a nano-assembly matrix by the interaction between the bait materials to display the bait materials at high density;

(iii) providing a library of prey materials to the nano-assembly matrix, labeling a prey material bound by interaction with the bait materials displayed on the nano-assembly matrix at high density, and selecting the labeled prey material as the target material; and (iv) confirming the labeled target material using the energy transfer or signal change, or isolating and identifying the confirmed target material.

FIG. 4 is a schematic view showing the fourth method of the present invention, i.e., constructs in which formation of a nano-assembly matrix is induced by the direct interaction between X and X or X' or the indirect interaction through A wherein X, X' and A are the same or different materials, and N and N' are nano-assembly matrix-forming materials. In FIG. 4(A), the same nano-assembly matrix-forming materials are used, in FIG. 4(B), different nano-assembly matrix-forming materials are used, and in FIG. 4(C), the same bait materials are used. As shown in FIG. 4, bait materials bound to nano-assembly matrix-forming materials form a nano-assembly matrix by the interaction between the bait materials and are displayed on the nano-assembly matrix at high density. One or more materials of N, X, X' and A are labeled with a label, and the energy transfer or signal change caused by the interaction between detector materials are measured.

A fifth method for labeling or isolating a target material interacting with a bait according to the present invention comprises the steps of:

(i) providing bait materials having mediator (regulator) materials fused thereto and nano-assembly matrix-forming materials to the same field or system, wherein at least one of the mediator (regulator) material, the bait material and the nano-assembly material-forming material is labeled with a label;

(ii) forming a nano-assembly matrix by the interaction between the mediator (regulator) materials to display the bait materials at high density;

(iii) providing a library of prey materials to the nano-assembly matrix, labeling a prey material bound by interaction with the bait materials displayed on the nano-assembly matrix at high density, and selecting the labeled prey material as the target material; and (iv) confirming the labeled target material using the energy transfer or signal change, or isolating and identifying the confirmed target material.

FIG. 5 is a schematic view showing the fifth method of the present invention, i.e., constructs in which formation of a nano-assembly matrix is induced by the indirect interaction between X or X and X' through the mediator (regulator)

materials A and B or A, B and C bound to the detector materials wherein X, X', A, B and C are the same or different materials, and N and N' are nano-assembly matrix-forming materials. In FIG. 5(A), the same nano-assembly matrix-forming materials are used, in FIG. 5(B), different nano-assembly matrix-forming materials are used, and in FIG. 5(C), the same bait materials are used. As shown in FIG. 5, bait materials bound to the nano-assembly matrix-forming materials are displayed at high density on a nano-assembly matrix formed either by the direct interaction between mediator (regulator) materials fused thereto or by the indirect interaction through the mediator (regulator) material C. One or more materials of N, X, X', A, B and C are labeled with a label, and the energy transfer or signal change caused by the interaction between detector materials are measured.

Meanwhile, in the present invention, isolation of the target molecule that interacts with the bait may be performed in the following manner without labeling the target molecule.

Specifically, a first method for isolating a target material interacting with a bait according to the present invention comprises the steps of:

(i) providing mediator (regulator) materials, bait materials and nano-assembly matrix-forming materials to the same field or system, wherein at least one of the mediator (regulator) material, the bait material and the nano-assembly material-forming material is labeled with a label;

(ii) forming a nano-assembly matrix by the interaction between the mediator (regulator) materials to display the bait materials at high density; and (iii) providing a library of prey materials, and isolating and identifying, as the target material, a prey material that interacted with the bait materials.

A second method for isolating a target material interacting with a bait according to the present invention comprises the steps of:

(i) providing first mediator (regulator) materials, second mediator (regulator) materials, bait materials and nano-assembly matrix-forming materials to the same field or system, wherein at least one of the mediator (regulator) material, the bait material and the nano-assembly material-forming material is labeled with a label;

(ii) forming a nano-assembly matrix by the interaction between the first mediator (regulator) materials, and displaying the bait materials on the nano-assembly matrix at high density by the interaction between the second mediator (regulator) materials; and (iii) providing a library of prey materials, and isolating and identifying, as the target material, a prey material that interacted with the bait materials.

A third method for isolating a target material interacting with a bait according to the present invention comprises the steps of:

(i) providing bait materials and nano-assembly matrix-forming materials to the same field or system, wherein at least one of the bait material and the nano-assembly matrix-forming material is labeled with a label;

(ii) forming nano-assembly unit matrix to display the bait materials at high density; and (iii) providing a library of prey materials to the nano-assembly unit matrix, and isolating and identifying, as the target material, a prey material that interacted with the bait materials, or forming a nano-assembly matrix from the nano-assembly unit matrix by mediator (regulator) materials, providing a library of prey materials to the formed nano-assembly matrix, and isolating and identifying, as the target material, a prey material that interacted with the bait materials.

A fourth method for isolating a target material interacting with a bait according to the present invention comprises the steps of:

(i) providing bait materials and nano-assembly matrix-forming materials to the same field or system, wherein at least one of the bait material and the nano-assembly matrix-forming material is labeled with a label;

(ii) forming a nano-assembly matrix by the interaction between the bait materials to display the bait materials at high density; and (iii) providing a library of prey materials to the nano-assembly matrix, and isolating and identifying, as the target material, a prey material that interacted with the bait materials.

A fifth method for isolating a target material interacting with a bait according to the present invention comprises the steps of:

(i) providing bait materials having mediator (regulator) materials fused thereto and nano-assembly matrix-forming materials to the same field or system, wherein at least one of the mediator (regulator) material, the bait material and the nano-assembly material-forming material is labeled with a label;

(ii) forming a nano-assembly matrix by the interaction between the mediator (regulator) materials to display the bait materials at high density; and (iii) providing a library of prey materials to the nano-assembly matrix, and isolating and identifying, as the target material, a prey material that interacted with the bait materials.

Schematic views of the above-described methods correspond to FIGS. 1 to 5.

In the above-described methods according to the present invention, the binding between the materials used in the present invention, including nano-assembly matrix-forming materials, bait molecules, prey molecules, mediator (regulator) molecules inducing nano-assembly matrix formation and labels, may include physical, chemical, electrostatic or biological direct or indirect binding. Among them, when biological binding occurs, a probe comprising an antibody, a protein, a protein domain, a motif, a peptide or the like may be used.

In step (i) in the methods according to the first to fifth aspects of the present invention, molecules that do not interact with the bait molecule and the prey molecule may further be added and displayed on the nano-assembly matrix-forming material. When the molecules that do not interact with the bait molecule and the prey molecule are displayed together with the nano-assembly matrix-forming materials, the density and distance can be suitably controlled, and the sensitivity of FRET can be suitably controlled.

The method of the present invention has advantages in that the target molecule can be easily isolated and identified and the detection and analysis of the target molecule can be performed at high throughput. Thus, the method of the present invention can be performed not only in vitro, but also in vivo, and particularly, nano-assembly matrices or nano-assembly unit matrix can be formed in cells, so that the target molecules can be easily captured and isolated at high density by the bait molecules displayed at high density. Particularly, if the target molecules are captured in cells, nano-assembly matrices or nano-assembly unit matrix can be isolated by lysing cells, and the target molecules can be obtained therefrom at high concentration. Because of these advantages, the method of the present invention is very useful.

Formation of the nano-assembly matrix can be measured or detected using widely known general methods, including a magnetic method, a radioactive method, a method using an enzyme for ELISA, a method of detecting a fluorescent or luminescent material, an optical method, or a method employing a microscope, an imaging system, a scanner, a reader, a spectrophotometer, MRI (magnetic resonance imaging), SQUID, an MR relaxometer, FACS (fluorescene associated cell sorting), a fluorometer or a luminometer. In addition, the nano-assembly matrix can be isolated using these methods.

In other words, isolation of the target molecules can be performed using known general methods. For example, the target molecules can be isolated and identified using electrophoresis, a mass spectrometer, metabolite separation and analysis, protein isolation and analysis, chromatography, an optical method, a microscope, an imaging system, a scanner, a reader, a spectrophotometer, MRI (magnetic resonance imaging), SQUID, an MR relaxometer, FACS (fluorescene associated cell sorting, a fluorometer or a luminometer.

In another aspect, the present invention is directed to a method for detecting a target material that a specific bait (e.g., a specific bioactive material) in vitro or in vivo.

Specifically, a first method for detecting a target material interacting with a bait according to the present invention comprises the steps of:

(i) providing mediator (regulator) materials, bait materials and nano-assembly matrix-forming materials to the same field or system;

(ii) forming a nano-assembly matrix by the interaction between the mediator (regulator) materials to display the bait materials at high density;

(iii) providing a library of prey materials to the nano-assembly matrix; and (iv) measuring the energy transfer or signal change to detect the interaction between the bait material and the prey material, wherein at least one of the mediator (regulator) material, the bait material, the nano-assembly material-forming material and the library of prey materials is labeled with a label.

A second method for detecting a target material interacting with a bait according to the present invention comprises the steps of:

(i) providing first mediator (regulator) materials, second mediator (regulator) materials, bait materials and nano-assembly matrix-forming materials to the same field or system;

(ii) forming a nano-assembly matrix by the interaction between the first mediator (regulator) materials, and displaying the bait materials on the nano-assembly matrix at high density by the interaction between the second mediator (regulator) materials;

(iii) providing a library of prey materials to the nano-assembly matrix; and (iv) measuring the energy transfer or signal change to detect the interaction between the bait material and the prey material, wherein at least one of the mediator (regulator) material, the bait material, the nano-assembly material-forming material and the library of prey materials is labeled with a label.

A third method for detecting a target material interacting with a bait according to the present invention comprises the steps of:

(i) providing bait materials and nano-assembly matrix-forming materials to the same field or system;

(ii) forming nano-assembly unit matrix to display the bait materials at high density;

(iii) providing a library of prey materials to the nano-assembly unit matrix; and (iv) measuring the energy transfer or signal change to detect the interaction between the bait material and the prey material, wherein at least one of the bait material, the nano-assembly material-forming material and the library of prey materials is labeled with a label.

A fourth method for detecting a target material interacting with a bait according to the present invention comprises the steps of:

(i) providing bait materials and nano-assembly matrix-forming materials to the same field or system;

(ii) forming a nano-assembly matrix by the interaction between the bait materials to display the bait materials at high density;

(iii) providing a library of prey materials to the nano-assembly matrix; and (iv) measuring the energy transfer or signal change to detect the interaction between the bait material and the prey material, wherein at least one of the bait material, the nano-assembly material-forming material and the library of prey materials is labeled with a label.

A fifth method for detecting a target material interacting with a bait according to the present invention comprises the steps of:

(i) providing bait materials having mediator (regulator) materials fused thereto and nano-assembly matrix-forming materials to the same field or system;

(ii) forming a nano-assembly matrix by the interaction between the mediator (regulator) materials to display the bait materials at high density;

(iii) providing a library of prey materials to the nano-assembly matrix; and (iv) measuring the energy transfer or signal change to detect the interaction between the bait material and the prey material, wherein at least one of the bait material, the nano-assembly material-forming material and the library of prey materials is labeled with a label.

Additionally, for detection of the target material, the nano-assembly matrix-forming material can be bound to the prey material, so that the nano-assembly matrix can be formed by the interaction between the bait material and the prey material.

Specifically, a sixth method for detecting a target material interacting with a bait according to the present invention comprises the steps of:

(i) providing bait materials, nano-assembly matrix-forming materials and a library of prey materials to the same field or system;

(ii) reacting the bait materials with the prey materials so that a nano-assembly matrix is formed to display the bait materials and the prey materials at high density; and (iii) measuring the energy transfer or signal change to detect the interaction between the bait materials and the prey materials, wherein at least one of the bait material, the nano-assembly material-forming material and the library of prey materials is labeled with a label.

FIG. 6 is a schematic view showing the sixth method of the present invention, i.e., constructs for detecting the direct interaction between X and Y or the indirect interaction through A in a nano-assembly matrix wherein X, Y and A are the same or different materials, and N and N' are nano-assembly matrix-forming materials. In FIG. 6(A), the same nano-assembly matrix-forming materials are used, and in FIG. 6(B), different nano-assembly matrix-forming materials are used. As shown in FIG. 6, the bait material and prey material bound to the nano-assembly matrix-forming materials form a nano-assembly matrix by the direct interaction therebetween or the indirect interaction through the mediator (regulator) material A. One or more materials of N, X, Y and A are labeled with a label, and the energy transfer or signal change caused by the interaction between detector materials are measured.

FIG. 7 is a schematic view showing a seventh method of the present invention. i.e., constructs for detecting the interaction between X and Y in a nano-assembly matrix when the direct interaction between A and B or the indirect interaction through C occur wherein A, B, C, X and Y are the same or different materials, and N and N' are nano-assembly matrix-forming materials. In FIG. 7(A), the same nano-assembly matrix-forming materials are used, and in FIG. 7(B), different nano-assembly matrix-forming materials are used. As shown in FIG. 7, a bait material fused to a mediator (regulator) material is bound to a nano-assembly matrix-forming material by the interaction between the mediator (regulator) materials and forms a nano-assembly matrix by the interaction between the prey materials bound to the nano-assembly matrix-forming material. One or more materials of N, X, Y, A, B and C are labeled with a label, and the energy transfer or signal change caused by the interaction between detector materials are measured.

FIG. 8 is another schematic view showing the sixth method of the present invention, i.e., constructs for detecting the interaction between X and Y in a nano-assembly matrix when the direct interaction between A and B or the indirect interaction through C occur wherein A, B, C, X and Y are the same or different materials, and N and N' are nano-assembly matrix-forming materials. In FIG. 8(A), X materials does not interact with each other, and FIG. 8(B), X materials interacts interact with each other. As shown in FIG. 8, the bait materials fused to mediator (regulator) materials are bound to a nano-assembly matrix-forming material by the interaction between the mediator (regulator) materials and form a nano-assembly matrix by interaction with prey materials, fused to the mediator (regulator) materials and bound to the nano-assembly matrix-forming materials by the interaction between the mediator (regulator) molecules. One or more materials of N, X, Y, A, B and C are labeled with a label, and the energy transfer or signal change caused by the interaction between detector materials are measured.

In still another aspect, the present invention is directed to a method for detecting the interaction between a specific "bait" molecule (e.g., a specific bioactive molecule) and a "prey" molecule (e.g., another bioactive molecule) to be analyzed or detected, in vitro or in vivo.

Specifically, a first method for detecting or quantifying the interaction between materials according to the present invention comprises the steps of:

(i) providing mediator (regulator) materials, bait materials and nano-assembly matrix-forming materials to the same field or system;

(ii) forming a nano-assembly matrix by the interaction between the mediator (regulator) materials to display the bait materials at high density;

(iii) providing prey materials to the nano-assembly matrix; and (iv) measuring the energy transfer or signal change to detect or quantify the interaction between the bait materials and the prey materials, wherein at least one of the mediator (regulator) material, the bait material, the nano-assembly material-forming material and the prey material is labeled with a label A second method for detecting or quantifying the interaction between materials according to the present invention comprises the steps of:

(i) providing first mediator (regulator) materials, second mediator (regulator) materials, bait materials and nano-assembly matrix-forming materials to the same field or system;

(ii) forming a nano-assembly matrix by the interaction between the first mediator (regulator) materials and displaying the bait materials on the nano-assembly matrix at high density by the interaction between the second mediator (regulator) materials;

(iii) providing prey materials to the nano-assembly matrix; and (iv) measuring the energy transfer or signal change to detect or quantify the interaction between the bait materials and the prey materials, wherein at least one of the mediator (regulator) material, the bait material, the nano-assembly material-forming material and the prey material is labeled with a label.

A third method for detecting or quantifying the interaction between materials according to the present invention comprises the steps of:

(i) providing bait materials and nano-assembly matrix-forming materials to the same field or system;

(ii) forming nano-assembly unit matrix to display the bait materials at high density;

(iii) providing prey materials to the nano-assembly unit matrix; and (iv) measuring the energy transfer or signal change to detect or quantify the interaction between the bait materials and the prey materials, wherein at least one of the bait material, the nano-assembly material-forming material and the prey material is labeled with a label.

A fourth method for detecting or quantifying the interaction between materials according to the present invention comprises the steps of:

(i) providing bait materials and nano-assembly matrix-forming materials to the same field or system;

(ii) forming a nano-assembly matrix by the interaction between the bait materials to display the bait materials at high density;

(iii) providing prey materials to the nano-assembly matrix; and (iv) measuring the energy transfer or signal change to detect or quantify the interaction between the bait materials and the prey materials, wherein at least one of the bait material, the nano-assembly material-forming material and the prey material is labeled with a label.

A fifth method for detecting or quantifying the interaction between materials according to the present invention comprises the steps of:

(i) providing bait materials having mediator (regulator) materials fused thereto and nano-assembly matrix-forming materials to the same field or system;

(ii) forming a nano-assembly matrix by the interaction between the mediator (regulator) materials to display the bait materials at high density;

(iii) providing prey materials to the nano-assembly matrix; and (iv) measuring the energy transfer or signal change to detect or quantify the interaction between the bait materials and the prey materials, wherein at least one of the bait material, the nano-assembly material-forming material and the prey material is labeled with a label.

A sixth method for detecting or quantifying the interaction between materials according to the present invention comprises the steps of:

(i) providing bait materials, prey materials and nano-assembly matrix-forming materials to the same field or system;

(ii) reacting the bait materials with the prey materials so that a nano-assembly matrix is formed to display the bait materials and the prey materials at high density; and (iv) measuring the energy transfer or signal change to detect or quantify the interaction between the bait materials and the prey materials, wherein at least one of the bait material, the nano-assembly material-forming material and the prey material is labeled with a label.

In yet another aspect, the present invention provides a method for screening a target material that inhibits or activates the interaction between a bait material and a prey material.

Specifically, a first method for screening a target material that inhibits or activates the interaction between bait materials and prey materials comprises the steps of:

(i) providing mediator (regulator) materials, bait materials and nano-assembly matrix-forming materials to the same field or system, and forming a nano-assembly matrix by the interaction between the mediator (regulator) materials to display the bait materials at high density;

(ii) providing prey materials to the formed nano-assembly matrix in the presence of target candidates; and (iii) selecting, as a target blocker material or a target activator material, a target candidate corresponding to a case in which the energy transfer or signal change in the presence of the target candidate is reduced (inhibited) or increased (activated) compared to the energy transfer or signal change in the absence of the target candidate, wherein at least one of the mediator (regulator) material, the bait material, the nano-assembly material-forming material and the prey material is labeled with a label.

A second method for screening a target material that inhibits or activates the interaction between bait materials and prey materials comprises the steps of:

(i) providing first mediator (regulator) materials, second mediator (regulator) materials, bait materials and nano-assembly matrix-forming materials to the same field or system, forming a nano-assembly matrix by the interaction between the first mediator (regulator) materials, and displaying the bait materials on the nano-assembly matrix at high density by the interaction between the second mediator (regulator) materials;

(ii) providing prey materials to the formed nano-assembly matrix in the presence of target candidates; and (iii) selecting, as a target blocker material or a target activator material, a target candidate corresponding to a case in which the energy transfer or signal change in the presence of the target candidate is reduced (inhibited) or increased (activated) compared to the energy transfer or signal change in the absence of the target candidate, wherein at least one of the mediator (regulator) material, the bait material, the nano-assembly material-forming material and the prey material is labeled with a label.

A third method for screening a target material that inhibits or activates the interaction between bait materials and prey materials comprises the steps of:

(i) providing bait materials, prey materials and nano-assembly matrix-forming materials to the same field or system in the presence of target candidates to display the bait materials on a nano-assembly unit matrix at high density; and (iii) selecting, as a target blocker material or a target activator material, a target candidate corresponding to a case in which the energy transfer or signal change in the presence of the target candidate is reduced (inhibited) or increased (activated) compared to the energy transfer or signal change in the absence of the target candidate, wherein at least one of the bait material, the nano-assembly material-forming material and the prey material is labeled with a label.

A fourth method for screening a target material that inhibits or activates the interaction between bait materials and prey materials comprises the steps of:

(i) providing bait materials and nano-assembly matrix-forming materials to the same field or system, and forming a nano-assembly matrix by the interaction between the bait materials to display bait materials at high density;

(ii) providing prey materials to the formed nano-assembly matrix in the presence of target candidates; and (iii) selecting, as a target blocker material or a target activator material, a target candidate corresponding to a case in which the energy transfer or signal change in the presence of the target candidate is reduced (inhibited) or increased (activated) compared to the energy transfer or signal change in the absence of the target candidate, wherein at least one of the mediator (regulator) material, the bait material, the nano-assembly material-forming material and the prey material is labeled with a label.

A fifth method for screening a target material that inhibits or activates the interaction between bait materials and prey materials comprises the steps of:

(i) providing bait materials having mediator (regulator) materials bound thereto and nano-assembly matrix-forming materials to the same field or system, and forming a nano-assembly matrix by the interaction between the mediator (regulator) materials to display bait materials at high density;

(ii) providing prey materials to the formed nano-assembly matrix in the presence of target candidates; and (iii) selecting, as a target blocker material or a target activator material, a target candidate corresponding to a case in which the energy transfer or signal change in the presence of the target candidate is reduced (inhibited) or increased (activated) compared to the energy transfer or signal change in the absence of the target candidate, wherein at least one of the mediator (regulator) material, the bait material, the nano-assembly material-forming material and the prey material is labeled with a label.

A sixth method for screening a target material that inhibits or activates the interaction between bait materials and prey materials comprises the steps of:

(i) providing bait materials, prey materials and nano-assembly matrix-forming materials to the same field or system, wherein at least one of the bait material, the prey material and the nano-assembly matrix-forming material is labeled with a label;

(ii) reacting the bait materials with the prey materials in the presence of target candidates so that a nano-assembly matrix is formed to display the bait materials and the prey materials at high density; and (iii) selecting, as a target blocker material or a target activator material, a target candidate corresponding to a case in which the energy transfer or signal change in the presence of the target candidate is reduced (inhibited) or increased (activated) compared to the energy transfer or signal change in the absence of the target candidate.

In the above-described methods according to the present invention, the binding between the materials used in the present invention, including nano-assembly matrix-forming materials, bait molecules, prey molecules, mediator (regulator) molecules inducing nano-assembly matrix formation and labels, may include physical, chemical, electrostatic or biological direct or indirect binding. Among them, when biological binding occurs, a probe comprising an antibody, a protein, a protein domain, a motif, a peptide or the like may be used.

In the methods of the present invention, any detector materials may be bound directly or indirectly to nano-assembly matrix-forming materials, while prey materials may be bound to the nano-assembly matrix-forming materials. In addition, mediator (regulator) materials may be bound to nano-assembly matrix-forming materials, while mediator (regulator) materials may be bound to bait materials and prey materials.

The regulator material may be a material that is involved in the on/off of changes in physiological functions (inhibition or activation of physiological functions) of interest. As described above, the assembly or dis-assembly of nano-assembly unit matrix or the display of specific materials in the nano-assembly matrix can be regulated using bioactive molecules that interact with each other, thereby regulating physiological functions in an intracellular or in vivo environment.

In addition, by examining a change in physiological function of interest, for example, the stimulation of activity of a specific material, or an increase or decrease in the production of a specific material, whether the physiological function of cells was regulated can be determined by the above-described method.

In the method of the present invention, the nano-assembly matrix-forming molecule, the detector material or the mediator (regulator) material may be can be labeled with a label. Herein, examples of the label include, but are not limited to, magnetic materials, radioactive materials, enzymatic materials for ELISA, fluorescent materials, and luminescent materials. Examples of the fluorescent materials include fluorescent dyes, fluorescent proteins and fluorescent nanoparticles.

In addition, in the method of the present invention, the bait molecule, the prey material or the mediator (regulator) material may be a bioactive molecule. Herein, the bioactive molecule may be one or more selected from the group consisting of nucleic acids, nucleotides, proteins, peptides, amino acids, saccharides, lipids, vitamins, and chemical compounds, but is not limited thereto.

The method of the present invention can be performed in vitro or in vivo. When the method of the present invention is performed in vivo, it can be performed in eukaryotic cells, prokaryotic cells, the living tissue and cells of mammals including humans, or the living tissue and cells of plants. Particularly, the method of the present invention can be performed in the living cells or tissues of Zebra fish, *C. elegans*, yeast, flies or frogs.

The nano-assembly matrix-forming material, the bait material, the prey material, the mediator material (material inducing nano-assembly matrix formation) and the label, which are used in the present invention, can be easily introduced into cells using widely known general methods. For example, introduction of these materials into cells can be performed by any one method selected from the group consisting of direct injection, a method employing a transducible peptide, a fusogenic peptide, a lipid delivery system or a combination thereof, electroporation, magnetofection, and parenteral administration, oral administration, intranasal administration, subcutaneous administration, aerosolized administration and intravenous administration into mammals including humans.

In the methods of the present invention, formation of the nano-assembly matrix can be examined using a label. Particularly, the detector molecule, the nano-assembly matrix-forming material or the mediator (regulator) molecule, which are used in the present invention, may be labeled with a label. If necessary, a radioactive label, a fluorescent material or a luminescent material may be used as a label on the nano-assembly matrix formed by the interaction between specific molecules according to the present invention. Examples of the radioactive label that may be used in the present invention include all known labels, including $^{32}P$, $^{35}S$, $^{3}H$ and $^{14}C$. Moreover, fluorescent materials that may be used as labels in the present invention show fluorescence by themselves or by interaction with other materials and include, for example, fluorescent dyes such as FITC, rhodamine and the like; fluorescent proteins such as ECFP, TagCFP, mTFP1, GFP, YFP, CFP and RFP; tetracysteine motifs; and fluorescent nanoparticles. In addition, luminescent materials that may be used as labels in the present invention shows luminescence by themselves or by interaction with other materials and include, for example, luciferase and the like.

In the methods of the present invention, formation of the nano-assembly matrix can be measured or detected using widely known general methods, including a magnetic method, a radioactive method, a method using an enzyme for ELISA, a method of detecting a fluorescent or luminescent material, an optical method, or a method employing a microscope, an imaging system, a scanner, a reader, a spectrophotometer, MRI (magnetic resonance imaging), SQUID, an MR relaxometer, FACS (fluorescene associated cell sorting), a fluorometer or a luminometer. In addition, the nano-assembly matrix can be isolated using these methods.

In the present invention, the transfer of energy signals can be measured by energy intensity and resonance. For example, radioactivity transfer, luminescence transfer, magnetic transfer or FRET (fluorescence resonance energy transfer) may be used.

Additionally, regulator molecules can be loaded at high density either into the nano-assembly matrix formed by the method of the present invention or into the nano-assembly unit matrix, and physiological activities or functions can be regulated or induced by the loaded molecules that are exposed as a result of the dis-assembly of the nano-assembly matrix or the nano-assembly unit matrix.

Hereinafter, the components that are used in the methods of the present invention will be described in detail.

The "nano-assembly matrix-forming materials" are poly/multi-valent materials having a plurality of the same or different binding moieties and can form matrices by the interaction or self-assembly between them. Preferably, materials that can form matrices by self-assembly are used. These matrices preferably consist of nano-sized particles. In the present invention, two or more different nano-assembly matrix-forming materials are preferably used.

Preferred examples of materials that form nano-assembly matrices by self-assembly may include proteins having self-assembly or self-association domains, for example, ferritin, ferritin-like protein, DPS (DNA binding protein from starved cells), DPS-like protein, HSP (heat shock protein), magnetosome protein, viral protein, calcium/calmodulin-dependent kinase II, and dsRed. Moreover, a variety of chemically synthesized nanoparticles can also form nano-assembly matrices. For example, various kinds of nanoparticles, including gold nanoparticles, Q dots or magnetic nanoparticles, may be used. In one example of the present invention, among molecules or proteins that can form nano-assembly unit matrix (nano-sized unit matrices) by self-assembly, the ferritin protein was used.

The ferritin protein forms a spherical nanoparticle matrix by self-assembly of 24 ferritin subunits, has an outer diameter of about 12 nm and an inner diameter of about 9 nm and contains more than 2500 iron atoms (Chasteen, N. D. Struc. Biol. 126:182-194, 1999). If a nano-assembly matrix is formed by the interaction between the detector molecules or between the between the mediator (regulator) molecules, which occurs on the surface of the nanoparticle matrix formed by the ferritin protein, the interaction can be dynamically detected by analyzing a label (such as a fluorescent, luminescent, magnetic or radioactive material) bound to the detector molecules or the mediator (regulator) molecules, using an analytical device such as a microscope.

The detector molecules that are used in the present invention may be any bioactive molecules that interact with each other. The bioactive molecules are materials that show physiological activity in vivo and can interact with various bioactive molecules in the human body to regulate the function or activity thereof. Preferred examples of the bioactive molecules include nucleic acids, mono-/oligo-/poly-nucleotides, proteins, mono-/oligo-/poly-peptides, amino acids, mono-/oligo-/poly-saccharides, lipids, vitamins, chemical compounds, and small molecules constituting these materials.

In the present invention, the energy transfer or signal change may be either the energy transfer caused by the resonance between label molecules or the change in intensity or pattern of images or signals caused by the label. Herein, the energy transfer includes various changes, including the energy change caused by resonance, and the transfer, interference and quenching of energy. In addition, the change of signals includes changes in the intensity and pattern of images (e.g., number, area, intensity and distribution, which appear in image patterns such as dotted patterns) and changes in the intensity and pattern of signals (e.g., the number, width, area, height and distribution of pulses in flow cytometry). In addition, it includes a change in the intensity of signals in ELISA.

In the present invention, an energy transfer signal can be measured using any method such as resonance. Examples of the method for measuring an energy transfer signal include BRET (bioluminescence resonance energy transfer) and FRET (fluorescence resonance energy transfer).

Meanwhile, in the methods of the present invention, a label is preferably used to examine the interaction between the bait and prey molecules.

The label that is used in the present invention may be a fluorescent or luminescent material. Examples of the fluorescent or luminescent material that shows fluorescence by itself or by interaction with other materials include fluorescent dyes such as FITC, rhodamine and the like; fluorescent proteins such as ECFP, TagCFP, mTFP1, GFP, YFP, CFP and RFP; tetracysteine motifs; and fluorescent nanoparticles. The luminescent material that shows luminescence by itself or by interaction with other materials may be, for example, luciferase or the like.

The energy transfer or signal change can be measured by known general methods, including a magnetic method, a radioactive method, a method employing an enzyme for ELISA, a method of detecting a fluorescent or luminescent material, an optical method, or a method employing a microscope, an imaging system, a scanner, a reader, a spectrophotometer, MRI (magnetic resonance imaging), SQUID, an MR relaxometer, flow Cytometry, FACS (fluorescene associated cell sorting), a fluorometer or a luminometer. Particularly, separation can also be performed using FACS, MS or the like.

The 'bait' corresponding to a detector material and the 'prey' molecule corresponding to the partner of the bait may be any candidate molecules anticipated to interact with each other. Preferably, they are bioactive molecules.

The bioactive molecules include all the materials showing physiological activity in vivo, and as the bioactive molecules, any molecules which can interact with biomaterials in vivo to regulate the function or activity of the biomaterials may be used. Preferred examples of the bioactive molecules include nucleic acids, mono-/oligo-/poly-nucleotides, proteins, mono-/oligo-/poly-peptides, amino acids, mono-/oligo-/poly-saccharides, lipids, vitamins, and chemical compounds, as well as smaller molecules constituting these molecules.

Specific examples of the interaction between the bait and the prey may include the interaction between Leucine Zippers domains, the interaction between drug-drug targets, the interaction between FRB and FKBP, which are the pharmaceutically relevant binding partners of a Rapamycin compound, the interaction between an FK506 compound and an FKBP protein which is the pharmaceutically relevant partner thereof, the interaction between an AP1510 compound and an FKBP protein, the interaction between an IkBα protein and an RelA which is the binding partner thereof, the interaction between an IkBα protein, which is regulated according to a physiological signal of TNFa, and a bTrCP or IKKb protein which is the binding partner of the IkBα protein, the intracellular interaction (let-7b miRNA binding to lin-28 mRNA) of miRNA with mRNA, the interaction of an Ago2 protein with miRNA, the interaction of an MS2 protein with an MS2-binding mRNA site, the intracellular interaction of a DHFR protein with an MTX compound, etc.

The mediator (regulator) materials which regulate the bait-prey interaction are materials that activate the bait-prey interaction to mediate (regulate) the binding between the bait and the prey, and as the mediator (regulator) materials, any bioactive molecules or compounds may be used without limitation, as long as they exhibit the above function. However, molecules interacting specifically with the bait-prey pair are preferably used. Because the nano-assembly matrix is formed by the interaction between the bait and the prey, the materials that mediate the bait-prey interaction are considered to belong to the scope of the mediator (regulator) materials which induce the formation of nano-assembly matrices as defined in the present invention.

To mediate (regulate) the prey-bait interaction, a protein which is regulated by an external signal may be used. Alternatively, the property of miRNA binding specifically to its target mRNA may also be used.

The mediator (regulator) materials which induce the formation of nano-assembly matrices in the present invention are meant to include all materials which can interact directly or indirectly with each other on the surface of the nano-assembly matrix-forming materials to form nano-assembly matrices. Such materials that mediate or regulate the activity of the mediator (regulator) materials are also considered as mediator (regulator) materials in a broad sense. When the formation of nano-assembly matrices is induced by the bait-prey interaction as described above, materials that regulate or mediate the bait-prey interaction are also included in the scope of said mediator (regulator) materials in a broad sense.

As such mediator (regulator) materials, any materials may be used without limitation, as long as they exhibit the function of inducing the formation of nano-assembly matrices. Accordingly, all the materials or phenomena that can induce the formation of nano-assembly matrices by specific phenomena, such as either the binding between materials interacting specifically with each other or mutations can be understood as mediator (regulator) materials. Namely, the term "mediator (regulator) materials" as used herein is meant to include all specific materials, specific phenomena or specific interactions. Such mediator (regulator) materials may be used in a combination of two or more thereof.

If the prey was detected using the properties of the bait-prey pair, while a nano-assembly matrix was formed using the properties of the bait, it is considered that the used bait is a mediator (regulator) material inducing the formation of the nano-assembly matrix and, at the same time, exhibits the function of the bait used to detect an interaction with the partner prey.

In a further aspect, the present invention provides a composition for diagnosing disease or a composition for disease-related targeting, imaging or diagnosis, the composition comprising an isolated nano-assembly matrix or nano-assembly unit matrix formed by the above-described methods.

Herein, the disease may be a disease related to either the detector materials, which are displayed at high density on the nano-assembly matrix or the nano-assembly unit matrix, or a material that is bound to or captured by the mediator (regulator) material.

In addition, the disease can be targeted, imaged or diagnosed by a method comprising the steps of: introducing the isolated nano-assembly matrix or nano-assembly unit matrix into a cell, a tissue or a living body and reacting the introduced nano-assembly matrix or nano-assembly unit matrix with a prey library; and labeling a prey material bound by interaction with the bait materials displayed on the nano-assembly matrix at high density, selecting the labeled prey material as the target material, and measuring the energy signal transfer or signal change in the labeled prey material, thereby targeting, imaging or diagnosing the disease.

Herein, regulator molecules capable of interacting with the detector molecules on the nano-assembly matrix may further be provided so that they can be displayed on the nano-assembly matrix at high density, after which the nano-assembly matrix can be isolated.

The above-described pharmaceutical composition for diagnosing disease may comprise the isolated nano-assembly matrix or nano matrix alone or together with at least one pharmaceutically acceptable carrier, excipient or diluent. The matrix may be contained in the pharmaceutical composition in a pharmaceutically effective amount according to a disease and the severity thereof, the patient's age, weight, health condition and sex, the route of administration, and the period of treatment.

As used herein, the term "pharmaceutically acceptable composition" refers to a composition that is physiologically acceptable and does not cause gastric disorder, allergic reactions such as gastrointestinal disorder or vertigo, or similar reactions, when administered to humans. Examples of said carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, magnesium stearate and mineral oils.

The pharmaceutical composition of the present invention may additionally contain fillers, anti-aggregating agents, lubricants, wetting agents, perfumes, emulsifiers and preservatives. Also, the pharmaceutical composition of the present invention may be formulated using a method well known in the art, such that it can provide the rapid, sustained or delayed release of the active ingredient after administration to mammals. The pharmaceutical composition of the present invention may be in the form of sterile injection solutions, and the like.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Analysis of Energy Signal Transfer Caused by FKBP-FRB Interaction in Nano-Assembly Matrix after Intracellular Expression of FKBP-CFP-FT and FRB-YFP-FT Fusion Proteins The ferritin genes FTH1 (GenBank Acc. No. BC013724) and FTL (GenBank Acc. No. BC016346) was purchased from Open BioSystems (USA). A recombinant gene based on pcDNA 3.1 was constructed which can express fusion proteins, obtained by fusing the FKBP and FRB protein domains and the fluorescent proteins CFP and YFP to the N-terminal end of ferritin (FT) protein, in mammalian cells by CMV promoter.

The recombinant gene was introduced into HeLa cells (ATCC No. CCL-2), cultured in a 4-well LabTek II chamber slide, using Lipofectamine™ LTX. Then, the cells were incubated in a 5% $CO_2$ incubator at 37° C. for 24 hours to express the fusion proteins.

For imaging of the incubated cells, the culture medium was changed from 10% FBS-containing DMEM (Gibco) to OPTI-MEM (Gibco), and then the cells were imaged with a confocal microscope (ZEISS, LSM710). For imaging of each of the fluorescent proteins, CFP was imaged using a 458-nm laser at a wavelength of 460-500 nm, YFP was imaged using a 514 nm laser at a wavelength of 525-545 nm, and FRET was imaged using a 458 nm laser at a wavelength of 525-545 nm. The degree of FRET in the images obtained with the confocal microscope was analyzed by the sensitized emission method using MetaMorph software (Molecular Device). The cells were imaged before and after treatment with 250 nM of rapamycin (Calbiochem), and the results of the imaging are shown in FIG. 10 (A and B).

Figure 10:
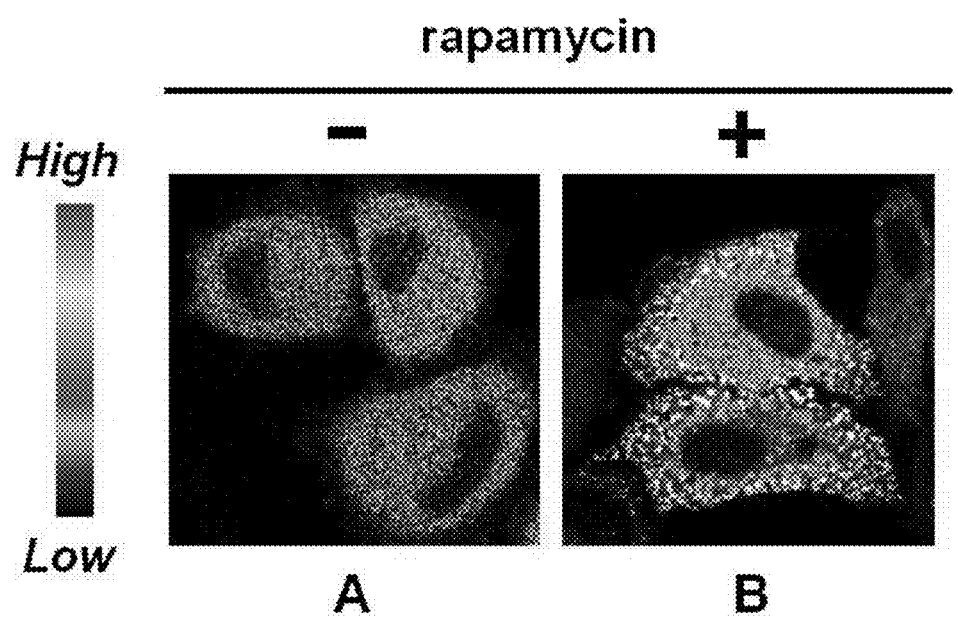
FIG. 10 is a set of photographs showing the results of quantitative FRET analysis of the interaction between FKBP-label (CFP)-FT and FRB-label (YFP)-FT, displayed at high density on a nano-assembly matrix formed from ferritin (FT) protein in HeLa cells, in the presence or absence of a mediator (regulator) material (rapamycin).

As a result, as shown in FIG. 10, the intensity of the FRET signal detected greatly increased to the highest possible level ("high") in the case of treatment with the mediator (regulator) rapamycin (B) compared to the case in which the cells were not treated with rapamycin (A). Thus, the great increase in FRET signal caused by the FKBP-FRB interaction in the nano-assembly matrix was observed.

Example 2: Analysis of Energy Signal Transfer Caused by FKBP-FRB Interaction in Nano-Assembly Matrix after Intracellular Expression of FKBP-mCerulean-FT and FRB-mCitrine-FT Fusion Proteins A recombinant gene based on pcDNA 3.1 was constructed which can express fusion proteins, obtained by fusing the FKBP and FRB protein domains and the fluorescent proteins mCerulean and mCitrine to the N-terminal end of ferritin (FT) protein, in mammalian cells by CMV promoter.

The recombinant gene was introduced into HeLa cells (ATCC No. CCL-2), cultured in a 4-well LabTek II chamber slide, using Lipofectamine™ LTX. Then, the cells were incubated in a 5% $CO_2$ incubator at 37° C. for 24 hours to express the fusion proteins.

For imaging of the incubated cells, the culture medium was changed from 10% FBS-containing DMEM (Gibco) to OPTI-MEM (Gibco), and then the cells were imaged with a confocal microscope (ZEISS, LSM710). For imaging of each of the fluorescent proteins, mCerulean was imaged using a 405-nm laser at a wavelength of 460-490 nm, mCitrine was imaged using a 514 nm laser at a wavelength of 525-550 nm, and FRET was imaged using a 405 nm laser at a wavelength of 525-550 nm. The degree of FRET in the images obtained with the confocal microscope was analyzed by the sensitized emission method using MetaMorph software (Molecular Device). The cells were imaged before and after treatment with 250 nM of rapamycin (Calbiochem), and the results of the imaging are shown in FIGS. 11 and 12.

Figure 11:
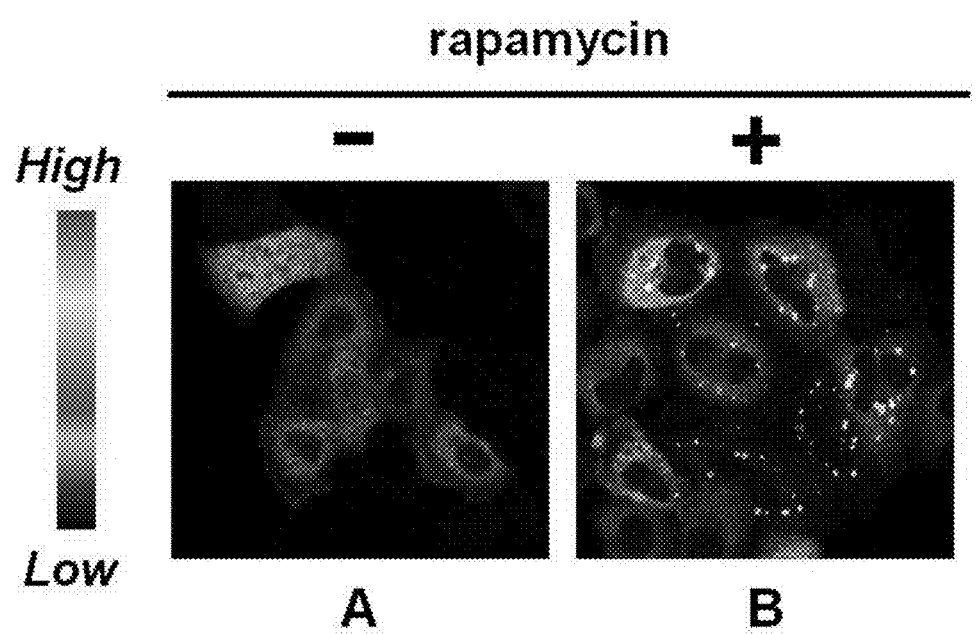
FIG. 11 is a set of photographs showing the results of quantitative FRET analysis of the interaction between FKBP-label (mCerulean)-FT and FRB-label (mCitrine)-FT, displayed at high density on a nano-assembly matrix formed from ferritin (FT) protein in HeLa cells, in the presence or absence of a mediator (regulator) material (rapamycin).
Figure 12:
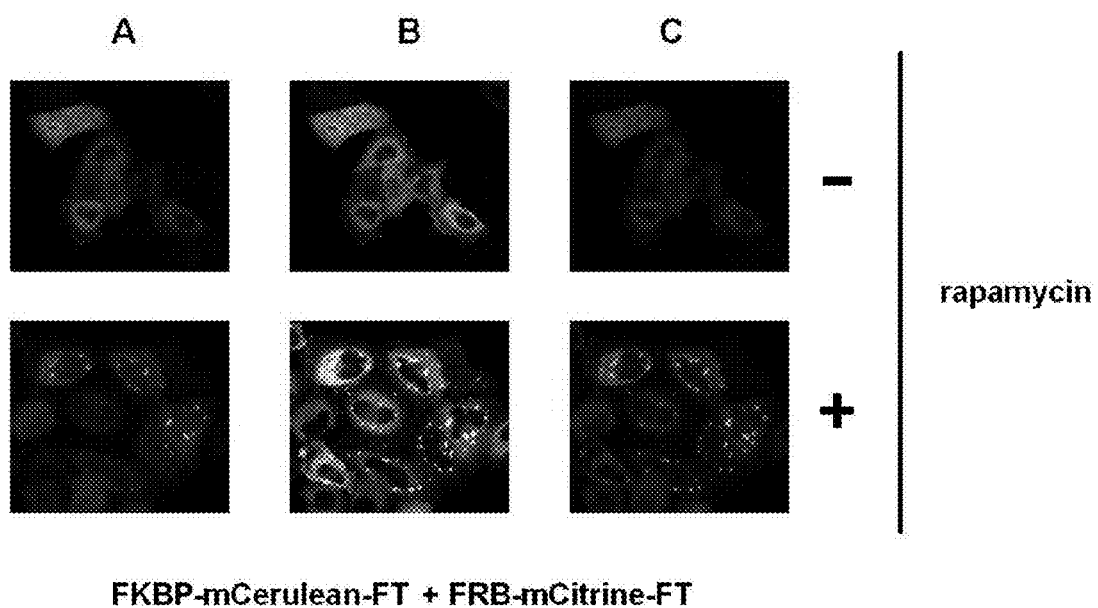
FIG. 12 shows the results of imaging mCerulean (FIG. 12A), mCitrine (FIG. 12B) and FRET (FIG. 12C) in order to examine the interaction between FKBP-label (mCerulean)-FT and FRB-label (mCitrine)-FT, displayed at high density on a nano-assembly matrix formed from ferritin (FT) protein in HeLa cells, in the presence or absence of a mediator (regulator) material (rapamycin).

As a result, as shown in FIGS. 11 and 12, the intensity of the FRET signal detected greatly increased to the highest possible level ("high") in the case of treatment with the mediator (regulator) rapamycin compared to the case in which the cells were not treated with rapamycin. Thus, the great increase in FRET signal caused by the FKBP-FRB interaction in the nano-assembly matrix was observed.

Example 3: Analysis of Energy Signal Transfer Caused by FKBP-FRB Interaction in Nano-Assembly Matrix after Intracellular Expression of FKBP-mCerulean-FT and FRB-mCitrine-DPS Fusion Proteins A recombinant gene based on pcDNA 3.1 was constructed which can express fusion proteins, obtained by fusing the FKBP and FRB protein domains and the fluorescent proteins mCerulean and mCitrine to the N-terminal end of ferritin (FT) protein and DPS protein, in mammalian cells by CMV promoter. The DPS gene was cloned by PCR using known primers.

The recombinant gene was introduced into HeLa cells (ATCC No. CCL-2), cultured in a 4-well LabTek II chamber slide, using Lipofectamine™ LTX. Then, the cells were incubated in a 5% $CO_2$ incubator at 37° C. for 24 hours to express the fusion proteins.

For imaging of the incubated cells, the culture medium was changed from 10% FBS-containing DMEM (Gibco) to OPTI-MEM (Gibco), and then the cells were imaged with a confocal microscope (ZEISS, LSM710).

Figure 13:
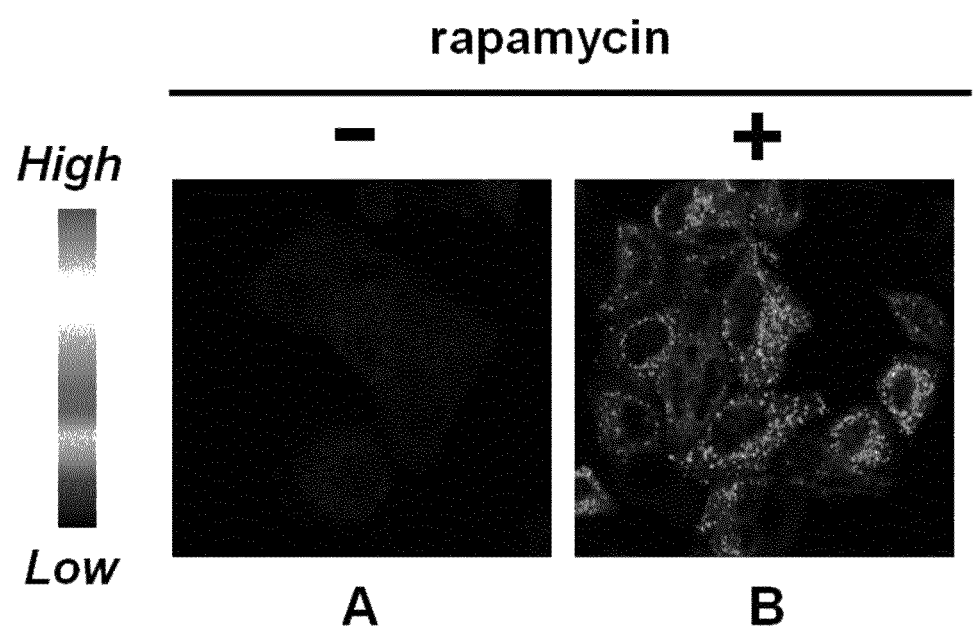
FIG. 13 is a set of photographs showing the results of quantitative FRET analysis of the interaction between FKBP-label (mCerulean)-FT and FRB-label (mCitrine)-DPS, displayed at high density on a nano-assembly matrix formed from ferritin (FT) protein and DPS protein in HeLa cells, in the presence or absence of a mediator (regulator) material (rapamycin).
Figure 14:
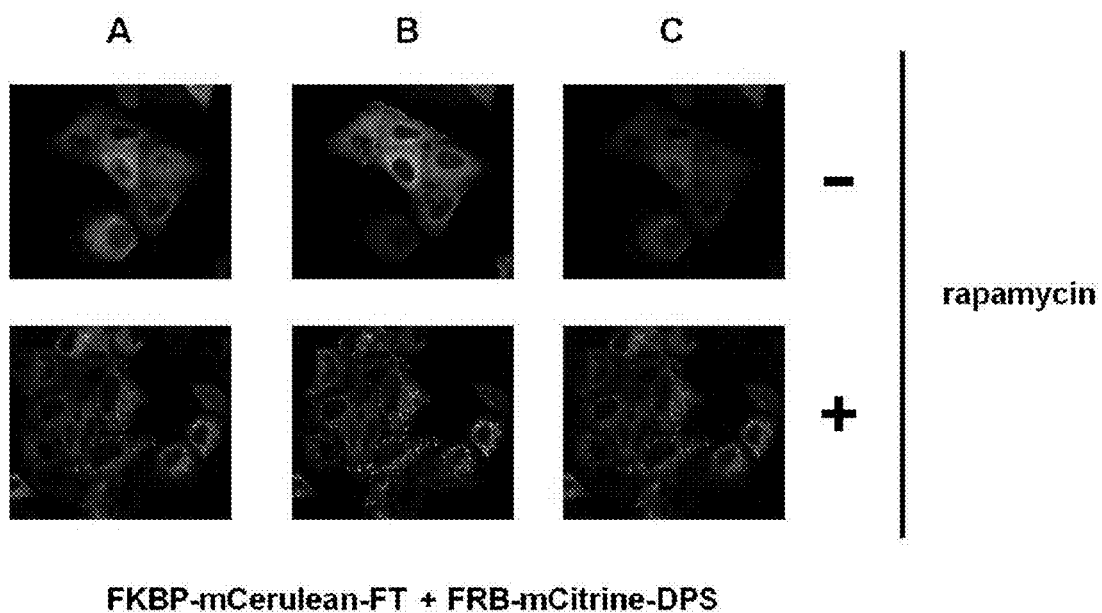
FIG. 14 shows the results of imaging mCerulean (FIG. 14A), mCitrine (FIG. 14B) and FRET (FIG. 14C) in order to examine the interaction between FKBP-label (mCerulean)-FT and FRB-label (mCitrine)-DPS, displayed at high density on a nano-assembly matrix formed from ferritin (FT) protein in HeLa cells, in the presence or absence of a mediator (regulator) material (rapamycin).
Figure 15:
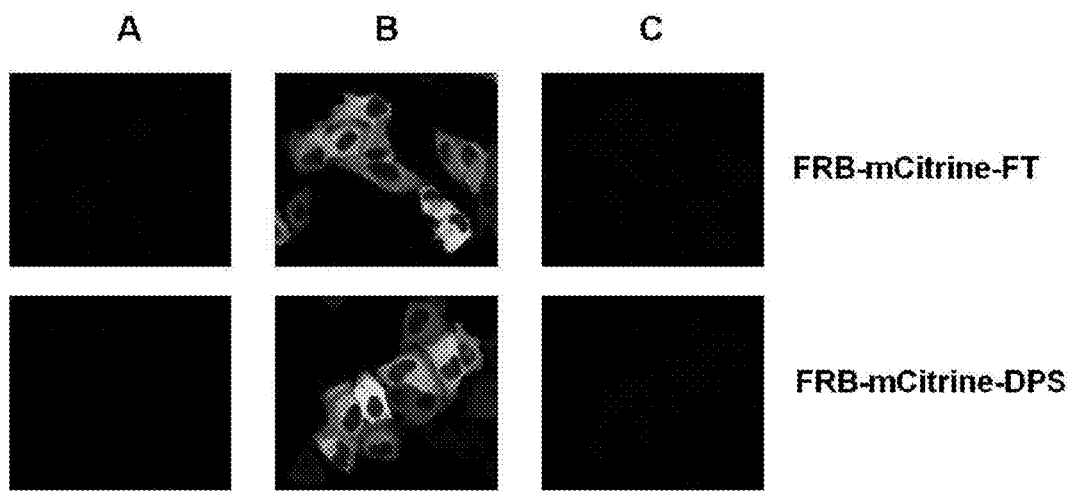
FIG. 15 shows the results of imaging mCerulean (FIG. 15A), mCitrine (FIG. 15B) and FRET (FIG. 15C) in order to examine FRB-label (mCitrine)-FT displayed at high density on a nano-assembly matrix formed from ferritin (FT) protein and DPS protein in HeLa cells. FRET is not imaged because there is no interaction.

The cells were imaged before and after treatment with 250 nM of rapamycin (Calbiochem), and the results of the imaging are shown in FIGS. 13 and 14. As a result, as shown in FIGS. 13 and 14, the intensity of the FRET signal detected greatly increased to the highest possible level ("high") in the case of treatment with the mediator (regulator) rapamycin compared to the case in which the cells were not treated with rapamycin. Thus, the great increase in FRET signal caused by the FKBP-FRB interaction in the nano-assembly matrix was observed.

Example 4: Analysis of Energy Signal Transfer Caused by FKBP-FRB Interaction in Nano-Assembly Matrix after Intracellular Expression of FKBP(F36M)2-mCerulean-FT and FRB-mCitrine-DPS Fusion Proteins A recombinant gene based on pcDNA 3.1 was constructed which can express fusion proteins, obtained by fusing the first mediator (regulator) FKBP(F36M)2, the FRB protein domain and the fluorescent proteins mCerulean and mCitrine to the N-terminal end of ferritin (FT) protein and DPS protein, in mammalian cells by CMV promoter.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins.

For imaging of the incubated cells, the culture medium was changed from 10% FBS-containing DMEM (Gibco) to OPTI-MEM (Gibco), and then the cells were imaged with a confocal microscope (ZEISS, LSM710).

Figure 16:
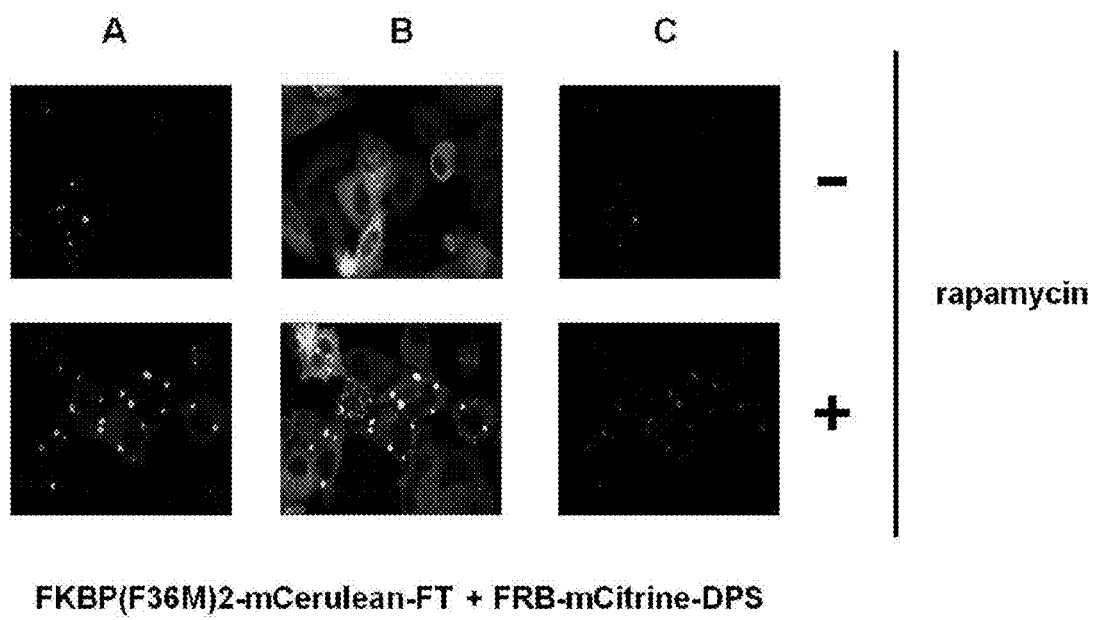
FIG. 16 shows the results of imaging mCerulean (FIG. 14A), mCitrine (FIG. 14B) and FRET (FIG. 14C) in order to examine the interaction between FKBP-label (mCerulean)-FT, displayed at high density on a nano-assembly matrix formed from ferritin (FT) protein and the first mediator (regulator) material FKBP(F36M)2 in HeLa cells, and FRB-label (mCitrine)-DPS displayed at high density on nano-assembly unit matrix (nano-sized unit matrices) of DPS protein, in the presence or absence of a second mediator (regulator) material (rapamycin).

The cells were imaged before and after treatment with 250 nM of rapamycin (Calbiochem), and the results of the imaging are shown in FIG. 16. As a result, as shown in FIG. 16, the intensity of the FRET signal detected greatly increased to the highest possible level ("high") in the case of treatment with the second mediator (regulator) rapamycin compared to the case in which the cells were not treated with rapamycin. Thus, the great increase in FRET signal caused by the FKBP-FRB interaction in the nano-assembly matrix was observed.

Example 5: Analysis of Energy Signal Transfer Caused by FKBP-FRB Interaction in Nano-Assembly Matrix after Intracellular Expression of FRB-mCitirine-FT and FKBP-mCerulean Fusion Proteins A recombinant gene based on pcDNA 3.1 was constructed which can express fusion proteins, obtained by fusing either the FRB protein domain and the fluorescent protein mCitrine or the FKBP protein domain and the fluorescent protein mCerulean to the N-terminal end of ferritin (FT) protein and DPS protein, in mammalian cells by CMV promoter.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins.

For imaging of the incubated cells, the culture medium was changed from 10% FBS-containing DMEM (Gibco) to OPTI-MEM (Gibco), and then the cells were imaged with a confocal microscope (ZEISS, LSM710).

Figure 17:
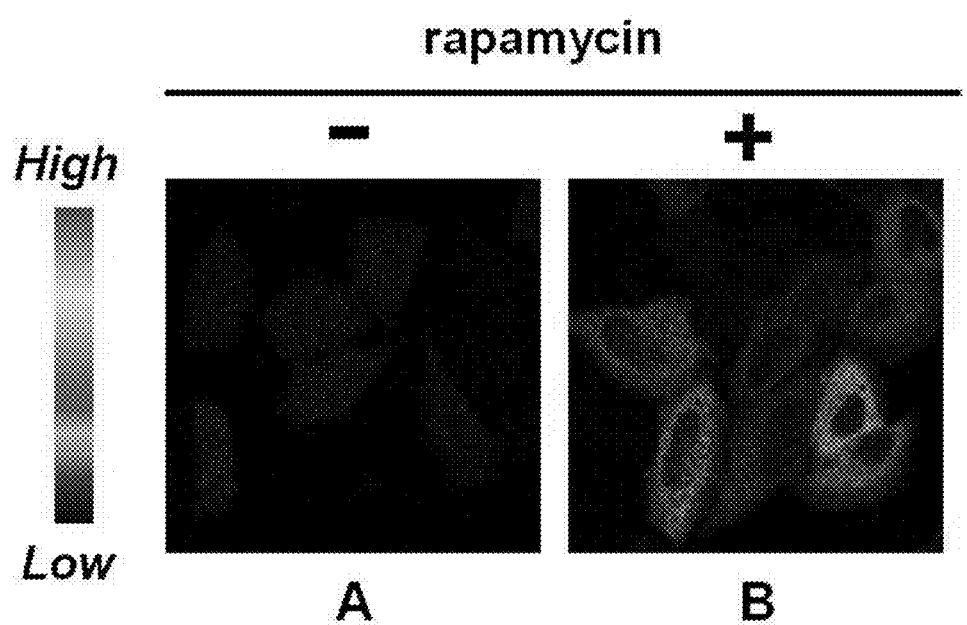
FIG. 17 is a set of photographs showing the results of quantitative FRET analysis of the interaction between FRB-label (mCitrine)-FT and FKBP-label (mCerulean), displayed at high density on nano-assembly unit matrix of ferritin (FT) protein in HeLa cells, in the presence or absence of a mediator (regulator) material (rapamycin).
Figure 18:
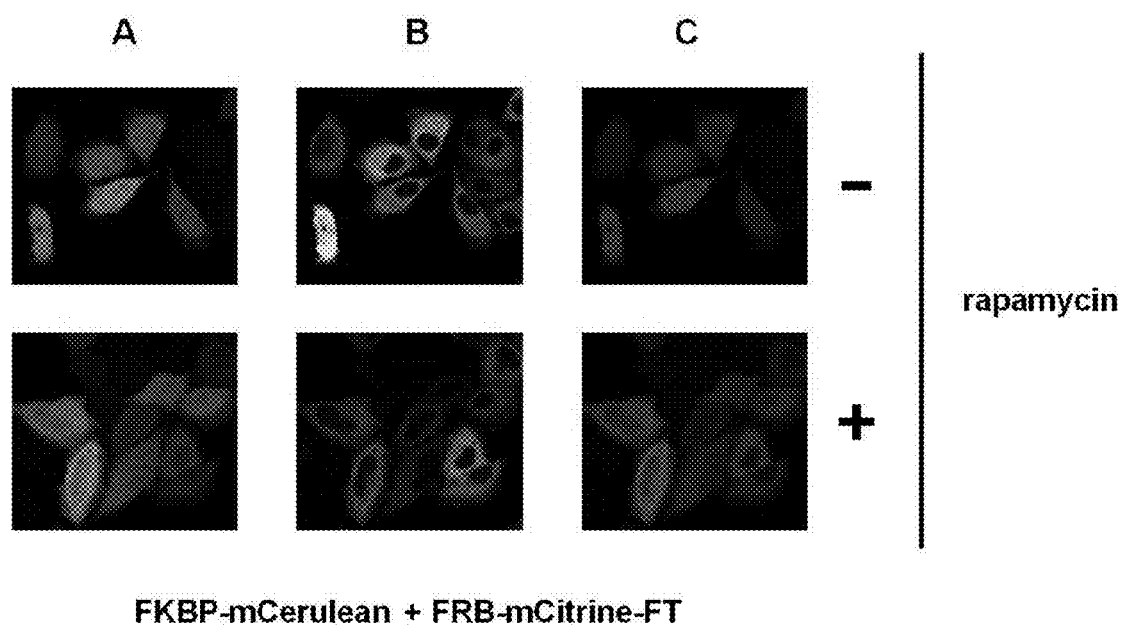
FIG. 18 shows the results of imaging mCerulean (FIG. 18A), mCitrine (FIG. 18B) and FRET (FIG. 18C) in order to examine the interaction between FRB-label (mCitrine)-FT and FKBP-label (mCerulean), displayed at high density on nano-assembly unit matrix of ferritin (FT) protein in HeLa cells, in the presence or absence of a mediator (regulator) material (rapamycin).

The cells were imaged before and after treatment with 250 nM of rapamycin (Calbiochem), and the results of the imaging are shown in FIGS. 17 and 18. As a result, as shown in FIGS. 17 and 18, the intensity of the FRET signal detected greatly increased to the highest possible level ("high") in the case of treatment with the second mediator (regulator)

rapamycin compared to the case in which the cells were not treated with rapamycin. Thus, the great increase in FRET signal caused by the FKBP-FRB interaction in the nano-assembly matrix was observed.

Example 6: Analysis of Energy Signal Transfer Caused by FKBP-FRB Interaction in Nano-Assembly Matrix after Intracellular Expression of FKBP-mCerulean-FT and FRB-mCitirine Fusion Proteins A recombinant gene based on pcDNA 3.1 was constructed which can express fusion proteins, obtained by fusing either the FKBP protein domain and the fluorescent protein mCerulean or the FRB protein domain and the fluorescent protein mCitrine to the N-terminal end of ferritin (FT) protein, in mammalian cells by CMV promoter.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins.

For imaging of the incubated cells, the culture medium was changed from 10% FBS-containing DMEM (Gibco) to OPTI-MEM (Gibco), and then the cells were imaged with a confocal microscope (ZEISS, LSM710).

Figure 19:
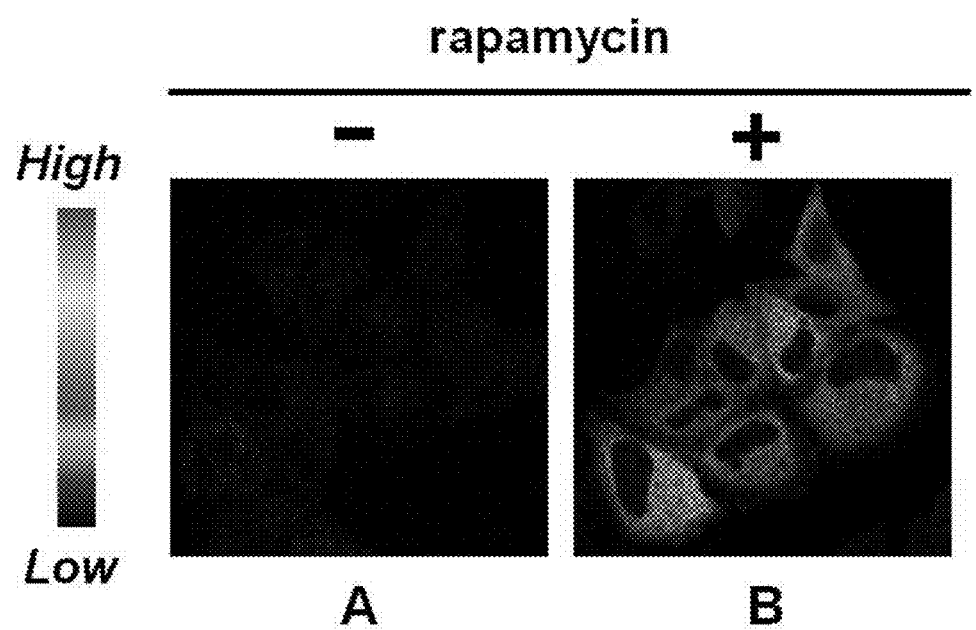
FIG. 19 is a set of photographs showing the results of quantitative FRET analysis of the interaction between FKBP-label (mCerulean)-FT and FRB-label (mCitrine), displayed at high density on nano-assembly unit matrix of ferritin (FT) protein in HeLa cells, in the presence or absence of a mediator (regulator) material (rapamycin).
Figure 20:
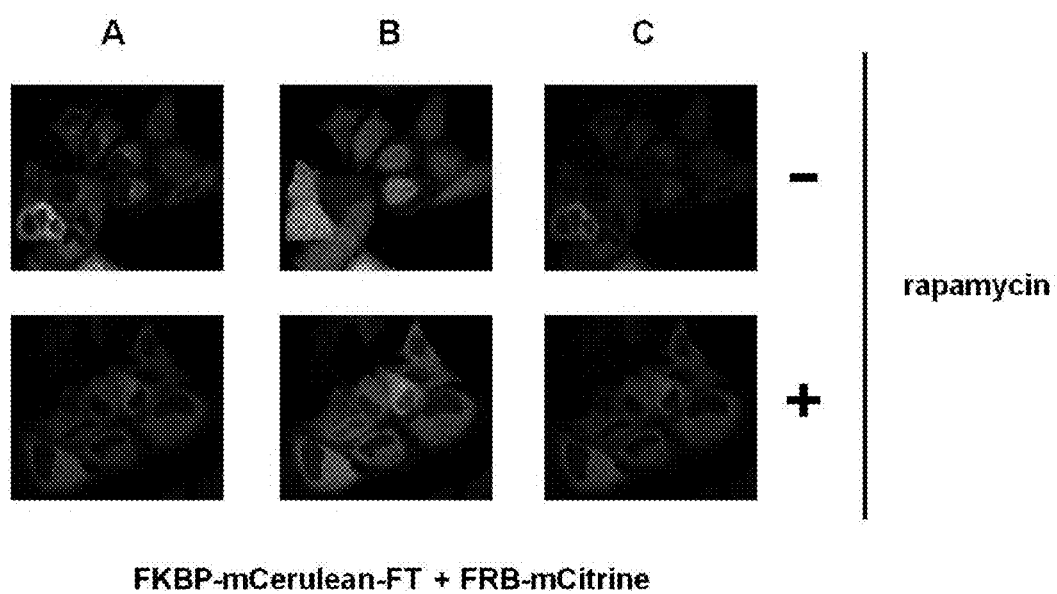
FIG. 20 shows the results of imaging mCerulean (FIG. 20A), mCitrine (FIG. 20B) and FRET (FIG. 20C) in order to examine the interaction between FKBP-label (mCerulean)-FT and FRB-label (mCitrine), displayed at high density on nano-assembly unit matrix of ferritin (FT) protein in HeLa cells, in the presence or absence of a mediator (regulator) material (rapamycin).

The cells were imaged before and after treatment with 250 nM of rapamycin (Calbiochem), and the results of the imaging are shown in FIGS. 19 and 20. As a result, as shown in FIGS. 19 and 20, the intensity of the FRET signal detected greatly increased to the highest possible level ("high") in the case of treatment with the mediator (regulator) rapamycin compared to the case in which the cells were not treated with rapamycin. Thus, the great increase in FRET signal caused by the FKBP-FRB interaction in the nano-assembly matrix was observed.

Example 7: Analysis of Energy Signal Transfer Caused by FKBP-FRB Interaction in Nano-Assembly Matrix after Intracellular Expression of FKBP-mCerulean and FRB-mCitirine-DPS Fusion Proteins A recombinant gene based on pcDNA 3.1 was constructed which can express fusion proteins, obtained by fusing either the FKBP protein domain and the fluorescent protein mCerulean or the FRB protein domain and the fluorescent protein mCitrine to the N-terminal end of DPS protein, in mammalian cells by CMV promoter.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins.

For imaging of the incubated cells, the culture medium was changed from 10% FBS-containing DMEM (Gibco) to OPTI-MEM (Gibco), and then the cells were imaged with a confocal microscope (ZEISS, LSM710).

Figure 21:
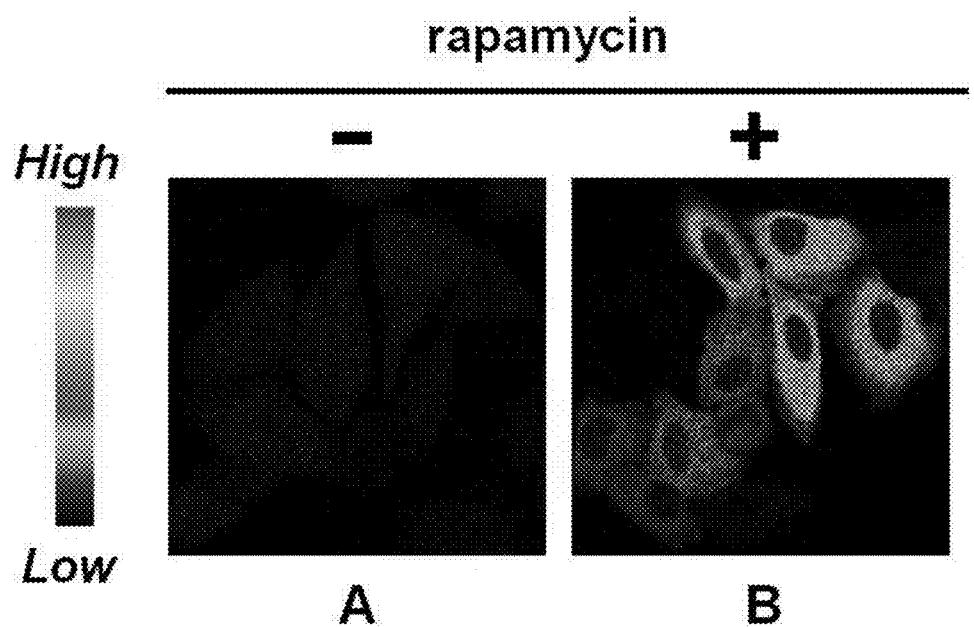
FIG. 21 is a set of photographs showing the results of quantitative FRET analysis of the interaction between FRB-label (mCitrine)-DPS and FKBP-label (mCerulean), displayed at high density on nano-assembly unit matrix of DPS protein in HeLa cells, in the presence or absence of a mediator (regulator) material (rapamycin).
Figure 22:
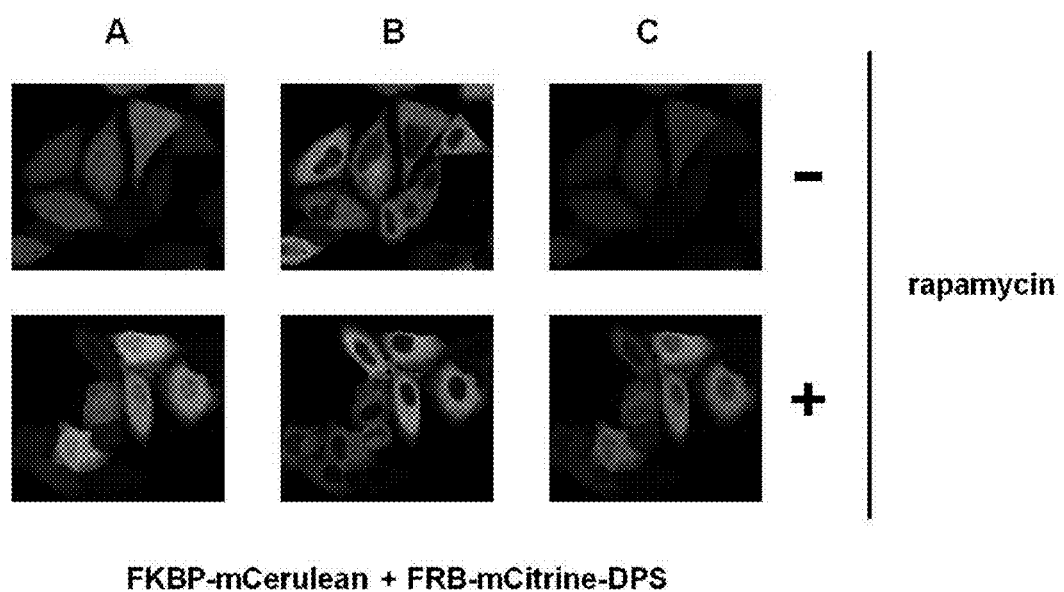
FIG. 22 shows the results of imaging mCerulean (FIG. 22A), mCitrine (FIG. 22B) and FRET (FIG. 22C) in order to examine the interaction between FRB-label (mCitrine)-DPS and FKBP-label (mCerulean), displayed at high density on nano-assembly unit matrix of DPS protein in HeLa cells, in the presence or absence of a mediator (regulator) material (rapamycin).

The cells were imaged before and after treatment with 250 nM of rapamycin (Calbiochem), and the results of the imaging are shown in FIGS. 21 and 22. As a result, as shown in FIGS. 21 and 22, the intensity of the FRET signal detected greatly increased to the highest possible level ("high") in the case of treatment with the mediator (regulator) rapamycin compared to the case in which the cells were not treated with rapamycin. Thus, the great increase in FRET signal caused by the FKBP-FRB interaction in the nano-assembly matrix was observed.

Example 8: Quantitative Analysis of Energy Signal Transfer Caused by FKBP-FRB Interaction in Nano-Assembly Matrix, at Second Intervals, after Intracellular Expression of FRB-ECFP-FT and FKBP-EYFP Fusion Proteins A recombinant gene based on pcDNA 3.1 was constructed which can express fusion proteins, obtained by fusing either the FRB protein domain and the fluorescent protein ECFP or the FKBP protein domain and the fluorescent protein EYFP to the N-terminal end of ferritin (FT) protein, in mammalian cells by CMV promoter.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins.

Figure 23:
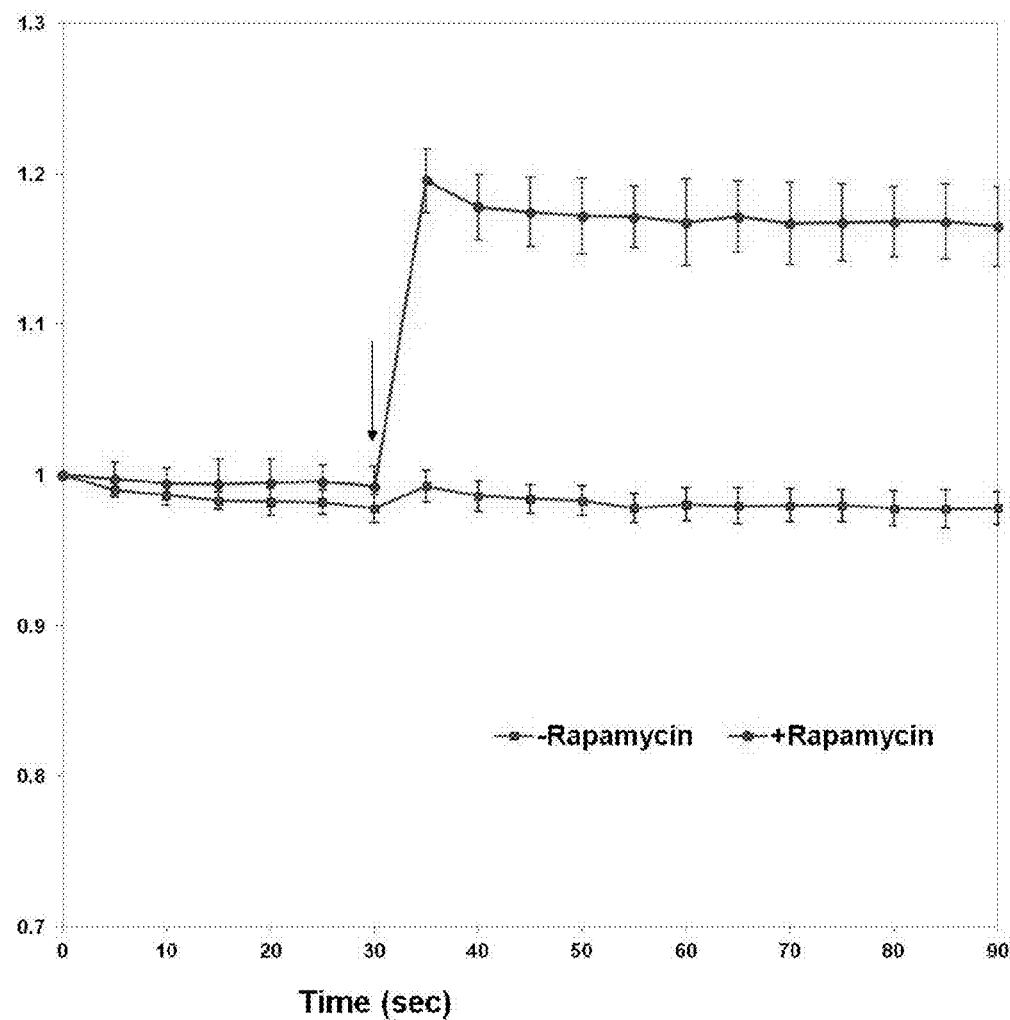
FIG. 23 is a set of photographs showing the results of second-interval quantitative FRET analysis of the interaction between FRB-label (ECFP)-FT and FKBP-label (EYFP), displayed at high density on nano-assembly unit matrix of ferritin (FT) protein in HeLa cells, in the presence or absence of a mediator (regulator) material (rapamycin).

FRET images of the cells were obtained using a confocal microscope (ZEISS, LSM710) at second intervals before and after treatment with rapamycin (Calbiochem) and were quantitatively analyzed, and the results of the analysis are shown in FIG. 23. The arrow in FIG. 23 indicates bleaching of the FRET acceptor. As shown in FIG. 23, the intensity of the FRET signal greatly increased in the case of treatment with the mediator (regulator) rapamycin compared to the case in which the cells were not treated with rapamycin. Thus, the great increase in FRET signal caused by the FKBP-FRB interaction in the nano-assembly matrix was observed.

Example 9: Quantitative Analysis of Energy Signal Transfer Caused by DHFR-Methotrexate Interaction in Nano-Assembly Matrix, at Second Intervals, after Intracellular Expression of DHFR-mRFP-FT and FRB-FKBP-mCerulean-FT Fusion Proteins and Treatment with Methotrexate-Fluorescein Drug A recombinant gene based on pcDNA 3.1 was constructed which can express fusion proteins, obtained by fusing the DHFR or FRB-FKBP protein domain and the fluorescent protein mRFP or mCerulean to the N-terminal end of ferritin (FT) protein, in mammalian cells by CMV promoter. A fluorescent drug (Invitrogen) comprising drug methotrexate conjugated to fluorescein was purchased.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins. The cells were treated with 10 uM methotrexate-fluorescein drug.

Figure 24:
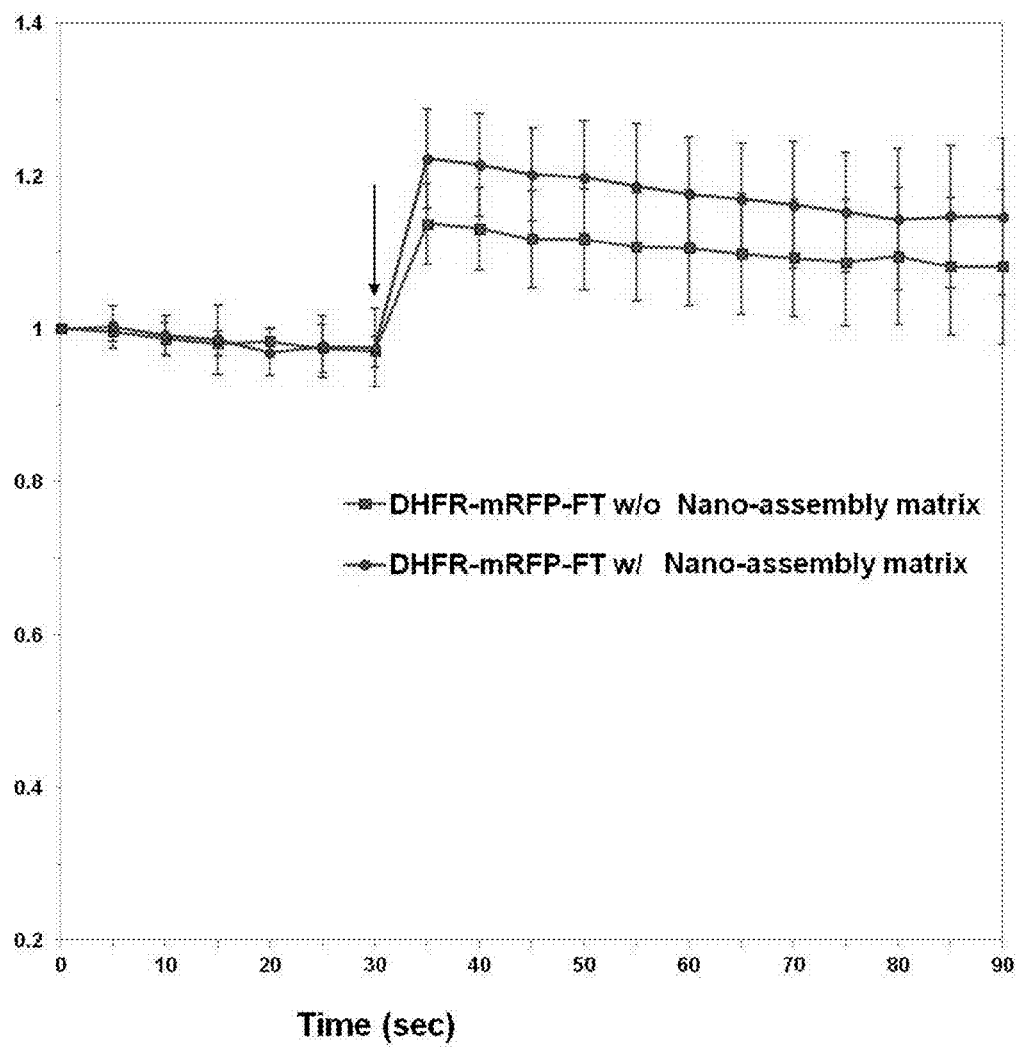
FIG. 24 is a set of photographs showing the results of second-interval quantitative FRET analysis of the interaction between DHFR-label (mRFP)-FT and methotrexate-label (fluorescein), displayed at high density on a nano-assembly matrix formed from ferritin (FT) protein in HeLa cells, in the presence or absence of a mediator (regulator) material (rapamycin).

FRET images of the cells were obtained using a confocal microscope (ZEISS, LSM710) at second intervals before and after treatment with rapamycin (Calbiochem) and were quantitatively analyzed, and the results of the analysis are shown in FIG. 24. The arrow in FIG. 24 indicates bleaching of the FRET acceptor. As shown in FIG. 24, in the case in which the cells were treated with the mediator (regulator) rapamycin, the intensity of the FRET signal greatly increased because DHFR molecules were displayed on the nano-assembly matrix at high density, compared to the case in which the cells were not treated with rapamycin. Thus, the great increase in FRET signal caused by the FKBP-FRB interaction in the nano-assembly matrix was observed.

Example 10: Quantitative Analysis of Energy Signal Transfer Caused by FKBP-FRB Interaction in Nano-Assembly Matrix, at Second Intervals, after Intracellular Expression of FKBP-mRFP-FT and FRB-EGFP Fusion Proteins A recombinant gene based on pcDNA 3.1 was constructed which can express fusion proteins, obtained by fusing either the FKBP protein domain and the fluorescent protein mRFP or the FRB protein domain and the fluorescent protein EGFP to the N-terminal end of ferritin (FT) protein, in mammalian cells by CMV promoter.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins.

Figure 25:
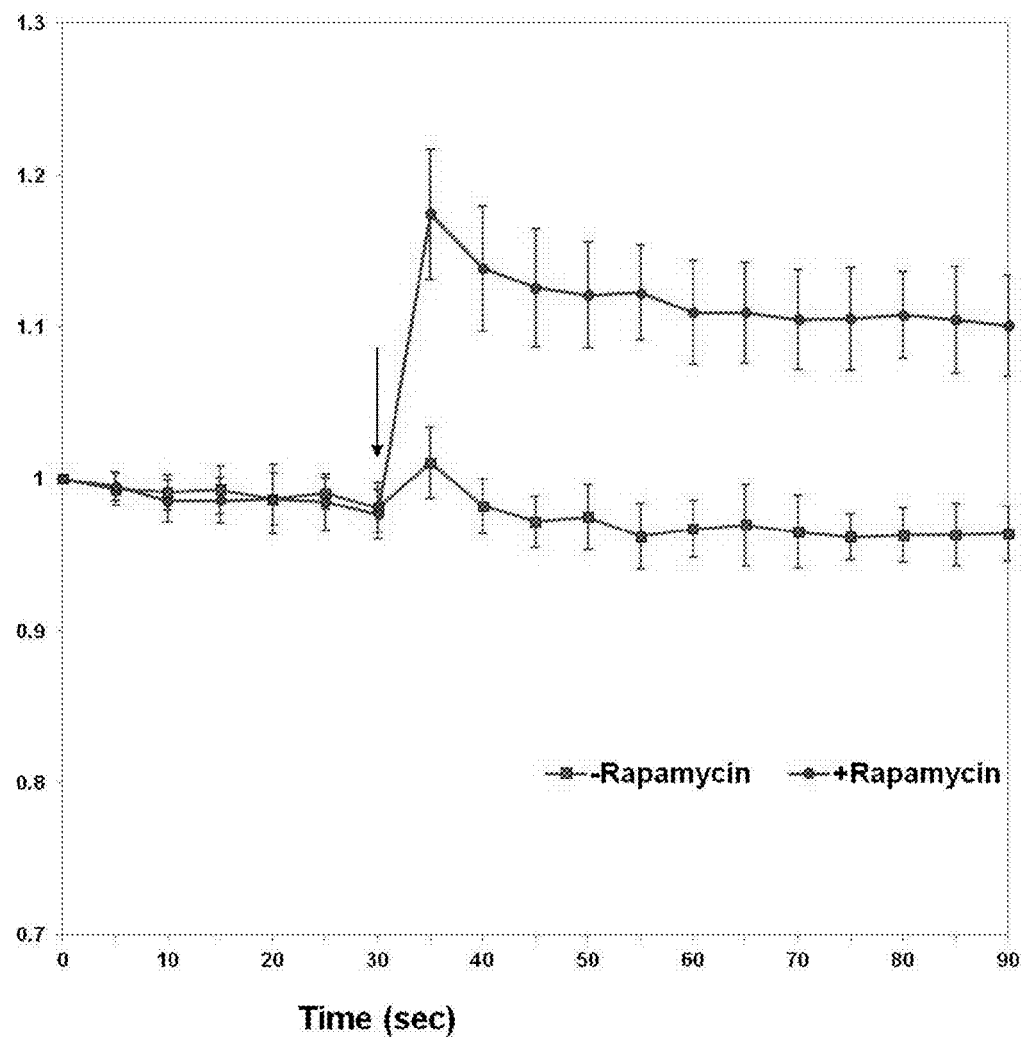
FIG. 25 is a set of photographs showing the results of second-interval quantitative FRET analysis of the interaction between FKBP-label (mRFP)-FT and FRB-label (EGFP), displayed at high density on nano-assembly unit matrix of ferritin (FT) protein in HeLa cells, in the presence or absence of a mediator (regulator) material (rapamycin).

FRET images of the cells were obtained using a confocal microscope (ZEISS, LSM710) at second intervals before and after treatment with rapamycin (Calbiochem) and were quantitatively analyzed, and the results of the analysis are shown in FIG. 25. The arrow in FIG. 25 indicates bleaching of the FRET acceptor. As shown in FIG. 25, the intensity of the FRET signal greatly increased in the case of treatment with the mediator (regulator) rapamycin compared to the case in which the cells were not treated with rapamycin. Thus, the great increase in FRET signal caused by the FKBP-FRB interaction in the nano-assembly matrix was observed.

Example 11: Quantitative Analysis of Energy Signal Transfer Caused by IkBa-RelA Interaction in Nano-Assembly Analysis, at Second Intervals, after Intracellular Expression of IkBa-CFP-FT and RelA-YFP Fusion Proteins A recombinant gene based on pcDNA 3.1 was constructed which can express fusion proteins, obtained by fusing either the IkBa protein and the fluorescent protein CFP or the RelA protein and fluorescent protein CFP to the N-terminal end of ferritin (FT) protein, in mammalian cells by CMV promoter.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins.

Figure 26:
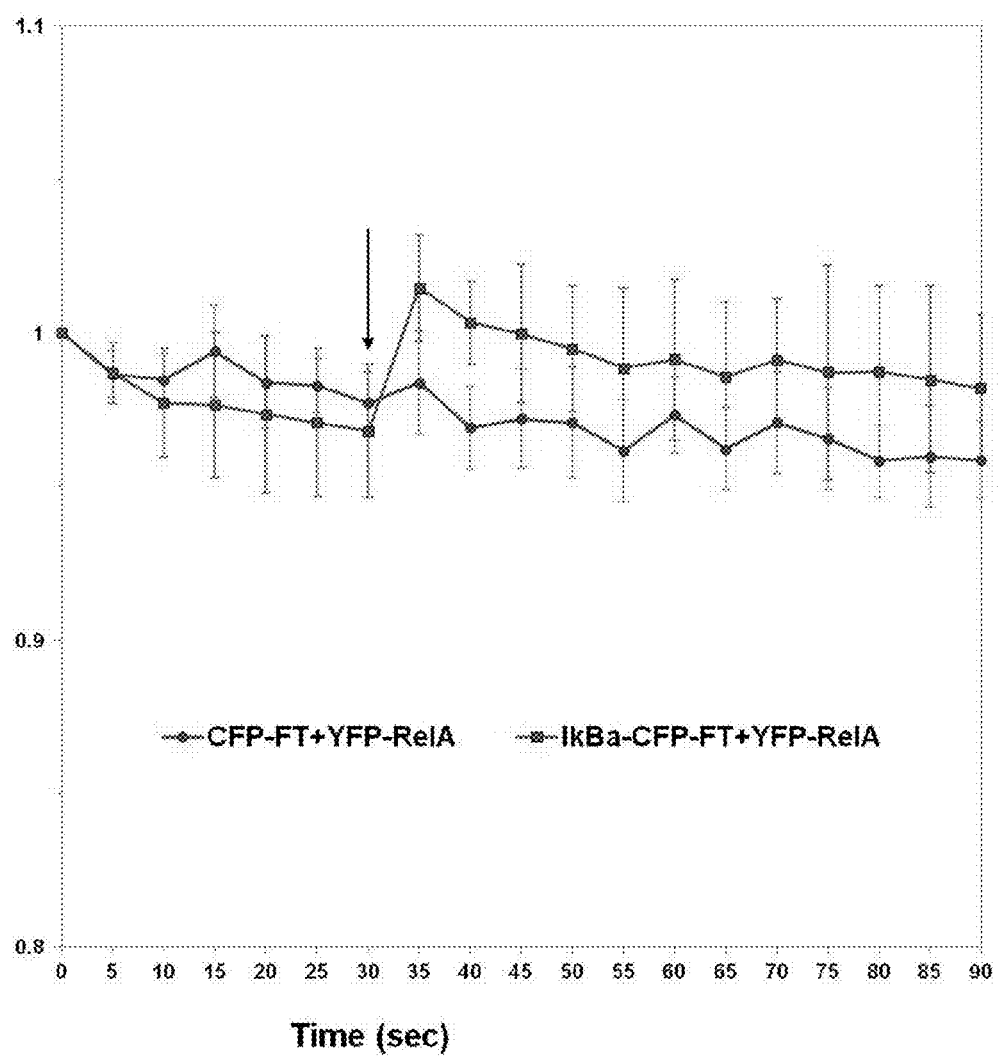
FIG. 26 is a set of photographs showing the results of second-interval quantitative FRET analysis of the interactions between label (CFP)-FT and RelA-label (YFP) and between IkBa-label (CFP)-FT and RelA-label (YFP), displayed at high density on nano-assembly unit matrix of ferritin (FT) protein in HeLa cells.

FRET images of the cells were obtained using a confocal microscope (ZEISS, LSM710) at second intervals under two different expression conditions and were quantitatively analyzed, and the results of the analysis are shown in FIG. 26. The arrow in FIG. 26 indicates bleaching of the FRET acceptor. As shown in FIG. 26, a FRET signal was detected as a result of the interaction between IkBa and RelA. Thus, the great increase in FRET signal caused by the IkBa-RelA interaction in the nano-assembly matrix was observed.

Example 12: Quantitative Analysis of the Distribution, Intensity, Size and Number of Signals of Nano-Assembly Matrix Formation Caused by FKBP-FRB Interaction, at Minute Intervals, after Intracellular Expression of FRB-FKBP-mCerulean-FT Fusion Protein A recombinant gene based on pcDNA 3.1 was constructed which can express a fusion protein, obtained by fusing the FRB-FKBP protein domain and the fluorescent protein mCerulean to the N-terminal end of ferritin (FT) protein, in mammalian cells by CMV promoter.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion protein.

Figure 27:
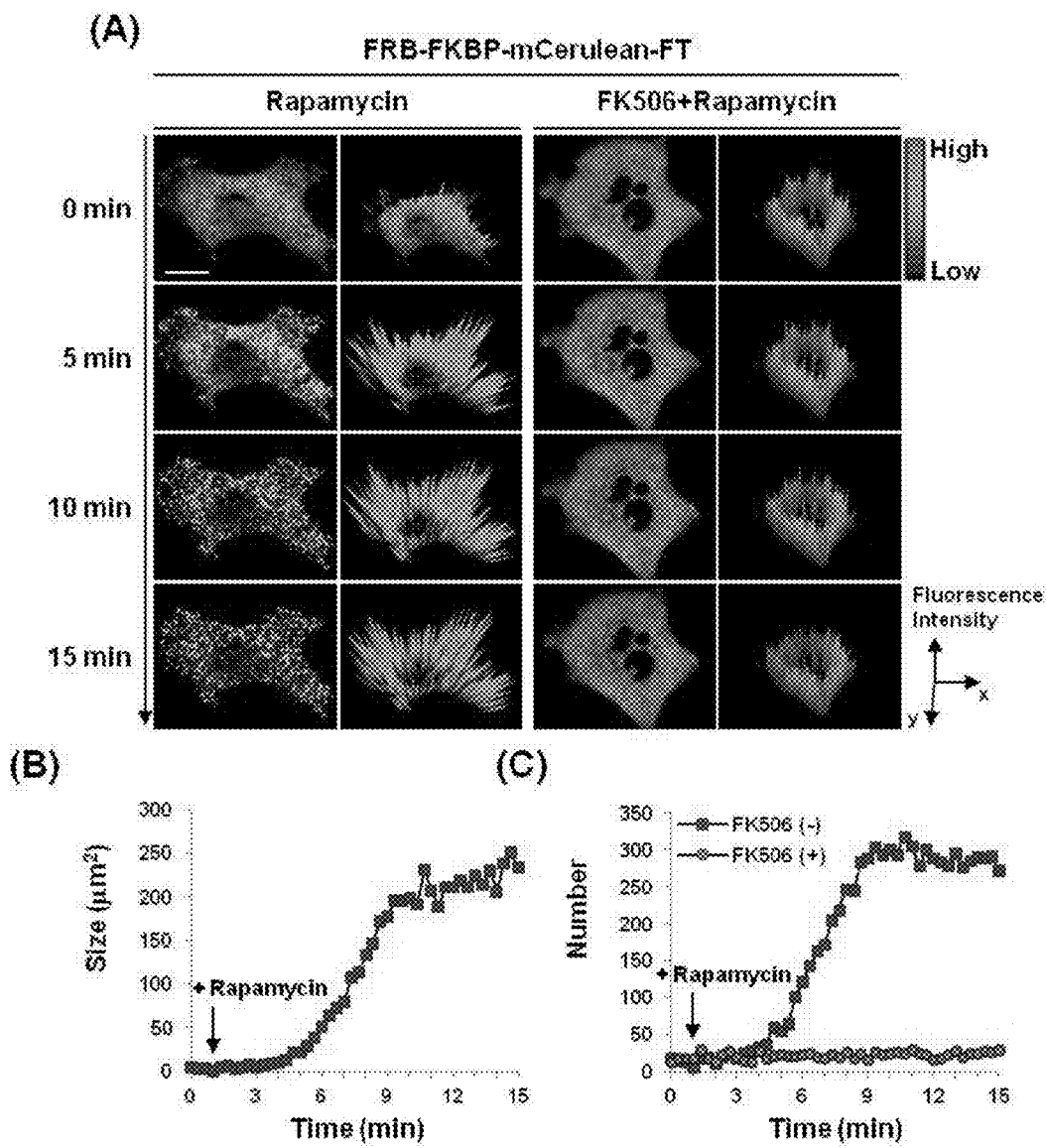
FIG. 27 shows the results of minute-interval quantitative analysis of the distribution, intensity, size and number of signals of nano-assembly matrix formation caused by FRB-FKBP-label (mCerulean)-FT, displayed at high density on nano-assembly unit matrix of ferritin (FT) protein in HeLa cells, in the presence or absence of an inhibitor (FK506) of a mediator (regulator) material.

Images of the cells were obtained using a confocal microscope (ZEISS, LSM710) before and after treatment with rapamycin (Calbiochem) and were quantitatively analyzed, and the results of the analysis are shown in FIG. 27. The distribution and intensity (FIG. 27A), size (FIG. 27B) and number (27C) of nano-assembly matrix formation signals were quantified at minute intervals, and as a result, the great increase in patterns and signals of nano-assembly matrix formation caused by the FKBP-FRB interaction was observed. For example, the difference in S/N (signal/noise) ratio reached several hundred times.

Example 13: Quantitative Analysis of Change in Intensity and the Like of Signals of Interaction Between DHFR and Methotrexate-Fluorescein after Intracellular Expression of FRB-FKBP-mCerulean-FT and DHFR-mRFP-FT Fusion Proteins A recombinant gene based on pcDNA 3.1 was constructed which can express fusion proteins, obtained by fusing either the FRB-FKBP protein domain and the fluorescent protein mCerulean or the DHFR protein and the fluorescent protein mRFP to the N-terminal end of ferritin (FT) protein, in mammalian cells by CMV promoter.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins and were treated with a methotrexate-fluorescein drug.

Figure 28:
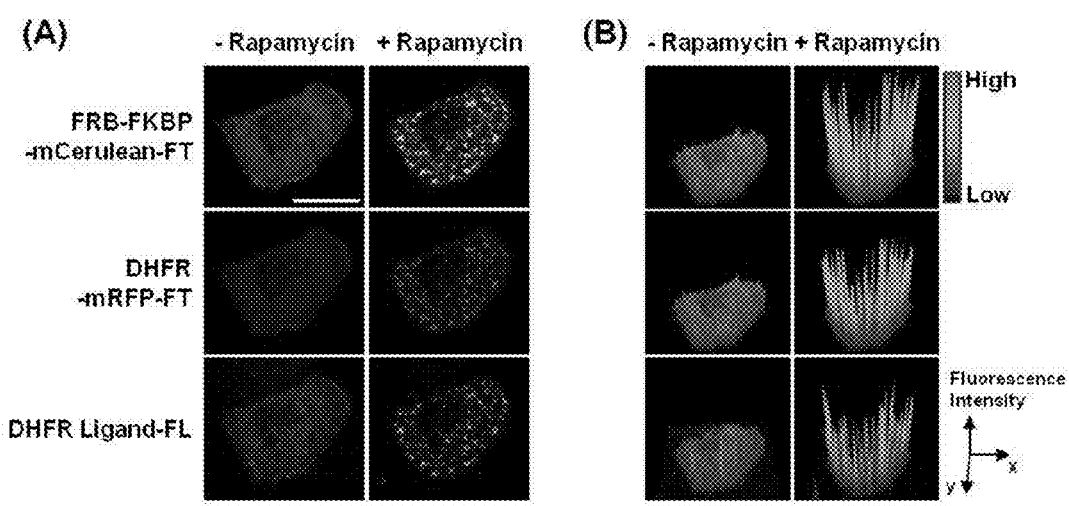
FIG. 28 shows the results of quantitative analysis of the change in signal of interaction between DHFR and methotrexate-label (fluorescein) caused by FRB-FKBP-label (mCerulean)-FT and DHFR-label (mRFP)-FT, displayed at high density on a nano-assembly matrix of ferritin (FT) protein in HeLa cells, in the presence or absence of a mediator (regulator) material (rapamycin).

Images of the cells were obtained using a confocal microscope (ZEISS, LSM710) before and after treatment with rapamycin (Calbiochem) and were quantitatively analyzed, and the results of the analysis are shown in FIG. 28. The distribution (FIG. 28A) and intensity (FIG. 28B) of fluorescence signals caused by the interaction between DHFR and methotrexate-fluorescin were quantitatively analyzed, and as a result, the great increase in the patterns and signals of the interaction was observed.

Example 14: Quantitative Analysis of Change in Intensity and the Like of Interaction Between IkBa and YFP-RelA after Intracellular Expression of FRB-/FKBP-mCerulean-FT and IkBa-ECFP-FT Fusion Proteins A recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins and were treated with a methotrexate-fluorescein drug.

Figure 29:
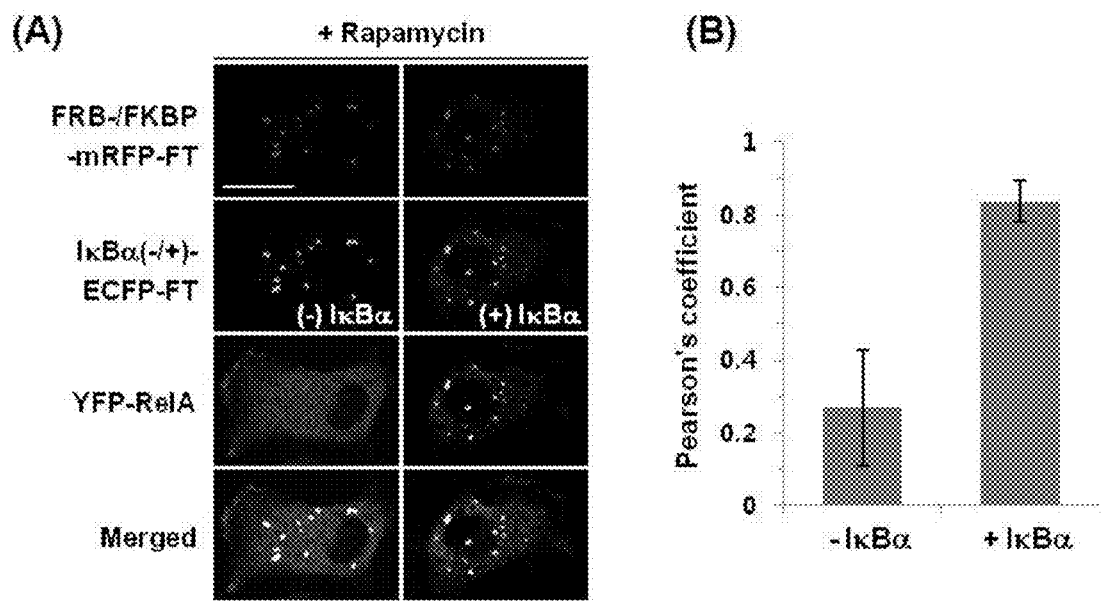
FIG. 29 shows the results of quantitative analysis of the change in signal of interaction between IkBa and RelA-label (YFP) caused by FRB-/FKBP-label (mRFP)-FT and IkBa-label (ECFP)-FT, displayed at high density on a nano-assembly matrix of ferritin (FT) protein in HeLa cells, in the presence or absence of a mediator (regulator) material (rapamycin).

Images of the cells were obtained using a confocal microscope (ZEISS, LSM710) before and after treatment with rapamycin (Calbiochem) and were quantitatively analyzed, and the results of the analysis are shown in FIG. 29. The distribution (FIG. 29A) and position (FIG. 29B) of fluorescence signals caused by the interaction between IkBa and YFP-RelA were quantitatively analyzed, and as a result, the great increase in the patterns and signals of the interaction was observed.

Example 15: Quantitative Analysis of Change in Intensity and the Like of Signals of Interaction Between DHFR and Methotrexate-Fluorescein after Intracellular Expression of FRB-/FKBP-mCerulean-FT and DHFR-mRFP-FT Fusion Proteins A recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins and were treated with a methotrexate-fluorescein drug.

Figure 30:
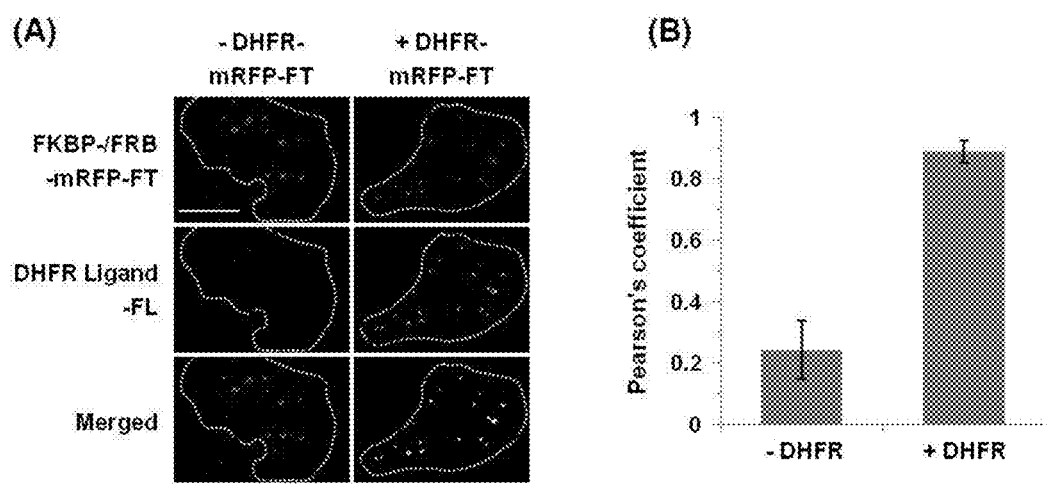
FIG. 30 shows the results of quantitative analysis of the change in signal of interaction between DHFR and methotrexate-label (fluorescein) caused by FKBP-/FRB-label (mRFP)-FT and DHFR-label (mRFP)-FT, displayed at high density on a nano-assembly matrix of ferritin (FT) protein in HeLa cells, in the presence or absence of a mediator (regulator) material (rapamycin).

Images of the cells were obtained using a confocal microscope (ZEISS, LSM710) before and after treatment with rapamycin (Calbiochem) and were quantitatively analyzed, and the results of the analysis are shown in FIG. 30. The distribution (FIG. 30A) and position (FIG. 30B) of fluorescence signals caused by the interaction between DHFR and methotrexate-fluorescein were quantitatively analyzed, and as a result, the great increase in the patterns and signals of the interaction was observed.

Example 16: Quantitative Analysis of the Distribution, Intensity, Size and Number of Signals of Nano-Assembly Matrix Formation Caused by FKBP-FRB Interaction, at Minute Intervals, after Intracellular Expression of FKBP(F36M)1~5-mRFP-FT Fusion Protein A recombinant gene based on pcDNA 3.1 was constructed which can express a fusion protein, obtained by fusing the FKBP(F36M)1~5 protein domain and the fluorescent protein mRFP to the N-terminal end of ferritin (FT) protein, in mammalian cells by CMV promoter.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion protein.

Figure 31:
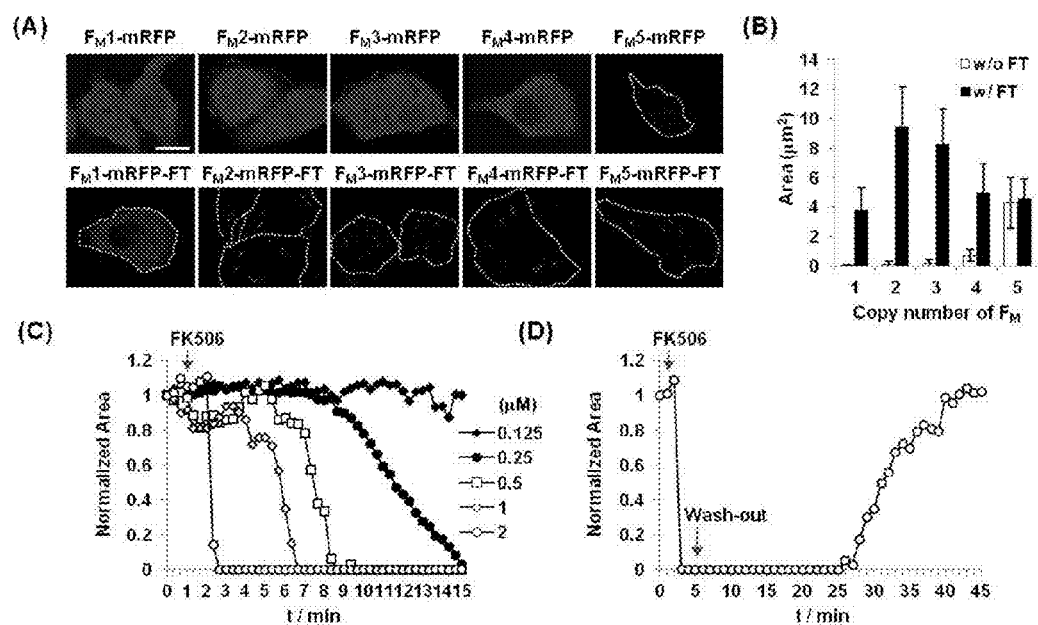
FIG. 31 shows the results of minute-interval quantitative analysis of the changes in intensity and area of nano-assembly matrix formation signal caused by FKBP(F36M)1~5-label (mRFP)-FT, displayed at high density on a nano-assembly matrix of ferritin (FT) protein in HeLa cells, in the presence or absence of FK506.

Images of the cells were obtained using a confocal microscope (ZEISS, LSM710) before and after treatment with FK506 and were quantitatively analyzed, and the results of the analysis are shown in FIG. 31. The distribution (FIG. 31A), area as a function of FKBP (F36M) number (FIG. 31B), area according to FK506 treatment (FIG. 31C) and area according to FK506 treatment and removal (FIG. 31D) of signals of nano-assembly matrix formation were quantified at minute intervals, and as a result, the great increase in patterns and signals of nano-assembly matrix formation caused by the FKBP-FRB interaction was observed.

Example 17: Quantitative Analysis of Change and the Like in Intensity and the Like of Signals of FKBP-FRB Interaction after Intracellular Expression of FKBP(F36M)2-mRFP-FT and FRB-EGFP Fusion Proteins A recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins.

Figure 32:
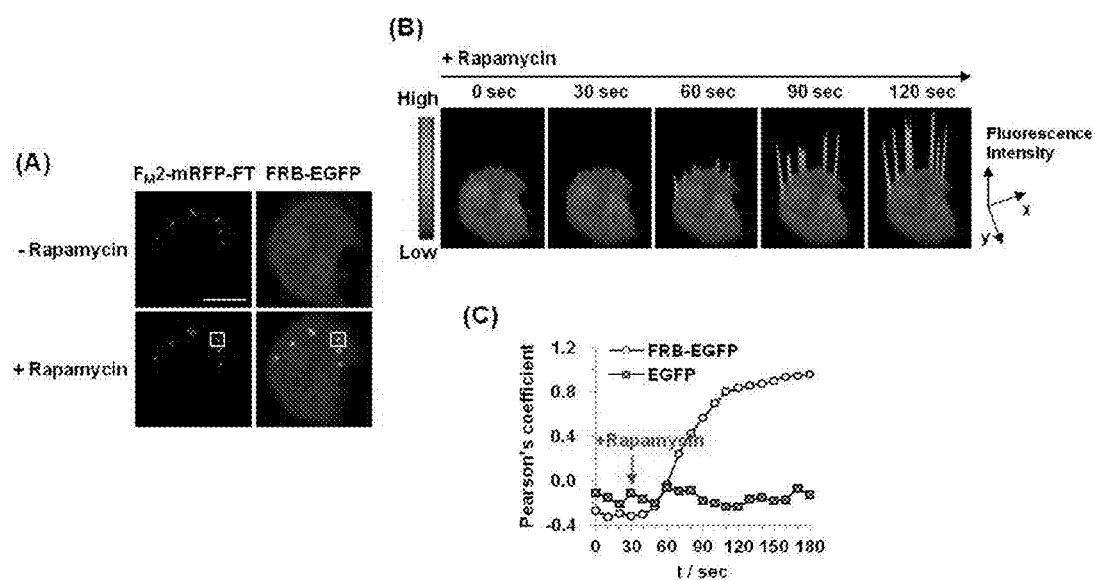
FIG. 32 shows the results of second-interval quantitative analysis of the change in signal of FRB-FKBP interaction caused by FKBP(F36M)2-label (mRFP)-FT and FRB-label (EGFP), displayed at high density on a nano-assembly matrix of ferritin (FT) protein in HeLa cells, in the presence or absence of a mediator (regulator) material (rapamycin).

Images of the cells were obtained using a confocal microscope (ZEISS, LSM710) before and after treatment with rapamycin (Calbiochem) and were quantitatively analyzed, and the results of the analysis are shown in FIG. 32. The distribution (FIG. 32A), intensity (FIG. 32B) and position (FIG. 30C) of fluorescence signals caused by the interaction between FKBP and FRB were quantified, and as a result, the great increase in the patterns and signals of the interaction was observed.

Example 18: Quantitative Analysis of Intensity and the Like of Signals of IkBa-RelA Interaction after Intracellular Expression of FKBP(F36M)2-mRFP-FT, IkBa-ECFP-FRB and EYFP-RelA Fusion Proteins A recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins.

Figure 33:
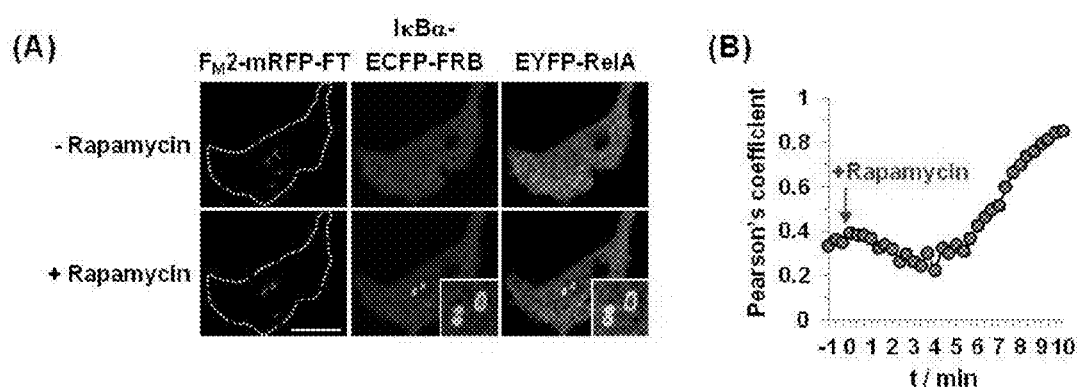
FIG. 33 shows the results of minute-interval quantitative analysis of the change in signal of IkBa-RelA-label (EYFP) interaction caused by FKBP(F36M)2-label (mRFP)-FT and IkBa-label (ECFP)-FRB, displayed at high density on a nano-assembly matrix of ferritin (FT) protein in HeLa cells, in the presence or absence of a mediator (regulator) material (rapamycin).

Images of the cells were obtained using a confocal microscope (ZEISS, LSM710) before and after treatment with rapamycin (Calbiochem) and were quantitatively analyzed, and the results of the analysis are shown in FIG. 33. The distribution (FIG. 33A) and position (FIG. 33B) of fluorescence signals caused by the interaction between IkBa and RelA were quantified, and as a result, the great increase in the patterns and signals of the interaction was observed.

Example 19: Quantitative Analysis of Intensity and the Like of Signals of Interaction Between DHFR and Methotrexate-BodipyFL after Intracellular Expression of FKBP(F36M)2-mRFP-FT and DHFR-mRFP-FT Fusion Proteins A recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion proteins and were treated with a methotrexate-BodipyFL fluorescent drug.

Figure 34:
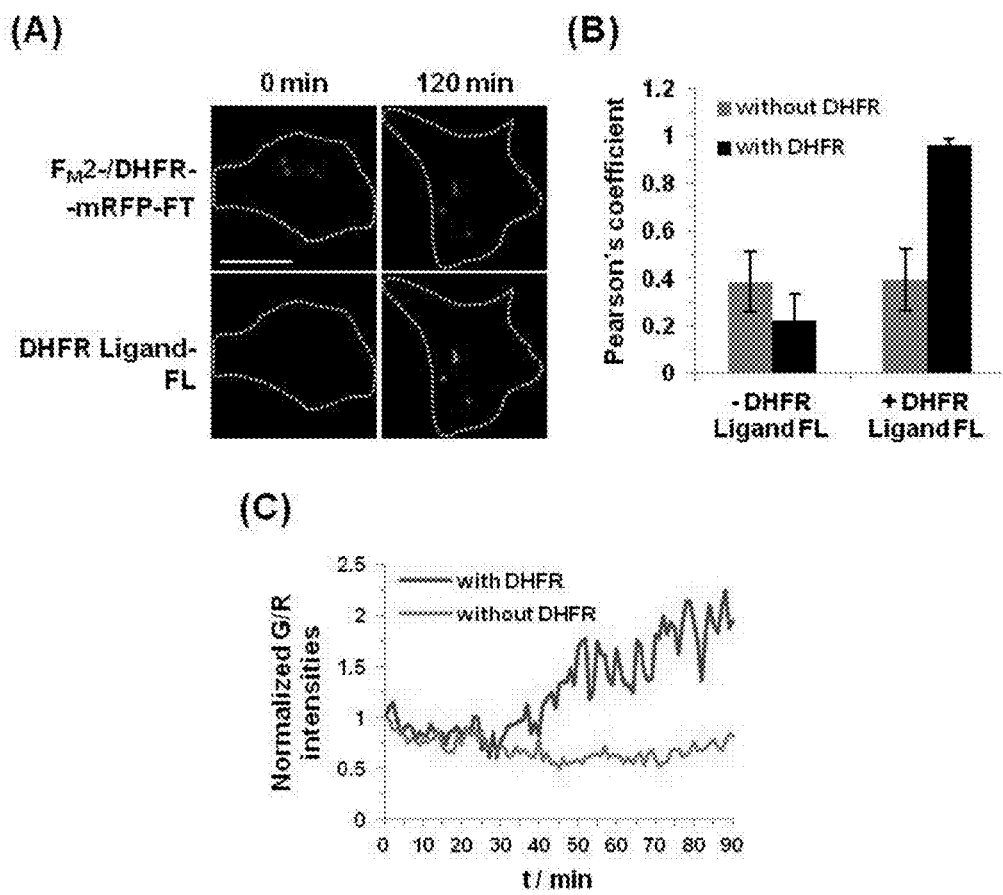
FIG. 34 shows the results of quantitative analysis of the change in signal of DHFR-methotrexate-label (BodipyFL) interaction caused by FKBP(F36M)2-label (mRFP)-FT and DHFR-label (mRFP)-FT, displayed at high density on a nano-assembly matrix of ferritin (FT) protein in HeLa cells, in the presence or absence of a mediator (regulator) material (rapamycin).

Images of the cells were obtained using a confocal microscope (ZEISS, LSM710) before and after treatment with rapamycin (Calbiochem) and were quantitatively analyzed, and the results of the analysis are shown in FIG. 34. The distribution (FIG. 34A), position (FIG. 34B) according to the presence or absence of DHFR and intensity according to the presence or absence of DHFR of fluorescence signals caused by the interaction between DHFR and methotrexate-BodipyFL were quantified, and as a result, the great increase in the patterns and signals of the interaction was observed.

Example 20: Detection and Labeling of Endosome Target Material Using Nano-Assembly Matrix A recombinant protein based on pcDNA 3.1 was constructed which can express a fusion protein, obtained by fusing the RAB protein (RAB5A, RAB7A), the FKBP or FRB protein domain and the fluorescent protein mCerulean to the N-terminal end of ferritin (FT) protein, in mammalian cells by CMV promoter.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion protein.

Figure 35:
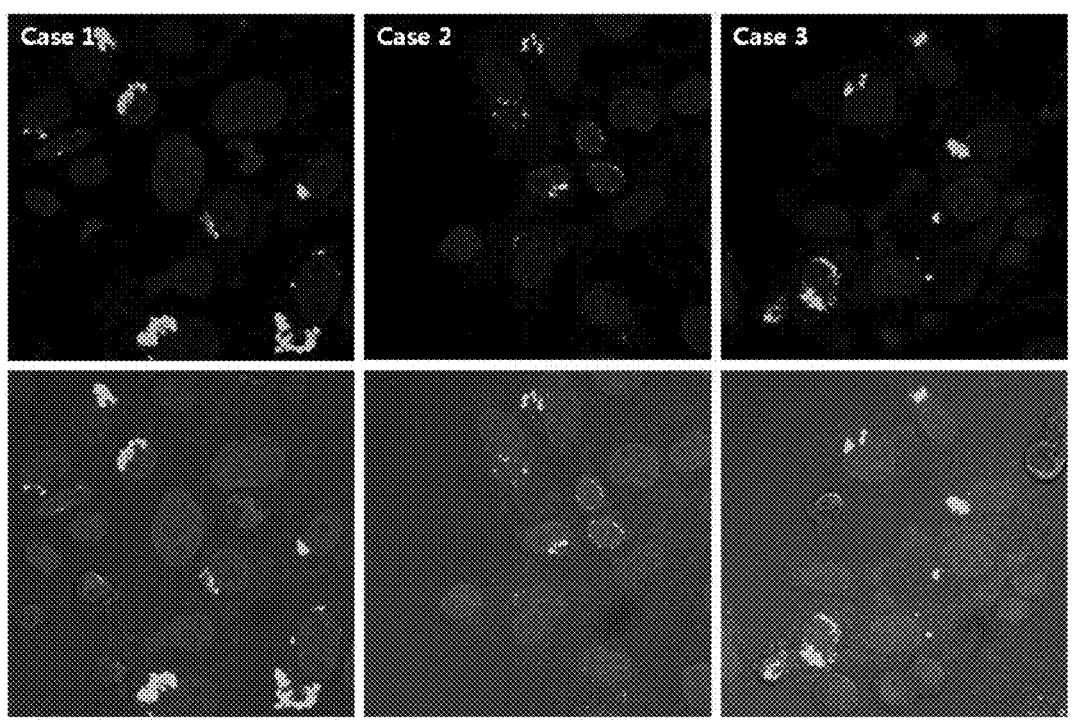
FIG. 35 shows images of an early endosome target material (DAPI nucleus-stained) detected and labeled using an early endosome-interacting material (RAB5A) displayed at high density on a nano-assembly matrix of ferritin (FT) protein in HeLa cells.
Figure 36:
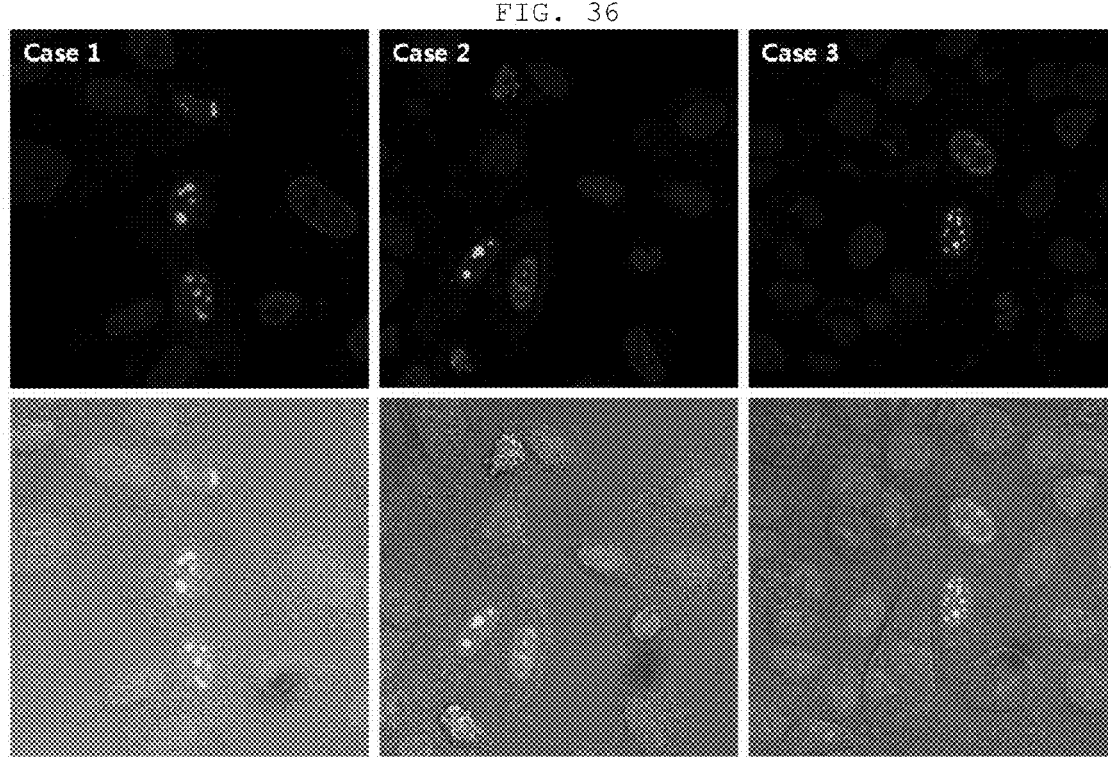
FIG. 36 shows images of a late endosome target material (DAPI nucleus-stained) detected and labeled using a late endosome-interacting material (RAB7A) displayed at high density on a nano-assembly matrix of ferritin (FT) protein in HeLa cells.

Images of the cells were obtained using a confocal microscope (ZEISS, LSM710) after treatment with rapamycin (Calbiochem), and the images are shown in FIGS. 35 and 36. The cells were observed by staining the nuclei with DAPI. As a result, it was shown that early and late endosome target materials were efficiently detected and labeled using the nano-assembly matrix formed by the interaction between FKBP and FRB.

Example 21: Detection and Labeling of Golgi Target Material Using Nano-Assembly Matrix A recombinant protein based on pcDNA 3.1 was constructed which can express a fusion protein, obtained by fusing the Golgi-interacting protein (GALNT2), the FKBP or FRB protein domain and the fluorescent protein mCerulean to the N-terminal end of ferritin (FT) protein, in mammalian cells by CMV promoter.

The recombinant gene was introduced into HeLa cells, cultured in a 4-well LabTek II chamber slide, using Lipofectamine™ LTX. Then, the cells were incubated in a 5% $CO_2$ incubator at 37° C. for 24 hours to express the fusion protein.

Figure 37:
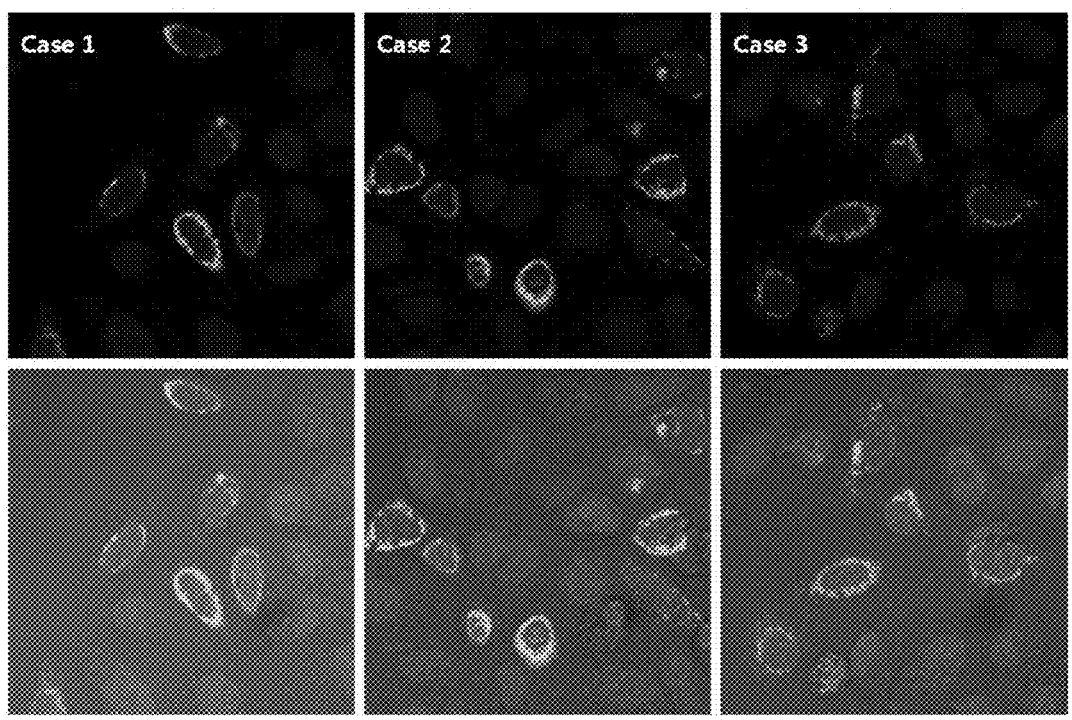
FIG. 37 shows images of a Golgi target material (DAPI nucleus-stained) detected and labeled using a Golgi-interacting material (GALNT2) displayed at high density on a nano-assembly matrix of ferritin (FT) protein in HeLa cells.
Figure 38:
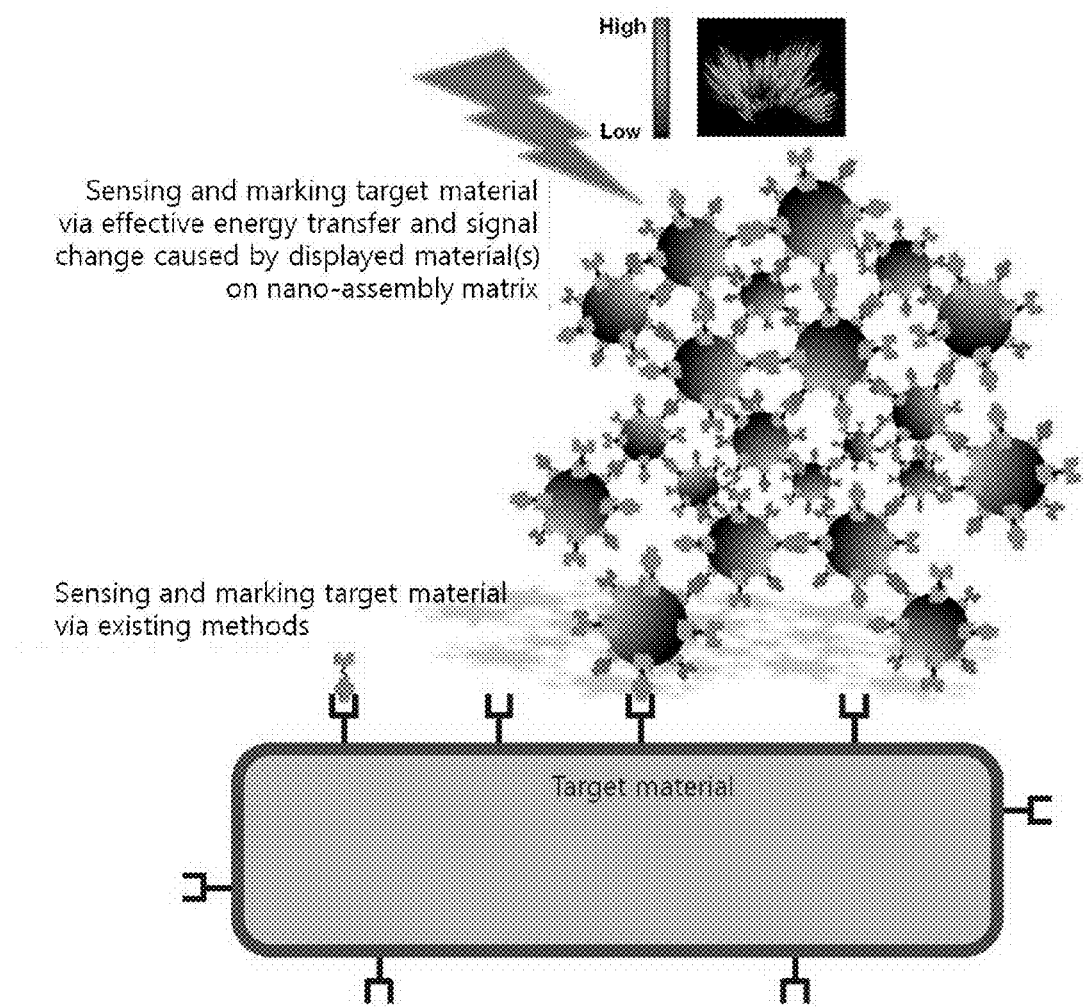
FIG. 38 is a schematic view showing a process of effectively detecting and targeting a target material that interacts with materials displayed on a nano-assembly matrix.

Images of the cells were obtained using a confocal microscope (ZEISS, LSM710) after treatment with rapamycin (Calbiochem), and the images are shown in FIG. 37. The cells were observed by staining the nuclei with DAPI. As a result, it was shown that the Golgi target material was efficiently detected and labeled using the nano-assembly matrix formed by the interaction between FKBP and FRB.

INDUSTRIAL APPLICABILITY

As described above, liRNA according to the present invention has the effect of inhibiting the target gene expression in a manner specific to the sequence of siRNA of the liRNA and activating immune responses in a manner dependent on the structure of the liRNA. For example, when the siRNA is used as an siRNA that targets a cancer-related gene such as siSurvivin or siβ-catenin, it can inhibit the expression of the cancer-related gene and can also induce interferon to activate immune responses, thereby exhibiting a synergistic effect on the inhibition of cancer cell growth. Thus, liRNA according to the present invention will be very useful as an anticancer therapeutic agent.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for labeling or isolating a target material interacting with a bait, the method comprising the steps of:
   (i) providing mediator (regulator) materials, bait materials and nano-assembly matrix-forming materials to the same field or system;
   (ii) forming a nano-assembly unit matrix and/or nano-assembly matrix by the interaction between the mediator (regulator) materials; the mediator (regulator) materials and the bait materials; the bait materials; the nano-assembly matrix-forming materials; the mediator (regulator) materials and the nano-assembly forming materials; and/or the bait materials and the nano-assembly forming materials to display the bait materials;
   (iii) providing a library of prey materials to the nano-assembly unit matrix and/or nano-assembly matrix;
   (iv) labeling and selecting a prey material as the target material by interaction with the bait materials displayed on the nano-assembly unit matrix and/or nano-assembly matrix;
   (v) confirming the labeled target material using an energy transfer or signal change; and
   (vi) isolating and identifying the nano-assembly unit matrix and/or nano-assembly matrix containing the bait material, the mediator (regulator) material and the confirmed target material,
   wherein at least one of the mediator (regulator) material, the bait material, the nano-assembly material-forming material and the prey material is labeled with a label,
   wherein the energy transfer or signal change is measured quantitatively to confirm the specificity of interaction between the bait materials, the mediator (regulator) materials and the prey materials.

2. The method of claim 1, wherein a material that mediates or regulates the interaction between the mediator (regulator) materials; the mediator (regulator) materials and the bait materials; the bait materials; the nano-assembly matrix-forming materials; the mediator (regulator) materials and the nano-assembly forming materials; and/or the bait materials and the nano-assembly forming materials is added.

3. The method of claim 1, wherein the library of prey materials is labeled with a label, and at least one of the nano-assembly material-forming material, the bait material, and the mediator (regulator) material is additionally labeled with a label.

4. The method of claim 1, wherein two or more different nano-assembly matrix-forming materials are used.

5. The method of claim 1, wherein the interaction between the bait materials with the prey materials occurs directly.

6. The method of claim 1, wherein at least one material is additionally added which mediates (regulates) the interaction between the bait materials, the prey materials, or the nano-assembly matrix-forming materials.

7. The method of claim 6, wherein the at least one material is added with the material fused to the bait materials, the prey materials, or the nano-assembly matrix-forming materials.

8. The method of claim 1, wherein the bait materials, the prey materials, or the mediator (regulator) materials are bioactive molecules.

9. The method of claim 8, wherein the bioactive molecules are one or more selected from the group consisting of nucleic acids, nucleotides, proteins, peptides, amino acids, saccharides, lipids, vitamins, and chemical compounds.

10. The method of claim 1, wherein a material that mediates or regulates the interaction between the mediator (regulator) materials is added.

11. The method of claim 1, wherein the label is selected from the group consisting of magnetic materials, radioactive materials, enzymatic materials for ELISA, fluorescent materials, and luminescent materials.

12. The method of claim 11, wherein the fluorescent materials are selected from the group consisting of fluorescent dyes, fluorescent proteins and fluorescent nanoparticles.

13. The method of claim 1, wherein the nano-assembly matrix-forming materials are poly/multi-valent materials that have a plurality of the same or different binding moieties and can form matrices by the interaction or self-assembly between them.

14. The method of claim 13, wherein the nano-assembly matrix-forming materials are selected from the group consisting of proteins having self-assembly or self-association domains, gold nanoparticles, Q dots, and magnetic nanoparticles.

15. The method of claim 14, wherein the proteins having self-assembly or self-association domains are selected from the group consisting of ferritin, ferritin-like protein, DPS (DNA binding protein from starved cells), DPS-like protein, HSP (heat shock protein), magnetosome protein, viral protein, calcium/calmodulin-dependent kinase II, and dsRed.

16. The method of claim 1, wherein the method is performed in a cell, a tissue or a living body.

17. The method of claim 1, wherein the energy transfer or signal change is either the energy transfer caused by the resonance between label molecules or the change in intensity or pattern of images or signals caused by the label.

18. The method of claim 1, wherein the energy transfer or signal change is measured by any one selected from the group consisting of a magnetic method, a radioactive method, a method employing an enzyme for ELISA, a method of detecting a fluorescent or luminescent material, an optical method, a method employing a microscope, an imaging system, a scanner, a reader, a spectrophotometer, MRI (magnetic resonance imaging), SQUID, an MR relaxometer, flow Cytometry, FACS (fluorescene associated cell sorting), a fluorometer, and a luminometer.

* * * * *